US008440654B2

(12) United States Patent
Edwards et al.

(10) Patent No.: US 8,440,654 B2
(45) Date of Patent: May 14, 2013

(54) THIENO- AND FURO-PYRIMIDINE MODULATORS OF THE HISTAMINE H4 RECEPTOR

(75) Inventors: James P. Edwards, San Diego, CA (US); Danielle K. Neff, La Jolla, CA (US); Deborah M. Smith, San Diego, CA (US); Jennifer D. Venable, Solana Beach, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/456,148

(22) Filed: Apr. 25, 2012

(65) Prior Publication Data

US 2012/0238544 A1    Sep. 20, 2012

Related U.S. Application Data

(62) Division of application No. 12/283,700, filed on Sep. 12, 2008, now Pat. No. 8,193,178.

(60) Provisional application No. 60/972,589, filed on Sep. 14, 2007.

(51) Int. Cl.
| | |
|---|---|
| C07D 491/04 | (2006.01) |
| C07D 243/08 | (2006.01) |
| A61K 31/519 | (2006.01) |
| A61K 31/5513 | (2006.01) |
| A61K 31/5025 | (2006.01) |
| A61K 31/501 | (2006.01) |
| A61P 29/00 | (2006.01) |

(52) U.S. Cl.
USPC ........ 514/218; 544/278; 544/250; 514/260.1; 514/249; 514/267; 514/252.15; 514/252.16; 540/575

(58) Field of Classification Search . 544/278; 514/260.1
See application file for complete search history.

(56) References Cited

U.S. PATENT DOCUMENTS

| | | | |
|---|---|---|---|
| 3,907,801 | A | 9/1975 | Wu et al. |
| 5,965,582 | A | 10/1999 | Lebaut et al. |
| 7,253,200 | B2 | 8/2007 | Buzzard et al. |
| 8,193,178 | B2 | 6/2012 | Edwards et al. |
| 2005/0153989 | A1 | 7/2005 | Grotzfeld et al. |
| 2006/0281768 | A1 | 12/2006 | Gaul et al. |

FOREIGN PATENT DOCUMENTS

| | | |
|---|---|---|
| EP | 1437348 | 7/2004 |
| EP | 1505064 | 2/2005 |
| EP | 1767537 | 3/2007 |
| WO | WO2005/054239 | 6/2005 |
| WO | WO 2006/050965 | 5/2006 |
| WO | WO 2007/090852 | 8/2007 |
| WO | WO 2007/090853 | 8/2007 |
| WO | WO 2009/068512 | 6/2009 |

OTHER PUBLICATIONS

U.S. Appl. No. 13/456,180, filed Apr. 25, 2012, Edwards, et al.
U.S. Appl. No. 13/456,165, filed Apr. 25, 2012, Edwards, et al.
U.S. Appl. No. 13/456,174, filed Apr. 25, 2012, Edwards, et al.
Altenbach, Robert et al., Structure-Activity Studies on a Series of a 2-Aminopyrimidine-Containing Histamine H4 Receptor Ligands, Jour. Med. Chem. (2008), 51(20), pp. 6571-6580.
Amin et al. "Inflammation and Structural Changes in the Airways of Patients with Atopic and NonAtopic Asthma" Am J Respir Crit Care Med 2000 vol. 162(6) pp. 2295-2301.
Bagshawe et al. "Antibody-Directed Enzyme Prodrug Therapy: A Review" Drug Dev Res 1995 vol. 34 pp. 220-230.
Becker et al "Preparation of pyrimidine derivatives as potential medicinal agents by the reaction of 2-amino-4-chloro-6-methylpyrimidine with primary and secondary amines", *Journal of Heterocyclic Chemistry*, 2005, 42(7), pp. 1289-1295.
Bell et al "Involvement of Histamine $H_4$ and $H_1$ Receptors in Scratching Induced by Histamine Receptor Agonists in BalbC Mice" Br J Pharmaol 2004 vol. 142(2) pp. 374-380.
Benoist et al "Mast Cells in Autoimmune Disease" Nature 2002 vol. 420(6917) pp. 875-878.
Berge et al. "Pharmaceutical Salts" Journal of Pharmaceutical Sciences 1977 vol. 66(1) pp. 1-19.
Bertolini et al. "A New Rational Hypothesis for the Pharmacophore of the Active Metabolite of Leflunomide, A Potent Immunosuppressive Drug" J Med Chem 1997 vol. 40 pp. 2011-2016.
Bodor et al. "Novel Approaches to the Design of Safer Drugs: Soft Drugs and Site-Specific Chemical Delivery Systems" Advances in Drug Research 1984 vol. 13 pp. 224-331.
Buckland et al "Histamine Induces Cytoskeletal Changes in Human Eosinophils via the $H_4$ Receptor" Br J Pharmacol 2003 vol. 140(6) pp. 1117-1127.
Cheng et al "Relationship between the inhibition constant (K1) and the concentration of inhibitor which causes 50 per cent inhibition (I50) of an enzymatic reaction" *Biochemical Pharmacology*, 1973, 22(23), pp. 3099-3108.
Coge et al "Structure and Expression of the Human Histamine $H_4$—Receptor Gene" Biochem Biophys Res Commun 2001 vol. 284(2) pp. 301-309.
Cohen J. "The Immunopathogenesis of Sepsis" Nature 2002 vol. 420(6917) pp. 885-891.
Coussens et al "Inflammation and Cancer" Nature 2002 vol. 420(6917) pp. 860-867.
Crimi et al "Increased Numbers of Mast Cells in Bronchial Mucosa After the Late Phase Asthmatic Response to Allergen" Am Rev Respir Dis 1991 vol. 144(6) pp. 1282-1286.
De Esch et al. "The Histamine $H_4$ Receptor as a New Therapeutic Target for Inflammation" Trends Pharmacol Sci 2005 vol. 26(9) pp. 462-469.
Dunford, P.J. et al. The histamine H4 receptor mediates allergic airway inflammation by regulating the activation of CD4+ T cells. Journal of Immunology, 2006. vol. 176(11) , 7062-7070.
Dunford, P.J. et al. Histamine H4 receptor antagonists are superior to traditional antihistamines in the attenuation of experimental pruritus. J. Allergy Clin. Immunol. 2007, vol. 119(1), 176-183.

(Continued)

*Primary Examiner* — Susanna Moore

(57) ABSTRACT

Thieno- and furo-pyrimidine compounds are described, which are useful as $H_4$ receptor modulators. Such compounds may be used in pharmaceutical compositions and methods for the modulation of histamine $H_4$ receptor activity and for the treatment of disease states, disorders, and conditions mediated by $H_4$ receptor activity, such as inflammation.

7 Claims, No Drawings

OTHER PUBLICATIONS

Fleisher et al. "Improved Oral Delivery: Solubility Limitations Overcome by the Use of Prodrugs" Advanced Drug Delivery Review 1996 vol. 19 pp. 115-130.

Fokkens et al "Dynamics of Mast Cells in the Nasal Mucosa of Patients with Allergic Rhinitis and Non-Allergic Controls: A Biopsy Study" Clin Exp Allergy 1992 vol. 22(7) pp. 701-710.

Fung-Leung et al. "Histamine $H_4$ Receptor Antagonists: The New Antihistamines?" Curr Opin Invest Drugs 2004 vol. 5(11) pp. 1174-1183.

Gantner et al. "Histamines $H_4$ and $H_2$ Receptors Control Histamine-Induced Interleukin-16 Release from Human CD8+ T Cells" J Pharmacol Exp Ther 2002 vol. 303(1) pp. 300-307.

Gauvreau et al "Increased Numbers of Both Airway Basophils and Mast Cells in Sputum after Allergen Inhalation Challenge of Atopic Asthmatics" Am J Resp Crit Care Med 2002 vol. 161(5) pp. 1473-1478.

Greenwald et al. "Drug delivery systems. 2. Camptothecin 20-O-poly(ethylene glycol) ester transport forms" Journal of Medicinal Chemistry, 1996, 39(10), pp. 1938-1940.

Gutzmer et al "Histamine $H^4$ Receptor Stimulation Suppresses IL-12p70 Production and Mediates Chemotaxis in Human Monocyte-Derived Dendritic Cells" J Immunol 2005 vol. 174(9) pp. 5224-5232.

Hofstra et al "Histamine $H^4$ Receptor Mediates Chemotaxis and Calcium Mobilization of Mast Cells" J Pharmacol Exp Ther 2003 vol. 305(3) pp. 1212-1221.

Horr et al. STAT1 phosphorylation and cleavage is regulated by the histamine (H4) receptor in human atopic and non-atopic lymphocytes. International Immunopharmacology 2006, vol. 6 (10), 1577-1585.

Ikawa et al "Histamine $H^4$ Receptor Expression in Human Synovial Cells Obtained from Patients Suffering from Rheumatoid Arthristis" Biol Pharm Bull 2005 vol. 28(10) pp. 2016-2018.

Jablonowski, J. et al., The first potent and selective non-imidazole human histamine H4 receptor antagonists. Journal of Medicinal Chemistry, 2003. vol. 46(19), 3957-3960.

Jiang et al. Cloning and pharmacological characterization of the dog histamine H-4 receptor. European Journal of Pharmacology, 2008. vol. 592(1-3), 26-32.

Jokuti et al. Histamine H4 receptor expression is elevated in human nasal polyp tissue, Cell Biology International. 2007 vol. 31(11) 1367-1370.

Kassel et al. "Local Increase in the Number of Mast Cells and Expression of Nerve Growth Factor in the Bronchus of Asthmatic Patients after Repeated Inhalation of Allergen Low-Dose" Clin Exp Allergy 2001 vol. 31(9) pp. 1432-1440.

Kirby et al "Bronchoalveolar Cell Profiles of Asthmatic and NonAsthmatic Subjects" Am Rev Respir Dis 1987 vol. 136(2) pp. 379-383.

Kiss, R. et al. Histamine H4 receptor ligands and their potential therapeutic applications. Expert Opin. Ther. Patents, 2009, vol. 19(2), 119-135.

Krug et al "Interleukin 16 and T-cell Chemoattractant Activity in Bronchoalveolar Lavage 24 Hours After Allergen Challenge in Asthma" Am J Resp Crit Care Med 2000 vol. 162(1) pp. 105-111.

Lee-Dutra, A. et al., Identification of 2-arylbenzimidazoles as potent human histamine H-4 receptor ligands, Bioorganic & Medicinal Chemistry Letters 2006. vol. 16(23), 6043-6048.

Leite-de-Moraes, Cutting edge: histamine receptor H4 activation positively regulates in vivo IL-4 and IFN-gamma production by invariant NKT cells. Journal of Immunology, 2009. 182(3):1233-1236.

Lespagnol et al "Recherches Dans La Serie Pyrimidique", Chim. Therap. 1971, 6(2), pp. 105-108.

Lespagnol et al "Recherches dans la serie sulfonamide" Chim, Therap. 1965, 1, pp. 26-31.

Libby P. "Inflammation in Atherosclerosis" Nature 2002 vol. 420 pp. 868-874.

Lim, H. et al., Evaluation of histamine H-1-, H-2-, and H-3-receptor ligands at the human histamine H-4 receptor: Identification of 4-methylhistamine as the first potent and selective H-4 receptor agonist. Journal of Pharmacology & Experimental Therapeutics, 2005, vol. 314(3), 1310-1321.

Ling et al. "Histamine $H^4$ Receptor Mediates Eosiniphil Chemolaxis with Cell Shape Change and Adhesion Molecule Upregulation" British Journal of Pharmacology, 2004, 142(1) pp. 161-171.

Lippert et al. "Human skin mast cells express H2 and H4, but not H3 receptors" Journal of Investigative Dermatology, 2004,123(1) pp. 116-123.

Liu et al "Cloning of Pharmacological Characterization of a Fourth Histamine Receptor ($H^4$) Expressed in Bone Marro" Mol Pharmacol 2001 vol. 59(3) pp. 420-426.

Liu et al "Comparison of human, mouse, rat, and guinea pig histamine H4 receptors reveals substantial pharmacological species variation" Journal of Pharmacology & Experimental Therapeutics, 2001, 299(1), 121-130.

Mashikian et al "Identification of IL-16 as the Lymphocyte Chemotactic Activity in the Bronchoalveolar Lavage Fluid of Histamine-Challenged Asthmatic Patients" J Allergy Clin Immunol 1998 vol. 101(6, Part 1) pp. 786-792.

Morse et al "Cloning and Characterization of Novel Human Histamine Receptor" J Pharmacol Exp. Ther 2001 vol. 296(3) pp. 1058-1066.

Nathan C. "Points of Control in Inflammation" Nature 2002 vol. 420(6917) pp. 846-852.

O'Reilly et al "Identification of $H^4$ Receptor in Human Eosinophilis—Role in Eosinophil Chemotaxis" J Recept Signal Transduction 2002 vol. 22(1-4) pp. 431-448.

Robinson et al. "Discovery of the hemifumarate and (alpha-L-alanyloxy)methyl ether as prodrugs of an antirheumatic oxindole: Prodrugs for the enolic OH group", Journal of Medicinal Chemistry, 1996, 39(1), pp. 10-18.

Shan et al. "Prodrug strategies based on intramolecular cyclization reactions", Journal of Pharmaceutical Sciences 1997, 86(7), pp. 765-767.

Slater et al "Increase in epithelial Mast Cell Numbers in the Nasal Mucosa of Patients with Perennial Allergic Rhinitis" J Laryngol Otol 1996 vol. 110 pp. 929-933.

Smith, D.M. et al. "Tricyclic Histamine $H_4$ Receptor Antagonists". American Chemical Society Meeting, San Francisco, Mar. 2010.

Smits, R.A. et al. Major advances in the development of histamine H4 receptor ligands. Drug Discovery Today, 2009, vol. 14(15-16):745-753.

Steinberg D. "Atherogenesis in Perspective: Hypercholesterolemia and Inflammation as Partners in Crime" Nature Med 2002 vol. 8(11) pp. 1211-1217.

Takeshita et al "Critical Role of Histamine $H_4$ Receptor in Leukotriene $B_4$ Production and Mast-Cell Dependent Neutrophil Recruitment Induced by Zymosan in Vivo" J Pharmacol Exp Ther 2003 vol. 307(3) pp. 1072-1078.

Thurmond et al "A Potent and Selective Histamine $H_4$ Receptor Antagonist with Anti-Inflammatory Properties" J Pharmacol Exp Ther 2004 vol. 309(1) pp. 404-413.

Thurmond R. L. et al , The role of histamine H1 and H4 receptors in allergic inflammation: the search for new antihistamines. Nat. Rev. Drug Disc. 2008 vol. 7(1), 45-53.

Tracey K. J. "The Inflammatory Reflex" Nature 2002 vol. 420(6917) pp. 853-859.

Varga et al "Inhibitory Effects of Histamine $H^4$ Receptor Antagonists on Experimental Colitis in the Rat" Eur J Pharmacol 2005 vol. 522(1-3) pp. 130-138.

Venable, J.D. et al. Preparation and biological evaluation of indole, benzimidazole, and thienopyrrole piperazine carboxamides: Potent human histamine $H_4$ antagonists. Journal of Medicinal Chemistry, 2005. vol. 48(26), 8289-8298.

Voehringer et al "Type 2 Immunity Reflects Orchestrated Recruitment of Cells Committed to IL-4 Production" Immunity 2004 vol. 20(3) pp. 267-277.

Weiner et al "Inflammation and Therapeutic Vaccination in CNS Diseases" Nature 2002 vol. 420(6917) pp. 879-884.

Willecomme B. "Recherches Dans La Serie De La Piperazine", Annales de Chimie 1969, 4(6), pp. 405-428.

Zhang, M. et al. The histamine $H_4$ receptor in autoimmune disease. Expert Opinion on Investigational Drugs, 2006. vol. 15(11), 1443-1452.

Zhang, M. et al. The Histamine H4 Receptor: A Novel Mediator of Inflammatory and Immune Disorders. Pharmacol. Ther. 2007. vol. 113, 594-606.

THIENO- AND FURO-PYRIMIDINE MODULATORS OF THE HISTAMINE H4 RECEPTOR

This application is a divisional of U.S. patent application Ser. No. 12/283,700 filed Sep. 12, 2008 now U.S. Pat. No. 8,193,178, which claims the benefit of U.S. provisional patent application Ser. No. 60/972,589, filed on Sep. 14, 2007, all of which are incorporated herein by reference.

FIELD OF THE INVENTION

The present invention relates to certain thieno- and furo-pyrimidine compounds, pharmaceutical compositions containing them, and methods of using them for the modulation of the histamine $H_4$ receptor and for the treatment of disease states, disorders, and conditions mediated by histamine $H_4$ receptor activity.

BACKGROUND OF THE INVENTION

The histamine $H_4$ receptor ($H_4R$) is the most recently identified receptor for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Liu, C., et al., J. Pharmacology and Experimental Therapeutics 2001, 299, 121-130; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), CD8$^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4$ receptor activation influences inflammatory responses. Because of its preferential expression on immunocompetent cells, the $H_4$ receptor is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4$ receptor knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4$ receptor dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by histamine $H_4$ receptors.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4$ receptor (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4$ receptor antagonists but not by $H_1$, $H_2$, or $H_3$ receptor antagonists.

The $H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174 (9), 5224-5232). A role for the $H_4$ receptor in CD8$^+$ T cells has also been reported. Gantner, et al., (2002) showed that both $H_4$ and $H_2$ receptors control histamine-induced IL-16 release from human CD8$^+$ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Grit. Care Med. 2000, 162(1), 105-111) and is considered important in CD4$^+$ cell migration. The activity of the receptor in these cell types indicates an important role in adaptive immune responses such as those active in autoimmune diseases.

In vivo $H_4$ receptor antagonists were able to block neutrophillia in zymosan-induced peritonitis or pleurisy models (Takeshita, K., et al., J. Pharmacol. Exp. Ther. 2003, 307(3), 1072-1078; Thurmond, et al., 2004). In addition, $H_4$ receptor antagonists have activity in a widely used and well-characterized model of colitis (Varga, C., et al., Eur. J. Pharmacol. 2005, 522(1-3), 130-138). These results support the conclusion that $H_4$ receptor antagonists have the capacity to be anti-inflammatory in vivo.

Another physiological role of histamine is as a mediator of itch and $H_1$ receptor antagonists are not completely effective in the clinic. Recently, the $H_4$ receptor has also been implicated in histamine-induced scratching in mice (Bell, J. K., et al., Br. J. Pharmacol. 2004, 142(2), 374-380). The effects of histamine could be blocked by $H_4$ antagonists. These results support the hypothesis that the $H_4$ receptor is involved in histamine-induced itch and that $H_4$ receptor antagonists will therefore have positive effects in treating pruritis.

Modulation of H₄ receptors controls the release of inflammatory mediators and inhibits leukocyte recruitment, thus providing the ability to prevent and/or treat H₄-mediated diseases and conditions, including the deleterious effects of allergic responses such as inflammation. Compounds according to the present invention have H₄ receptor modulating properties. Compounds according to the present invention have leukocyte recruitment inhibiting properties. Compounds according to the present invention have anti-inflammatory properties.

Examples of textbooks on the subject of inflammation include: 1) Gallin, J. I.; Snyderman, R., *Inflammation: Basic Principles and Clinical Correlates*, 3rd ed.; Lippincott Williams & Wilkins: Philadelphia, 1999; 2) Stvrtinova, V., et al., Inflammation and Fever. *Pathophysiology Principles of Diseases* (Textbook for Medical Students); Academic Press: New York, 1995; 3) Cecil; et al. *Textbook Of Medicine*, 18th ed.; W.B. Saunders Co., 1988; and 4) Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Small-molecule histamine H₄ receptor modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritis, and immunodeficiency disorders. Diseases, disorders and medical conditions that are mediated by histamine H₄ receptor activity include those referred to herein.

Certain cyclic amine-substituted 2-aminopyrimidines are disclosed in the following publications: Becker, I. J. Het. Chem. 2005, 42(7), 1289-1295; Eur. Pat. Appl. No. EP 1437348 (Jul. 14, 2004); U.S. Pat. No. 3,907,801 (Sep. 23, 1975); Lespagnol, A. et al. Chim. Therap. 1971, 6(2), 105-108; Willecomme, B. Annales de Chimie 1969, 4(6), 405-428; Lespagnol, A. et al. Chim. Therap. 1965, 1, 26-31; US 2006/281768; and US 2005/153989.

Certain substituted 2-aminopyrimidines as histamine H₄ antagonists are disclosed in Intl. Pat. Appl. Publ. WO2005/054239 (Jun. 16, 2005) and EP 1505064 (Feb. 9, 2005). However, there remains a need for potent histamine H₄ receptor modulators with desirable pharmaceutical properties. Certain 2-aminopyrimidine derivatives have been found in the context of this invention to have histamine H₄ receptor-modulating activity.

SUMMARY OF THE INVENTION

In one aspect the invention relates to chemical entity selected from the group consisting of compounds of the following Formula (I), pharmaceutically acceptable salts of compounds of Formula (I), pharmaceutically acceptable prodrugs of compounds of Formula (I), and pharmaceutically active metabolites of compounds of Formula (I):

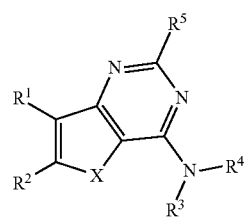

wherein

X is O or S;

R¹ is H, methyl, or bromo;

R² is H or C₁₋₄alkyl;

or R¹ and R² taken together form —(CH₂)₄₋₅— optionally substituted with one or two substituents independently selected from C₁₋₄alkyl, C₁₋₄alkoxy, CF₃, and fluoro;

—N(R³)R⁴ is one of the following moieties, wherein R³ and R⁴ are taken together or separately as defined by each one of said moieties:

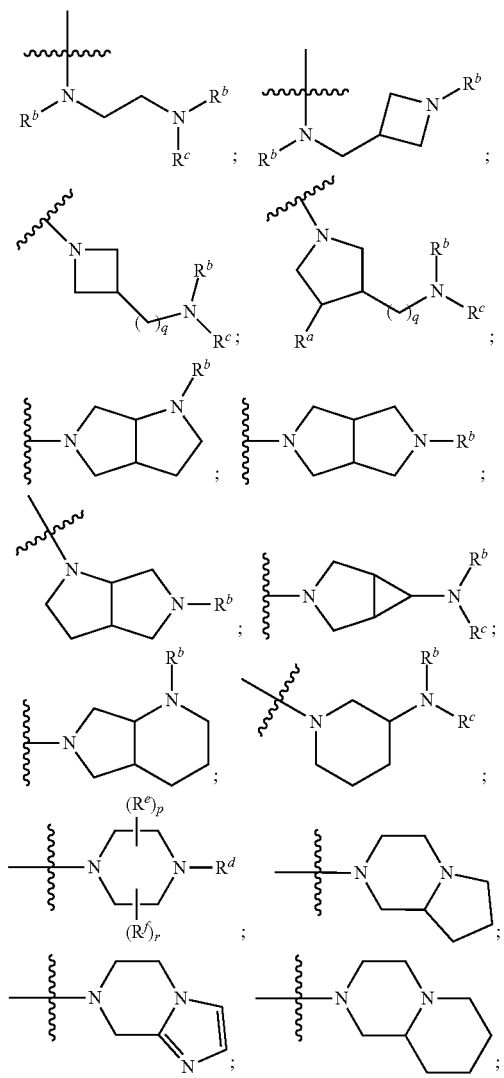

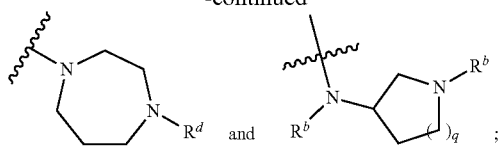

where q is 0 or 1;
p is 0 or 1;
r is 0 or 1;
$R^a$ is H or OH;
$R^b$ and $R^c$ are each independently H or $C_{1-3}$alkyl;
$R^d$ is H or a $C_{1-3}$alkyl group unsubstituted or substituted with OH or $NH_2$;
$R^e$ and $R^f$ are each methyl, or $R^e$ and $R^f$ taken together form a methylene or ethylene bridge; and
$R^5$ is H or $NH_2$;
provided that when $R^1$ is H and $R^2$ is H, methyl, or tert-butyl, then —N($R^3$)$R^4$ is not 3-aminopyrrolidine, 3-aminopiperidine, piperazine, or N-methylpiperazine.

Some embodiments of this invention are provided by chemical entities such as compounds selected from those species described or exemplified in the detailed description below, pharmaceutically acceptable salts of such compounds, pharmaceutically acceptable prodrugs of such compounds, and pharmaceutically acceptable metabolites of such compounds.

In a further aspect, the invention relates to pharmaceutical compositions each comprising an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Pharmaceutical compositions according to the invention may further comprise a pharmaceutically acceptable excipient.

In another aspect, the chemical entities of the present invention are useful as histamine $H_4$ receptor modulators. Thus, the invention is directed to a method for modulating histamine $H_4$ receptor activity, including when such receptor is in a subject, comprising exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from or diagnosed with a disease, disorder, or medical condition mediated by histamine $H_4$ receptor activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION OF INVENTION AND ITS PREFERRED EMBODIMENTS

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a "/" symbol), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

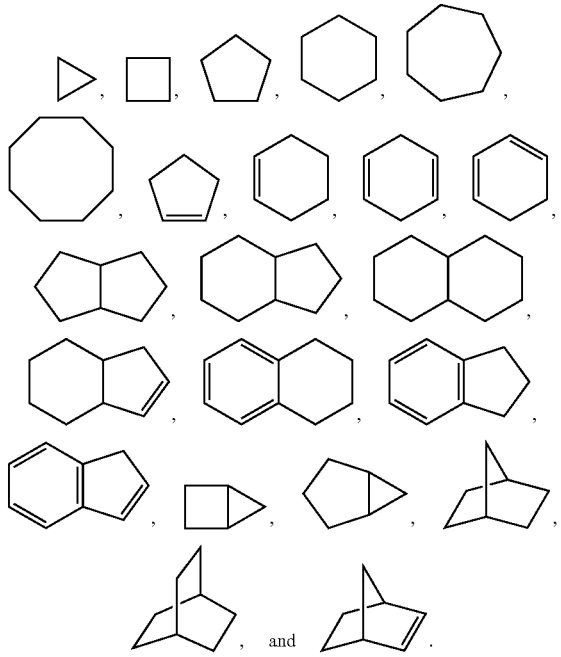

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

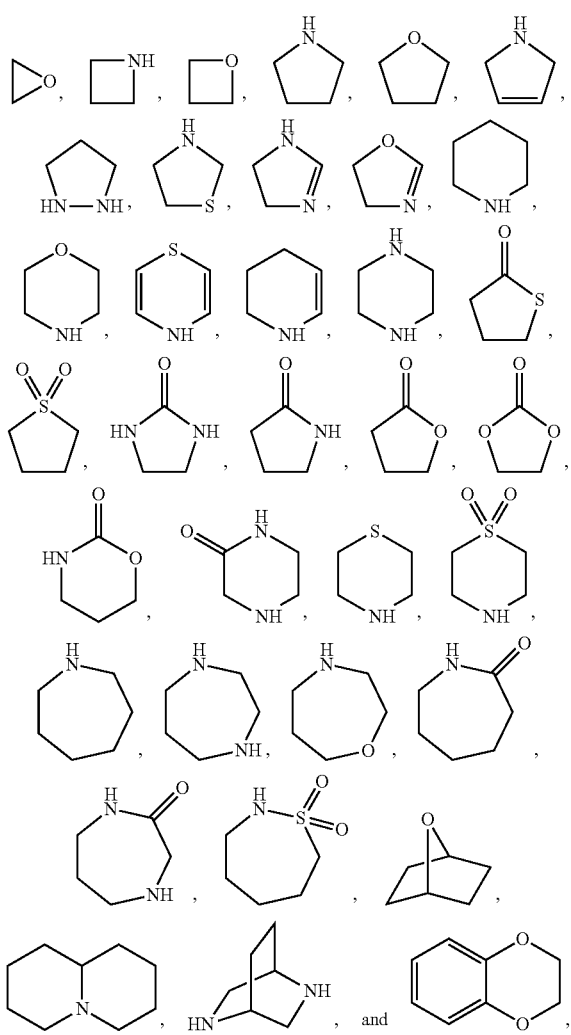

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

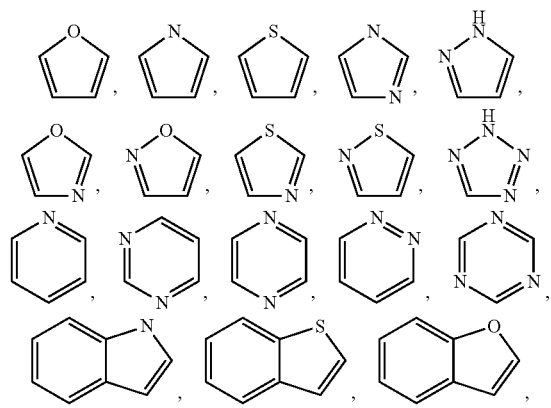

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to represent hydrates, solvates, and polymorphs of such compounds, and mixtures thereof.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S_{example}$ is $S_1$ and $S^2_{example}$ is $S_4$; $S_{example}$ is $S_2$ and $S^2_{example}$ is $S_3$; $S_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as X, $R^{1-5}$, $R^{a-e}$, and q, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as X, $R^{1-5}$, $R^{a-e}$, and q, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≦N≦m, with m>n.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

In some embodiments of Formula (I), X is O.

In some embodiments, $R^1$ is H.

In some embodiments, $R^2$ is H or tert-butyl.

In some embodiments, $R^1$ and $R^2$ taken together form —$(CH_2)_4$— optionally substituted with a methyl, dimethyl, tert butyl, $CF_3$ or two fluoro substituents.

In some embodiments, —$N(R^3)R^4$ is one of the following moieties:

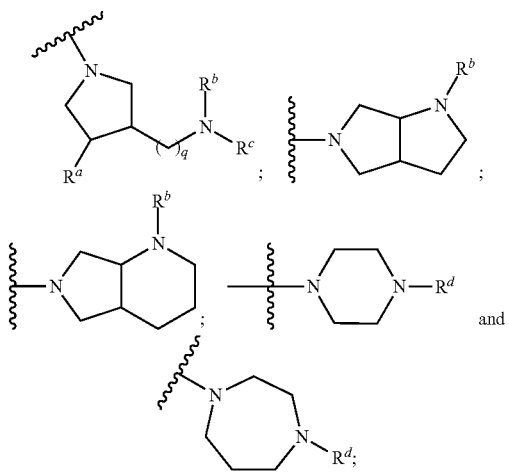

where q is 0;
$R^a$ is H;
$R^b$ and $R^c$ are each independently H or methyl; and
$R^d$ is H or methyl.

In other embodiments, —$N(R^3)R^4$ is one of the following moieties:

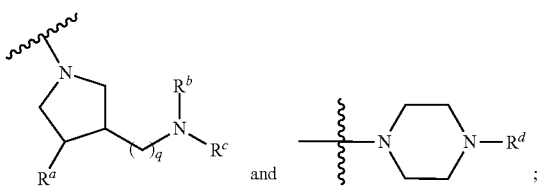

where q is 0;
$R^a$ is H;
$R^b$ and $R^c$ are each independently H or methyl; and
$R^d$ is H or methyl.

In some embodiments, $R^5$ is $NH_2$.

The invention includes also pharmaceutically acceptable salts of the compounds represented by Formula (I), preferably of those described above and of the specific compounds exemplified herein, and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites, whether alone or in combination, (collectively, "active agents") of the present invention are useful as histamine $H_4$ receptor modulators in the methods of the invention. Such methods for modulating histamine $H_4$ receptor activity comprise exposing histamine $H_4$ receptor to an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit histamine $H_4$ receptor activity.

In some embodiments, the histamine $H_4$ receptor is in a subject with a disease, disorder, or medical condition mediated through modulation of the histamine $H_4$ receptor, such as those described herein. Symptoms or disease states are intended to be included within the scope of "medical conditions, disorders, or diseases."

Accordingly, the invention relates to methods of using the active agents described herein to treat subjects diagnosed with or suffering from a disease, disorder, or condition mediated through histamine $H_4$ receptor activity, such as inflammation. Active agents according to the invention may therefore be used as an anti-inflammatory agents.

In some embodiments, an active agent of the present invention is administered to treat inflammation. Inflammation may be associated with various diseases, disorders, or conditions, such as inflammatory disorders, allergic disorders, dermatological disorders, autoimmune disease, lymphatic disorders, and immunodeficiency disorders, including the more specific conditions and diseases given below. Regarding the onset and evolution of inflammation, inflammatory diseases or inflammation-mediated diseases or conditions include, but are not limited to, acute inflammation, allergic inflammation, and chronic inflammation.

Illustrative types of inflammation treatable with a histamine $H_4$ receptor-modulating agent according to the invention include inflammation due to any one of a plurality of conditions such as allergy, asthma, dry eye, chronic obstructed pulmonary disease (COPD), atherosclerosis, rheumatoid arthritis, multiple sclerosis, inflammatory bowel diseases (including colitis, Crohn's disease, and ulcerative colitis), psoriasis, pruritis, itchy skin, atopic dermatitis, urticaria (hives), ocular inflammation (e.g., post-surgical ocular inflammation), conjunctivitis, dry eye, nasal polyps, allergic rhinitis, nasal itch, scleroderma, autoimmune thyroid diseases, immune-mediated (also known as type 1) diabetes mellitus and lupus, which are characterized by excessive or prolonged inflammation at some stage of the disease. Other autoimmune diseases that lead to inflammation include Myasthenia gravis, autoimmune neuropathies, such as Guillain-Barré, autoimmune uveitis, autoimmune hemolytic anemia, pernicious anemia, autoimmune thrombocytopenia, temporal arteritis, anti-phospholipid syndrome, vasculitides, such as Wegener's granulomatosis, Behcet's disease, dermatitis herpetiformis, pemphigus vulgaris, vitiligio, primary biliary cirrhosis, autoimmune hepatitis, autoimmune oophoritis and orchitis, autoimmune disease of the adrenal gland, polymyositis, dermatomyositis, spondyloarthropathies, such as ankylosing spondylitis, and Sjogren's syndrome.

Pruritis treatable with a histamine $H_4$ receptor-modulating agent according to the invention includes that which is a symptom of allergic cutaneous diseases (such as atopic dermatitis and hives) and other metabolic disorders (such as chronic renal failure, hepatic cholestasis, and diabetes mellitus).

In other embodiments, an active agent of the present invention is administered to treat allergy, asthma, autoimmune diseases, or pruritus.

Thus, the active agents may be used to treat subjects diagnosed with or suffering from a disease, disorder, or condition mediated through histamine $H_4$ receptor activity. The term "treat" or "treating" as used herein is intended to refer to administration of an active agent or composition of the invention to a subject for the purpose of effecting a therapeutic or prophylactic benefit through modulation of histamine $H_4$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_4$ receptor activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_4$ receptor expression or activity, and "activators" are compounds that increase, activate, facilitate, sensitize, or up-regulate histamine $H_4$ receptor expression or activity.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. When referring to modulating the target receptor, an "effective amount" means an amount sufficient to affect the activity of such receptor. Measuring the activity of the target receptor may be performed by routine analytical methods. Target receptor modulation is useful in a variety of settings, including assays. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by histamine $H_4$ receptor activity, such as another histamine $H_4$ receptor modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises an effective amount of at least one active agent in accordance with the invention. Such compositions may further comprise a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

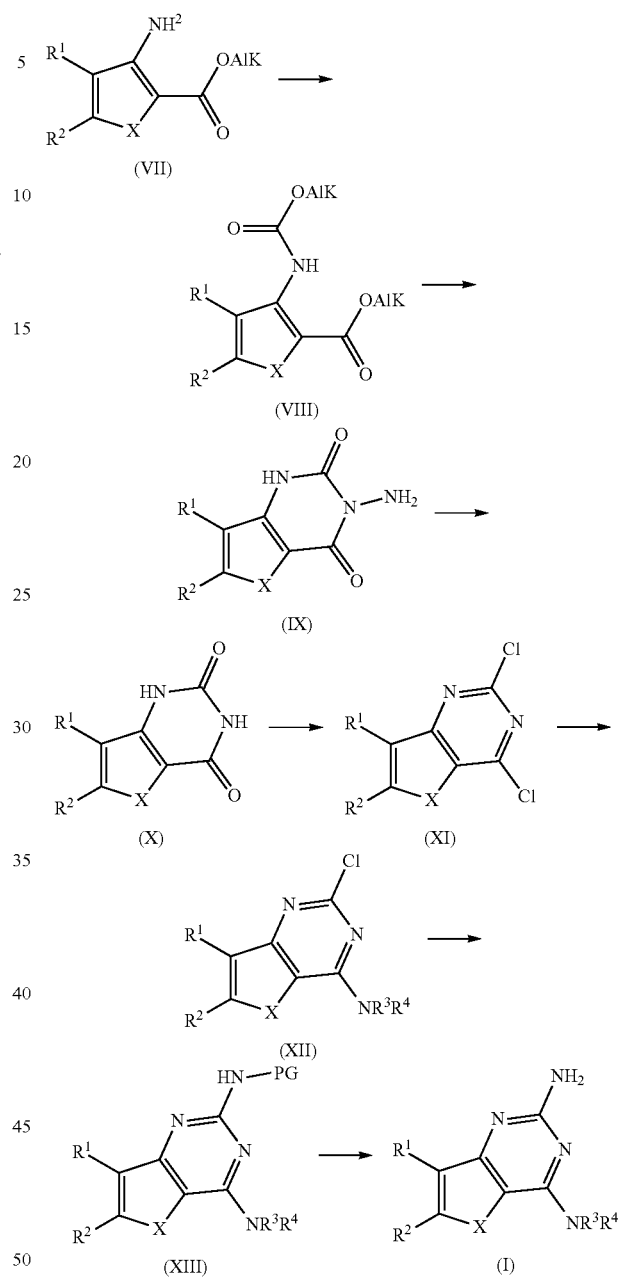

SCHEME A

Compounds of Formula (I) where $R^5$ is —$NH_2$ are prepared according to Scheme A. Reaction of amines (VII) with (Alk)chloroformates (Alk is $C_{1-3}$alkyl), such as ethyl chloroformate, in a solvent such as benzene or toluene, or a mixture thereof, with heating, gives carbamates (VIII). Carbamates (VIII) are reacted with hydrazine, in a solvent such as ethanol (EtOH) or isopropanol, or a mixture thereof, to give aminopyrimidine-diones (IX), which are de-aminated with $NaNO_2$ in a solvent such as acetic acid or water, or a mixture thereof, to give pyrimidine-diones (X). Chlorination using standard methods, such as $POCl_3$ in a solvent such as diethylaniline or dimethylaniline, with heating, gives dichloropyrimidines (XI). Displacement of the 4-chloro substituent with amines, $HN(R^3)R^4$, is accomplished in a solvent such as EtOH, isopropanol, or t-butanol, or a mixture thereof, in the presence of a suitable base, such as K$_2$CO$_3$ or Na$_2$CO$_3$ to give amines (XII). One skilled in the art will recognize that diamines HN(R$^3$)R$^4$ may be suitably protected, and the protecting group removed later in the sequence. Displacement of the 2-chlorosubstituent is performed with protected amine, H$_2$NPG, where PG is an alkyl protecting group (preferably, benzyl, p-methoxybenzyl, or phenethyl), in a solvent such as pyridine, with heating and optionally using microwave irradiation, gives diamines (XIII). Subsequent deprotection of PG (as well as any protecting group on diamines —N(R$^3$)R$^4$, such as a Boc group) using methods known in the art, provides compounds of Formula (I).

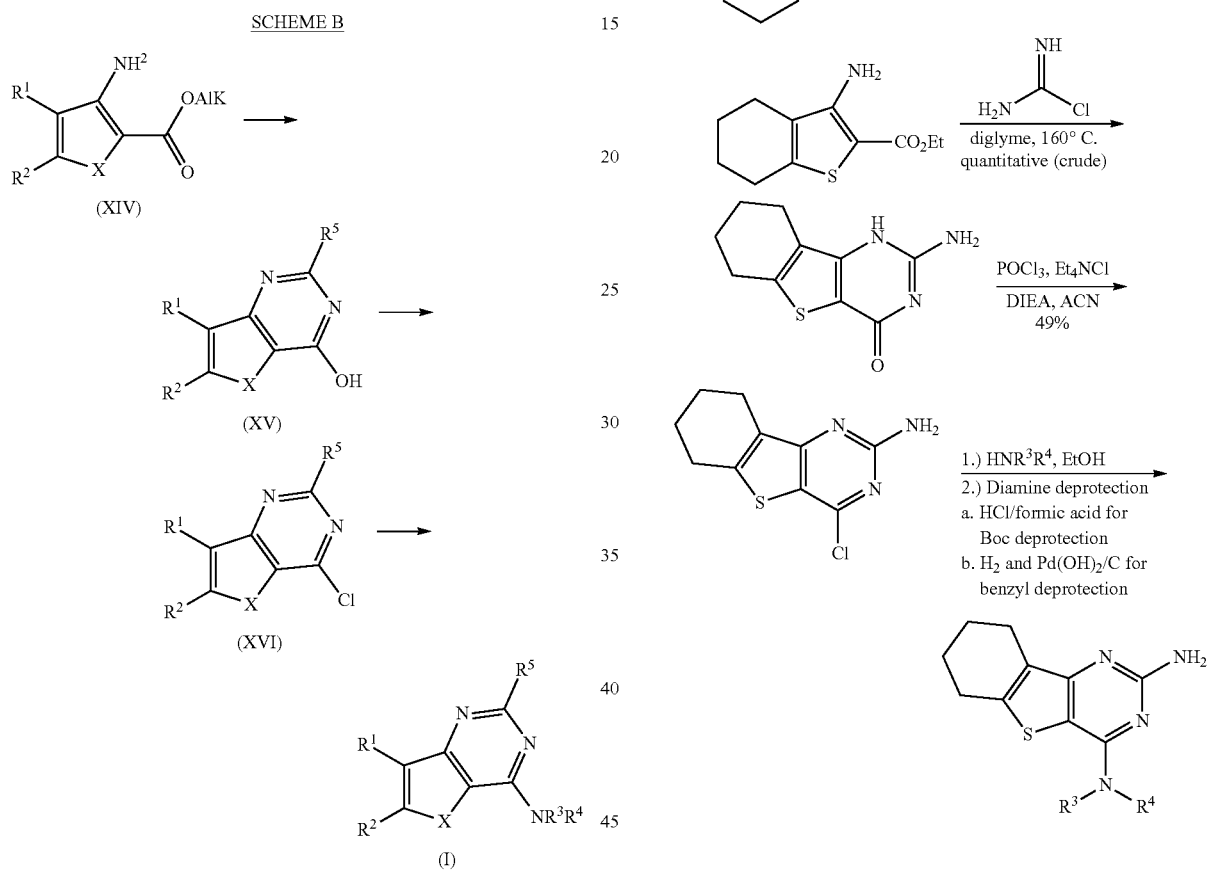

Compounds of Formula (I) are also prepared according to Scheme B. For compounds where R$^5$ is —NH$_2$, condensation of amines (XIV) with chloroformamidine hydrochloride in a high-boiling solvent such as diglyme, with heating, gives hydroxy-pyrimidines (XV) as the hydrochloride salts. Chlorination is effected by treatment with a reagent such as POCl$_3$ in the presence of a tetraalkylammonium salt, such as Et$_4$NCl, in a solvent such as diethylaniline or dimethylaniline to give chlorides (XVI). For compounds where R$^5$ is —H, reaction with formamidine in the presence of a strong base, such as KOtBu, provides hydroxyl-pyrimidines (XV). Chlorination with a reagent such as POCl$_3$ in a solvent such as dimethylaniline or diethylaniline, with heating, gives amino-pyrimidines (XVI) where R$^5$ is —H. For all embodiments of R$^5$, displacement of the 4-chloro substituent with amines, HN(R$^3$)R$^4$, is accomplished in a solvent such as EtOH or pyridine, to provide compounds of Formula (I).

Some embodiments of Scheme B are further exemplified by Schemes B.1 and B.2.

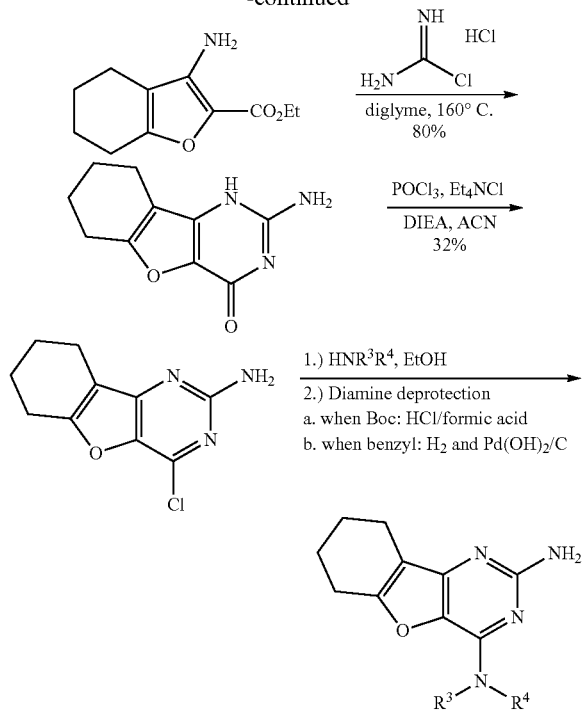

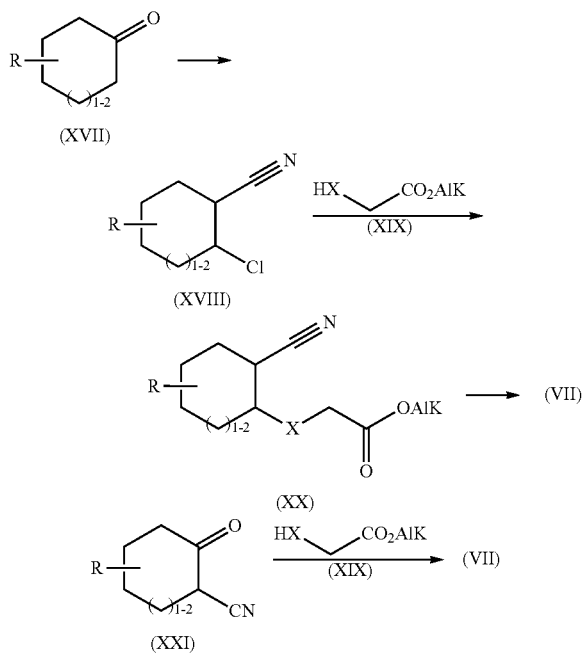

Intermediates of formula (VII) (see, for example, structure in Scheme A) may be prepared according to Scheme C. Substituted ketones (XVII), where R is methyl or fluoro, are converted to nitriles (XVIII) by treatment with POCl$_3$ and H$_2$NOH in a solvent such as N,N-dimethylformamide (DMF), with heating. Reaction of nitriles (XVIII) with hydroxy- or mercapto-acetic acid esters (Alk is C$_{1-3}$alkyl), in a solvent such as EtOH, tetrahydrofuran (THF), or DMF, or a mixture thereof, in the presence of a suitable base, such as K$_2$CO$_3$, with heating, provides intermediates (VII). Alternatively, condensation of keto-nitriles (XXI) with ethyl glycolate or ethyl thioglycolate, in the presence of diethyl or diisopropyl azodicarboxylate and PPh$_3$, with or without subsequent addition of a base such as NaH, in a solvent such as THF, provides intermediates (VII) directly.

Compounds of Formula (I) may be converted to their corresponding salts using methods described in the art. For example, an amine of Formula (I) is treated with trifluoroacetic acid (TFA), HCl, or citric acid in a solvent such as diethyl ether, CH$_2$Cl$_2$, THF, or methanol (MeOH) to provide the corresponding salt form. In certain embodiments, corresponding salts may be obtained by reverse phase purification in acetonitrile and water with TFA as an additive to the purification solvents.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry Methods:

In obtaining the compounds described in the examples below and the corresponding analytical data, the following experimental and analytical protocols were followed unless otherwise indicated.

Unless otherwise stated, reaction mixtures were magnetically stirred at room temperature (rt). Where solutions are "dried," they are generally dried over a drying agent such as Na$_2$SO$_4$ or MgSO$_4$. Where mixtures, solutions, and extracts were "concentrated", they were typically concentrated on a rotary evaporator under reduced pressure.

Normal-phase flash column chromatography (FCC) was performed on silica gel (SiO$_2$) eluting with designated solvents.

Trifluoroacetic acid salt forms of exemplified compounds were obtained by purification of the crude products by reversed-phase high performance liquid chromatography (HPLC) under acidic conditions. Reversed-phase HPLC (acidic conditions) was performed by: 1) a Hewlett Packard HPLC Series 1100 with a Phenomenex Luna C18 (5 µm, 4.6×150 mm) column, detection at λ=230, 254 and 280 nm, and a gradient of 10 to 99% acetonitrile/water (0.05% trifluoroacetic acid) over 5.0 min with a flow rate of 1 mL/min; or 2) a Shimadzu LC-8A equipped with a YMC Pack ODS 250×30 mm column with a gradient of 10 to 50% TFA in acetonitrile and 0.05% in water over 15 min at a rate of 70 mL/min.

Alternatively, purification by reversed-phase HPLC (basic conditions) provided compounds in the free base form. Reversed-phase HPLC (basic conditions) was performed on a Dionex APS2000 LC/MS with a Phenomenex Gemini C18 (5

μm, 30×100 mm) column, and a gradient of 5 to 100% acetonitrile/water (20 mM NH$_4$OH) over 16.3 min, and a flow rate of 30 mL/min.

Hydrochloride salts were prepared by treating a solution of the free base in CHCl$_3$ with HCl (1 M in Et$_2$O). Concentration of the reaction mixture provided the hydrochloride salts.

Mass spectra (MS) were obtained on an Agilent series 1100 MSD using electrospray ionization (ESI) in positive mode unless otherwise indicated. The MS data presented is the m/z found (typically [M+H]$^+$) for the molecular ion.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Version 6.0.2 (CambridgeSoft, Cambridge, Mass.) or ACD/Name Version 9 (Advanced Chemistry Development, Toronto, Ontario, Canada).

Example 1

4-(4-Methyl-piperazin-1-yl)-thieno[3,2-d]pyrimidin-2-ylamine

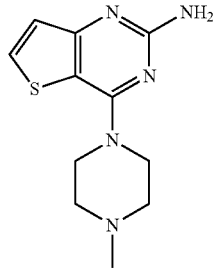 [SMILES: CN1CCN(c2nc(N)nc3ccsc23)CC1]

Step A: 3-Ethoxycarbonylamino-thiophene-2-carboxylic acid methyl ester. To a solution of 3-amino-thiophene-2-carboxylic acid methyl ester (2.39 g, 15.2 mmol) in benzene (51 mL) was added K$_2$CO$_3$ (6.30 g, 45.6 mmol) followed by ethyl chloroformate (1.74 mL, 18.2 mmol). After heating at reflux for 12 h, the mixture was filtered and the filtrate was concentrated to afford the desired product (3.43 g), which was used in the next step without further purification. MS: 230.0. $^1$H NMR (400 MHz, CD$_3$OD) δ ppm 7.82 (d, J=5.5 Hz, 1H), 7.66 (d, J=5.6 Hz, 1H), 4.23 (q, J=7.1, Hz, 2H), 3.86 (s, 3H), 1.32 (t, J=7.1 Hz, 3H).

Step B: 3-Amino-1H-thieno[3,2-d]pyrimidine-2,4-dione. To a solution of 3-ethoxycarbonylamino-thiophene-2-carboxylic acid methyl ester (3.43 g, 15.0 mmol) in EtOH (100 mL) was added hydrazine monohydrate (7.98 mL, 164.6 mmol). After heating at 90° C. for 12 h, the mixture was filtered to afford a fine yellow powder (1.70 g), which was used in the next step without further purification. MS: 184.2. $^1$H NMR (400 MHz, CD$_3$OD) δ ppm 7.93 (d, J=5.3 Hz, 1H), 6.95 (d, J=5.3 Hz, 1H).

Step C: 1H-Thieno[3,2-d]pyrimidine-2,4-dione. To a solution of 3-amino-1H-thieno[3,2-d]pyrimidine-2,4-dione (1.70 g, 9.3 mmol) in a 1:1 mixture of acetic acid/H$_2$O (155 mL) was added sodium nitrite (1.92 g, 27.8 mmol) portion-wise. The reaction mixture was heated to 60° C. until the evolution of brown gas ceased (2 h). Acetic acid was removed under reduced pressure and the solution was cooled to 0° C. The resulting white solid was collected by filtration to afford 0.77 g of the desired product. MS: 167.3. $^1$H NMR (400 MHz, d$_6$-N,N-dimethylsulfoxide (d$_6$-DMSO)) δ ppm 11.40 (br s, 1H), 8.04 (d, J=5.2 Hz, 1H), 6.91 (d, J=5.3 Hz, 1H), 3.34 (br s, 1H).

Step D: 2,4-Dichloro-thieno[3,2-d]pyrimidine. To a solution of 1H-thieno[3,2-d]pyrimidine-2,4-dione (0.77 g, 4.6 mmol) in POCl$_3$ (2.70 mL) was added diethylaniline (0.29 mL, 1.8 mmol). After heating at 100° C. for 12 h in a sealed tube, the mixture was poured into ice water and the title compound was filtered from the solution as a brown solid (0.73 g). MS: No signal. $^1$H NMR (400 MHz, d$_6$-DMSO) δ ppm 8.71 (d, J=5.5 Hz, 1H), 7.75 (d, J=5.4 Hz, 1H).

Step E: 2-Chloro-4-(4-methyl-piperazin-1-yl)-thieno[3,2-d]pyrimidine. To a solution of 2,4-dichloro-thieno[3,2-d]pyrimidine (0.20 g, 1.0 mmol) in EtOH (3.2 mL) was added K$_2$CO$_3$ (0.31 g, 2.2 mmol) followed by N-methylpiperazine (0.13 mL, 1.2 mmol). After stirring at rt for 12 h, the mixture was filtered to afford 0.23 g of the desired product. MS: 269.0. $^1$H NMR (400 MHz, CD$_3$OD) δ ppm 8.06 (d, J=5.6 Hz, 1H), 7.27 (d, J=5.6 Hz, 1H), 4.05-4.00 (m, 4H), 2.62-2.56 (m, 4H), 2.36 (s, 3H).

Step F: 4-(4-Methyl-piperazin-1-yl)-thieno[3,2-d]pyrimidin-2-ylamine. To a solution of 2-chloro-4-(4-methyl-piperazin-1-yl)-thieno[3,2-d]pyrimidine (0.11 g, 0.4 mmol) in pyridine (0.34 mL) in a microwave vial was added 4-methoxybenzylamine (0.55 mL, 4.2 mmol). The reaction mixture was heated to 200° C. in the microwave for 1 h, after which pyridine was removed under reduced pressure. The resultant residue was purified by FCC (2 M NH$_3$ in MeOH/CH$_2$Cl$_2$) to yield (4-methoxy-benzyl)-[4-(4-methyl-piperazin-1-yl)-thieno[3,2-d]pyrimidin-2-yl]-amine. The intermediate was then dissolved in trifluoroacetic acid (2.5 mL) and heated at 60° C. for 1.5 h. After concentrating, the residue was purified by reverse-phase chromatography (acidic conditions) to afford the desired product as a TFA salt (30 mg). MS: 250.1. $^1$H NMR (400 MHz, CD$_3$OD) δ ppm 8.26 (d, J=5.6 Hz, 1H), 7.30 (d, J=5.6 Hz, 1H), 4.65-4.12 (m, 4H), 3.60-3.41 (m, 4H), 2.98 (s, 3H).

Example 2

4-(4-Methyl-piperazin-1-yl)-6,7,8,9-tetrahydro-benzo[4,5]thieno[3,2-d]pyrimidin-2-ylamine

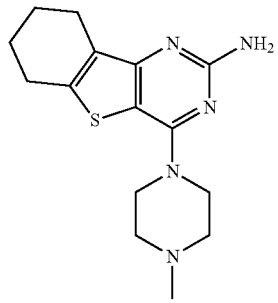

Step A: 2-Chloro-cyclohex-1-enecarbonitrile. To a stirring solution of POCl$_3$ (15.20 mL, 163 mmol) at 0° C. was added DMF (13.40 mL, 173 mmol) drop-wise. Monitoring internal temperature, cyclohexanone (10.60 mL, 102 mmol) was slowly added, keeping the temperature between 35 and 40° C. Upon complete addition, the reaction was heated to 50° C. and hydroxylamine hydrochloride (40 g, 576 mmol) was added in eight portions, cooling when necessary to control the exothermic reaction. Upon completing this addition, ice was added to the reaction, followed by water (400 mL), and the mixture resumed stirring for 1 h. Filtration afforded the desired product as a brown solid (8.8 g). Some substrates may require an aqueous work-up/extraction procedure if water solubility is too high. EtOAc is generally a good solvent for this extraction. MS: No signal. $^1$H NMR (400 MHz, CDCl$_3$ δ ppm 2.47-2.36 (m, 2H), 2.34-2.25 (m, 2H), 1.78-1.67 (m, 1H), 1.67-1.58 (m, 1H).

Step B: 3-Amino-4,5,6,7-tetrahydro-benzo[b]thiophene-2-carboxylic acid ethyl ester. A 250 mL flask was charged with 2-chloro-cyclohex-1-enecarbonitrile (3.0 g, 21 mmol) in a 6:1 mixture of EtOH/THF (42 mL), K$_2$CO$_3$ (2.9 g, 21 mmol), and mercapto-acetic acid ethyl ester (3.5 mL, 32 mmol), after which it was fitted with a reflux condenser under N$_2$ atmosphere and heated to 90° C. for 24 h. The mixture was filtered through a pad of diatomaceous earth, such as Celite®, rinsing thoroughly with MeOH (400 mL). After concentration, the title compound was purified by FCC (60% ethyl acetate (EtOAc)/hexanes) to give an amber-colored oil (4.8 g). MS: 226.1. $^1$H NMR (400 MHz, CDCl$_3$) δ ppm 5.35 (s, 2H), 2.71-2.64 (m, 2H), 2.36-2.26 (m, 2H), 1.87-1.77 (m, 4H), 1.33 (t, J=7.1 Hz, 3H).

Step C: 2-Amino-6,7,8,9-tetrahydro-1H-benzo[4,5]thieno[3,2-d]pyrimidin-4-one.

A 48 mL sealed tube was charged with 3-amino-4,5,6,7-tetrahydro-benzo[b]thiophene-2-carboxylic acid ethyl ester (2.8 g, 12.3 mmol), chloroformamidine hydrochloride (2.0 g, 17.2 mmol), and diethylene glycol dimethyl ether (24.6 mL). The tube was sealed and heated to 160° C. for 12 h with vigorous stirring. Filtration afforded the desired compound as a beige solid (2.6 g). MS: No signal. $^1$H NMR (400 MHz, d$_6$-DMSO) δ ppm 2.84-2.73 (m, 2H), 2.58-2.51 (m, 2H), 1.89-1.70 (m, 4H).

Step D: 4-Chloro-6,7,8,9-tetrahydro-benzo[4,5]thieno[3,2-d]pyrimidin-2-ylamine.

In a 15 mL flask, 2-amino-6,7,8,9-tetrahydro-1H-benzo[4,5]thieno[3,2-d]pyrimidin-4-one (0.2 g, 0.9 mmol) and tetraethyl ammonium chloride (0.3 g, 1.8 mmol) were dried under vacuum at 100° C. for 12 h. Addition of acetonitrile (1.80 mL), dimethylaniline (0.12 mL, 0.9 mmol) and POCl$_3$ (0.50 mL, 5.42 mmol) followed, and the reaction mixture was heated to 110° C. for 15 min. The solution was concentrated and ice was added along with CHCl$_3$ (5 mL). The aqueous layer pH was adjusted to pH=7 with saturated (satd.) aq. NaHCO$_3$ and extraction from that layer proceeded with CHCl$_3$ (3×20 mL). The combined organic layers were dried (Na$_2$SO$_4$) and concentrated. The resultant residue was purified by FCC (50% EtOAc/hexanes) to afford the desired product as a pale yellow solid (88 mg). Certain substrates were found to be unstable at higher temperatures, in which case prolonged heating at lower temperature (in a range such as from about 50° C. to about 60° C.) sufficed. MS: 240.0. $^1$H NMR (400 MHz, CDCl$_3$) δ ppm 5.08 (s, 2H), 2.90-2.83 (m, 2H), 2.74-2.67 (m, 2H), 1.98-1.91 (m, 2H), 1.91-1.83 (m, 2H).

Step E: 4-(4-Methyl-piperazin-1-yl)-6,7,8,9-tetrahydro-benzo[4,5]thieno[3,2-d]pyrimidin-2-ylamine. To a solution of 4-chloro-6,7,8,9-tetrahydro-benzo[4,5]thieno[3,2-d]pyrimidin-2-ylamine (0.09 mg, 0.37 mmol) in EtOH (3.7 mL) was added K$_2$CO$_3$ (0.12 g, 0.84 mmol) followed by N-methylpiperazine (0.05 mL, 0.44 mmol). After stirring at rt for 22 h, EtOH was removed under reduced pressure and the mixture was dissolved in CH$_2$Cl$_2$ (5 mL) and poured over H$_2$O (10 mL). The aqueous layer was extracted with CH$_2$Cl$_2$ (3×10 mL). The combined organic layers were washed with brine, such as with a satd. aq. NaCl, (30 mL), dried, for example with Na$_2$SO$_4$, and concentrated to afford the title compound (0.05 g) as a pale yellow solid. MS: 304.2. $^1$H NMR (400 MHz, CD$_3$OD) δ ppm 3.93-3.88 (m, 4H), 2.80 (t, J=6.0 Hz, 2H), 2.63 (t, J=6.1 Hz, 2H), 2.56-2.52 (m, 4H), 2.33 (s, 3H), 1.96-1.81 (m, 4H).

Example 3

4-piperazin-1-yl-6,7,8,9-tetrahydro-benzo[4,5]thieno[3,2-d]pyrimidin-2-ylamine

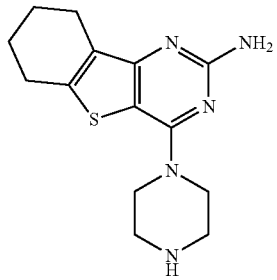 [SMILES: Nc1nc(N2CCNCC2)c2sc3c(c2n1)CCCC3]

To a solution of 4-(2-amino-6,7,8,9-tetrahydro-benzo[4,5]thieno[3,2-d]pyrimidin-4-yl)-piperazine-1-carboxylic acid (synthesized by the route described in Example 2, Steps A-D; 0.093 g, 0.5 mmol) in formic acid (3 mL) was added 6 N aq. HCl (0.5 mL, 3.0 mmol). After stirring at rt for 1 h, the reaction mixture was concentrated and purified by reverse-phase chromatography (acidic conditions) to afford the desired product as a TFA salt (0.009 g). MS: 290.1. $^1$H NMR (400 MHz, CD$_3$OD) δ ppm 3.92-3.81 (m, 4H), 2.92-2.87 (m, 4H), 2.82-2.75 (m, 2H), 2.62 (t, J=6.0 Hz, 2H), 1.96-1.80 (m, 4H).

Example 4

4-[(3aR,6aR)-Hexahydropyrrolo[3,4-b]pyrrol-5(1H)-yl]-6,7,8,9-tetrahydro[1]benzothieno[3,2-d]pyrimidin-2-amine

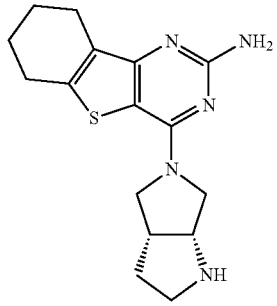

A 90 mL parr shaker was charged with 4-[1-(1-phenyl-ethyl)-hexahydro-pyrrolo[3,4-b]pyrrol-5-yl]-6,7,8,9-tetrahydro-benzo[4,5]thieno[3,2-d]pyrimidin-2-ylamine trifluoroacetate (synthesized by route described in Example 2, Steps A-E; 0.20 g, 0.4 mmol), Pd(OH)$_2$/C (30% by weight, 0.06 g) and EtOH (3.7 mL). The mixture was submitted to 60 psi H$_2$ with shaking for 36 h. The reaction mixture was filtered through a pad of diatomaceous earth and concentrated to afford the desired compound (0.12 g). MS: 316.1. $^1$H NMR (400 MHz, CD$_3$OD) δ ppm 4.47-4.29 (m, 2H), 4.25-4.07 (m, 2H), 3.91-3.80 (m, 1H), 3.54-3.38 (m, 3H), 2.97-2.84 (m, 2H), 2.69-2.61 (m, 2H), 2.41-2.29 (m, 1H), 2.14-2.02 (m, 1H), 2.02-1.86 (m, 4H).

Example 5

4-(4-Methyl-piperazin-1-yl)-6,7,8,9-tetrahydro-benzo[4,5]furo[3,2-d]pyrimidin-2-ylamine

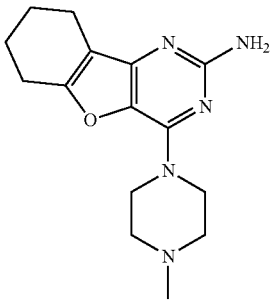 [SMILES: CN1CCN(c2nc(N)nc3c4c(oc23)CCCC4)CC1]

Step A: 3-Amino-4,5,6,7-tetrahydro-benzofuran-2-carboxylic acid ethyl ester. A solution of resin bound PPh$_3$ (Polymer Laboratories, 1.48 mmol/g, 150-300 μM; 3.8 g, 5.7 mmol) in THF (35 mL) at 0° C. was treated with diethyl azodicarboxylate (40% wt. in hexane; 2.60 mL, 5.7 mmol), ethyl glycolate (0.54 mL, 5.7 mmol) and a solution of 2-oxo-cyclohexanecarbonitrile (0.5 g, 4.1 mmol) in THF (10 mL). The reaction mixture warmed to rt over 12 h. Filtration and concentration afforded the uncyclized intermediate, which was dissolved in THF (25 mL) and added drop-wise to a slurry of sodium hydride (95%; 0.29 g, 11.4 mmol) in THF (10 mL) at 0° C. The reaction mixture was heated to 40° C. for 12 h. The reaction was quenched with satd. aq. NH$_4$Cl (5 mL) and the mixture was extracted with EtOAc (3×50 mL). The combined organic layers were dried (by using, for example, Na$_2$SO$_4$) and concentrated. Purification by FCC (50% EtOAc/hexanes) afforded the desired product as a pale yellow solid (0.36 g). MS: 210.2. $^1$H NMR (400 MHz, CD$_3$OD) δ ppm 4.26 (q, J=7.1, Hz, 2H), 2.55-2.47 (m, 2H), 2.35-2.28 (m, 2H), 1.90-1.79 (m, 2H), 1.79-1.71 (m, 2H), 1.33 (t, J=7.1, Hz, 3H).

Step B: 2-Amino-6,7,8,9-tetrahydro-1H-benzo[4,5]furo[3,2-d]pyrimidin-4-one.

The title compound was synthesized by the route described in Example 2, Step B. MS: No signal. $^1$H NMR (400 MHz, d$_6$-DMSO) δ ppm 2.68 (t, J=6.0, Hz, 2H), 2.46 (t, J=5.8, Hz, 2H), 1.88-1.77 (m, 2H), 1.77-1.68 (m, 2H).

Step C: 4-Chloro-6,7,8,9-tetrahydro-benzo[4,5]furo[3,2-d]pyrimidin-2-ylamine.

The title compound was synthesized by the route described in Example 2, Step C, substituting diethylaniline for dimethylaniline. MS: 224.1. $^1$H NMR (400 MHz, CD$_3$OD) δ ppm 2.79-2.72 (m, 2H), 2.60-2.54 (m, 2H), 2.01-1.92 (m, 2H), 1.88-1.80 (m, 2H).

Step D: 4-(4-Methyl-piperazin-1-yl)-6,7,8,9-tetrahydro-benzo[4,5]furo[3,2-d]pyrimidin-2-ylamine. The title compound was synthesized by the route described in Example 2, Step D. Purification by reverse-phase HPLC (acidic conditions) provided the title compound as the TFA salt. MS: 288.2. $^1$H NMR (500 MHz, CD$_3$OD) δ ppm 3.85-3.34 (m, 8H), 2.99 (s, 3H), 2.80 (t, J=6.2 Hz, 2H), 2.61 (t, J=6.0 Hz, 2H), 2.03-1.92 (m, 2H), 1.91-1.84 (m, 2H).

Example 6

4-piperazin-1-yl-6,7,8,9-tetrahydro-benzo[4,5]furo[3,2-d]pyrimidin-2-ylamine

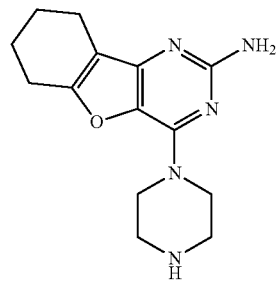

The title compound was prepared from 4-(2-amino-6,7,8,9-tetrahydro-benzo[4,5]furo[3,2-d]pyrimidin-4-yl)-piperazine-1-carboxylic acid tert-butyl ester (synthesized by the route described in Example 5, Steps A-D) by using the conditions described in Example 3. MS: 274.2. $^1$H NMR (500 MHz, CD$_3$OD) δ ppm 4.46-4.26 (m, 4H), 3.48-3.37 (m, 4H), 2.80 (t, J=6.2 Hz, 2H), 2.61 (t, J=6.0 Hz, 2H), 2.03-1.92 (m, 2H), 1.92-1.82 (m, 2H).

Example 7

4-[(3aR,6aR)-Hexahydropyrrolo[3,4-b]pyrrol-5(1H)-yl]-6,7,8,9-tetrahydro[1]benzofuro[3,2-d]pyrimidin-2-amine

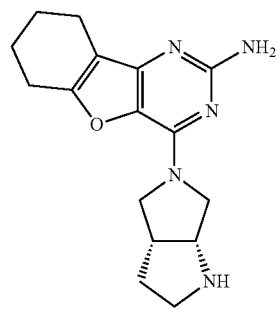 [SMILES: Nc1nc(N2C[C@H]3CCN[C@H]3C2)c2oc3c(c2n1)CCCC3]

The title compound was prepared from 4-[1-(1-phenyl-ethyl)-hexahydro-pyrrolo[3,4-b]pyrrol-5-yl]-6,7,8,9-tetrahydro-benzo[4,5]furo[3,2-d]pyrimidin-2-ylamine (synthesized by the route described in Example 5, Steps A-D) using the conditions described in Example 4. MS: 300.2. $^1$H NMR (400 MHz, CD$_3$OD) δ ppm 4.54-3.98 (m, 3H), 3.97-3.58 (m, 2H), 3.39-3.04 (m, 3H), 2.59 (t, J=5.7 Hz, 2H), 2.40 (t, J=5.7 Hz, 2H), 2.28-2.12 (m, 1H), 2.01-1.83 (m, 1H), 1.83-1.73 (m, 2H), 1.73-1.62 (m, 2H).

Example 8

4-(4-Methyl-piperazin-1-yl)-6,7,8,9-tetrahydro-benzo[4,5]furo[3,2-d]pyrimidine

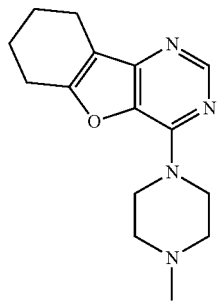 [SMILES: CN1CCN(c2ncnc3c4c(sc23)CCCC4)CC1]

Step A: 6,7,8,9-Tetrahydro-benzo[4,5]furo[3,2-d]pyrimidin-4-ol. A 15 mL flask was charged with 3-amino-4,5,6,7-tetrahydro-benzo[b]thiophene-2-carboxylic acid ethyl ester (synthesized by the route described in Example 5, Step A; 0.50 g, 2.4 mmol), formamide (4.8 mL), and KO$^t$Bu (95%; 0.56 g, 4.8 mmol) under $N_2$. After heating at 110° C. for 12 h, the mixture was poured over cold satd. aq. $NH_4Cl$ (10 mL). Filtration afforded the desired product (0.31 g). MS: No signal. $^1$H NMR (400 MHz, $d_6$-DMSO) δ ppm 8.00 (s, 1H), 2.74-2.69 (m, 2H), 2.56-2.51 (m, 2H), 1.92-1.81 (m, 2H), 1.79-1.69 (m, 2H).

Step B: 4-Chloro-6,7,8,9-tetrahydro-benzo[4,5]furo[3,2-d]pyrimidine. A 15 mL sealed tube was charged with 6,7,8,9-tetrahydro-benzo[4,5]furo[3,2-d]pyrimidin-4-ol (0.31 g, 1.6 mmol) and $POCl_3$ (3 mL), sealed, and heated to 110° C. After 30 min, $POCl_3$ was removed under reduced pressure and the resultant residue was purified by FCC (40% EtOAc/hexanes) to afford the desired product as a white solid (0.27 g). MS: 189.0 (negative mode). $^1$H NMR (400 MHz, $d_6$-DMSO) δ ppm 8.00 (s, 1H), 2.74-2.67 (m, 2H), 2.57-2.51 (m, 2H), 1.90-1.82 (m, 2H), 1.80-1.70 (m, 2H).

Step C: 4-(4-Methyl-piperazin-1-yl)-6,7,8,9-tetrahydro-benzo[4,5]furo[3,2-d]pyrimidine. The title compound was prepared by subjecting 4-chloro-6,7,8,9-tetrahydro-benzo[4,5]furo[3,2-d]pyrimidine to the conditions described in Example 2, Step E. MS: 273.1. $^1$H NMR (400 MHz, $CD_3OD$) δ ppm 8.27 (s, 1H), 4.09-4.01 (m, 4H), 2.80-2.73 (m, 2H), 2.67-2.60 (m, 2H), 2.59-2.55 (m, 4H), 2.35 (s, 3H), 2.03-1.92 (m, 2H), 1.90-1.81 (m, 2H).

Example 9

4-piperazin-1-yl-6,7,8,9-tetrahydro-benzo[4,5]furo[3,2-d]pyrimidine

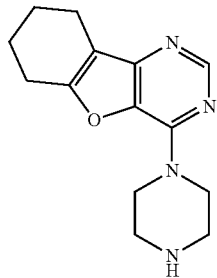

The title compound was prepared from 4-(6,7,8,9-tetrahydro-benzo[4,5]furo[3,2-d]pyrimidin-4-yl)-piperazine-1-carboxylic acid tert-butyl ester (prepared by the synthesis described in Example 8) according to the deprotection methods described in Example 3. MS: 259.1. $^1$H NMR (400 MHz, $CD_3OD$) δ ppm 8.27 (s, 1H), 4.03-3.98 (m, 4H), 2.99-2.89 (m, 4H), 2.80-2.73 (m, 2H), 2.66-2.59 (m, 2H), 2.02-1.93 (m, 2H), 1.89-1.81 (m, 2H).

Example 10

4-(4-Methyl-piperazin-1-yl)-6,7,8,9-tetrahydro-benzo[4,5]thieno[3,2-d]pyrimidine

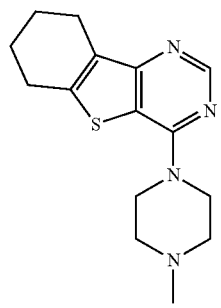

The title compound was prepared from 3-amino-4,5,6,7-tetrahydro-benzo[b]thiophene-2-carboxylic acid ethyl ester (prepared by the synthesis described in Example 2, Steps A-B) using the conditions described in Example 8, Steps A-C. MS: 289.1. $^1$H NMR (400 MHz, $CD_3OD$) δ ppm 8.41 (s, 1H), 4.02-3.95 (m, 4H), 2.86 (t, J=6.0 Hz, 2H), 2.73 (t, J=6.1 Hz, 2H), 2.61-2.53 (m, 4H), 2.34 (s, 3H), 1.99-1.84 (m, 4H).

Example 11

4-piperazin-1-yl-6,7,8,9-tetrahydro-benzo[4,5]thieno[3,2-d]pyrimidine

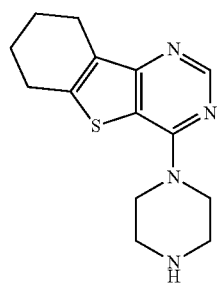 [SMILES: c1nc(N2CCNCC2)c2sc3c(c2n1)CCCC3]

The title compound was prepared from 4-(6,7,8,9-tetrahydro-benzo[4,5]thieno[3,2-d]pyrimidin-4-yl)-piperazine-1-carboxylic acid tert-butyl ester (prepared by the synthesis described in Example 10) according to the deprotection methods described in Example 3. MS: 275.1. $^1$H NMR (400 MHz, $CD_3OD$) δ ppm 8.39 (s, 1H), 4.01-3.90 (m, 4H), 2.99-2.90 (m, 4H), 2.85 (t, J=5.9 Hz, 2H), 2.76-2.69 (m, 2H), 2.01-1.82 (m, 4H)

The compounds in Examples 12-151 were prepared using methods analogous to those described in the preceding examples.

| Structure | Chemical Name, MS Data, NMR Data |
|---|---|
| | Example 12<br>7-Methyl-4-[(3R)-3-(methylamino)pyrrolidin-1-yl]thieno[3,2-d]pyrimidin-2-amine<br>MS: 264.1<br>$^1$H NMR (400 MHz, CD$_3$OD) δ ppm 7.43 (d, J = 1.1 Hz, 1H), 4.06-3.92 (m, 2H), 3.91-3.78 (m, 1H), 3.64 (dd, J = 10.8, 4.9 Hz, 1H), 3.40-3.33 (m, 1H), 2.42 (s, 3H), 2.29-2.19 (m, 4H), 1.97-1.86 (m, 1H) |
| | Example 13<br>7-Methyl-4-(4-methyl-piperazin-1-yl)thieno-amine trifluoroacetic acid salt<br>MS: 264.1<br>$^1$H NMR (400 MHz, CD$_3$OD) δ ppm 7.91 (d, J = 1.1 Hz, 1H), 4.74-4.00 (m, 4H), 3.61-3.39 (m, 4H), 2.98 (s, 3H), 2.39 (d, J = 1.0 Hz, 3H) |
| | Example 14<br>7-Bromo-4-(3R)-3-(methyl-amino)pyrrolidin-1-yl-d]pyrimidin-2-amine trifluoroacetic acid salt<br>MS: 328.0<br>$^1$H NMR (400 MHz, CD$_3$OD) δ ppm 8.34 (s, 1H), 4.35-4.08 (m, 4H), 4.08-3.95 (m, 1H), 2.82 (s, 3H), 2.75-2.58 (m, 1H), 2.57-2.41 (m, 1H) |
| | Example 15<br>6-tert-Butyl-4-(4-methyl-piperazin-1-yl)thieno[3,2-d]pyrimidin-2-amine trifluoroacetic acid salt<br>MS: 306.2<br>$^1$H NMR (400 MHz, CD$_3$OD) δ ppm 7.12 (s, 1H), 4.85-3.85 (m, 4H), 3.61-3.40 (m, 4H), 2.98 (s, 3H), 1.48 (s, 9H) |
| | Example 16<br>6-tert-Butyl-4-[(3R)-3-(methylamino)pyrrolidin-1-yl-d]pyrimidin-2-amine trifluoroacetic acid salt<br>MS: 306.2<br>$^1$H NMR (400 MHz, CD$_3$OD) δ ppm 7.08 (s, 1H), 4.52-3.85 (m, 5H), 2.81 (s, 3H), 2.73-2.22 (m, 2H), 1.47 (s, 9H) |
| | Example 17<br>6-tert-Butyl-4-piperazin-1-ylthieno[3,2-d]pyrimidin-2-amine trifluoroacetic acid salt<br>MS: 292.2<br>$^1$H NMR (400 MHz, CD$_3$OD) δ ppm 7.03 (s, 1H), 4.27-4.22 (m, 4H), 3.37-3.33 (m, 4H), 1.38 (s, 9H) |
| | Example 18<br>4-[(3R)-3-Aminopyrrolidin-1-yl]-6-tert-butylthieno[3,2-d]pyrimidin-2-amine trifluoroacetic acid salt<br>MS: 292.2<br>$^1$H NMR (400 MHz, CD$_3$OD) δ ppm 7.12-7.07 (m, 1H), 4.47-3.92 (m, 5H), 2.70-2.13 (m, 2H), 1.47 (s, 9H) |
| | Example 19<br>6-tert-Butyl-4-(octahydro-6H-pyrrolo[3,4-b]pyridin-6-yl)thieno[3,2-d]pyrimidin-2-amine trifluoroacetic acid salt<br>MS: 332.2<br>$^1$H NMR (400 MHz, CD$_3$OD) δ ppm 7.08 (s, 1H), 4.36-4.28 (m, 1H), 4.27-4.18 (m, 1H), 4.15-4.05 (m, 1H), 4.04-3.94 (m, 2H), 3.44-3.35 (m, 1H), 3.15-2.78 (m, 2H), 2.07-1.76 (m, 4H), 1.47 (s, 9H) |
| | Example 20<br>4-[(4aR,7aR)-Octahydro-6H-pyrrolo[3,4-b]pyridin-6-yl]-6,7,8,9-tetra-hydro[1]benzofuro[3,2-d]pyrimidin-2-amine trifluoroacetic acid salt<br>MS: 314.2<br>$^1$H NMR (500 MHz, CD$_3$OD) δ ppm 4.42-4.13 (m, 2H), 4.11-4.02 (m, 1H), 4.01-3.95 (m, 2H), 3.45-3.35 (m, 1H), 3.17-3.03 (m, 1H), 3.02-2.82 (m, 1H), 2.81-2.73 (m, 2H), 2.60 (t, J = 5.34 Hz, 2H), 2.05-1.92 (m, 4H), 1.92-1.79 (m, 4H) |
| | Example 21<br>4-[(3R)-3-(Methyl-amino)pyrrolidin-1-yl]-6,7,8,9-tetrahydro[1]benzo-furo[3,2-d]pyrimidin-2-amine trifluoro acid salt<br>MS: 288.1<br>$^1$H NMR (500 MHz, CD$_3$OD) δ ppm 4.44-4.11 (m, 2H), 4.11-3.82 (m, 3H), 2.86-2.80 (m, 3H), 2.80-2.74 (m, 2H), 2.64-2.56 (m, 2H), 2.55-2.22 (m, 2H), 2.03-1.91 (m, 2H), 1.91-1.82 (m, 2H) |

| Structure | Chemical Name, MS Data, NMR Data |
|---|---|
| | Example 22<br>4-(1,4-Diazepan-1-yl)-6,7,8,9-tetrahydro[1]benzofuro[3,2-d]pyrimidin-2-amine trifluoroacetic acid salt<br>MS: 288.2<br>¹H NMR (400 MHz, CD₃OD) δ ppm 4.43-4.32 (m, 1H), 4.29-4.17 (m, 2H), 4.14-4.04 (m, 1H), 3.61-3.52 (m, 1H), 3.52-3.45 (m, 1H), 3.45-3.35 (m, 2H), 2.77 (t, J = 6.2 Hz, 2H), 2.59 (t, J = 6.0 Hz, 2H), 2.33-2.14 (m, 2H), 2.04-1.91 (m, 2H), 1.91-1.81 (m, 2H) |
| | Example 23<br>4-(3-Aminoazetidin-1-yl)-6,7,8,9-tetrahydro[1]benzofuro[3,s-d]pyrimidin-2-amine trifluoroacetic acid salt<br>MS: 260.1<br>¹H NMR (400 MHz, CD₃OD) δ ppm 5.01-4.94 (m, 1H), 4.76-4.51 (m, 2H), 4.46-4.24 (m, 2H), 2.75 (t, J = 6.1 Hz, 2H), 2.58 (t, J = 5.9 Hz, 2H), 2.03-1.91 (m, 2H), 1.90-1.81 (m, 2H) |
| | Example 24<br>4-[(3R)-3-Aminopyrrolidin-1-yl-6,7,8,9-tetrahydro[1]benzofuro[3,2-d]pyrimidin-2-amine trifluoroacetic acid salt<br>MS: 274.2<br>¹H NMR (400 MHz, CD₃OD) δ ppm 4.39-3.87 (m, 5H), 2.81-2.73 (m, 2H), 2.58 (t, J = 5.9 Hz, 2H), 2.56-2.39 (m, 1H), 2.37-2.12 (m, 1H), 2.04-1.91 (m, 2H), 1.91-1.81 (m, 2H) |
| | Example 25<br>N4-(2-Aminoethyl)-6,7,8,9-tetrahydro[1]benzofuro[3,2-d]pyrimidine-2,4-diamine trifluoroacetic acid salt<br>MS: 248.2<br>¹H NMR (400 MHz, CD₃OD) δ ppm 3.82-3.78 (m, 2H), 3.25-3.21 (m, 2H), 2.75-2.70 (m, 2H), 2.56 (t, J = 5.9 Hz, 2H), 2.00-1.89 (m, 2H), 1.89-1.79 (m, 2H) |
| | Example 26<br>4-(3,8-Diazabicyclo[3.2.1]oct-3-yl)-6,7,8,9-tetrahydro[1]benzofuro[3,2-d]pyrimidin-2-amine<br>MS: 300.2<br>¹H NMR (400 MHz, CD₃OD) δ ppm 4.53-4.46 (m, 1H), 3.61-3.50 (m, 1H), 3.25-3.14 (m, 1H), 2.67 (t, J = 6.2 Hz, 2H), 2.52 (t, J = 6.0 Hz, 2H), 2.00-1.88 (m, 2H), 1.88-1.72 (m, 6H) |
| | Example 27<br>N-(6,7,8,9-Tetrahydro[1]benzofuro[3,2-d]pyrimidin-4-yl)ethane-1,2-diamine<br>MS: 233.1<br>¹H NMR (400 MHz, CD₃OD) δ ppm 8.25 (s, 1H), 3.66 (t, J = 6.2 Hz, 2H), 2.95 (t, J = 6.2 Hz, 2H), 2.81-2.73 (m, 2H), 2.67-2.59 (m, 2H), 2.02-1.91 (m, 2H), 1.90-1.81 (m, 2H) |
| | Example 28<br>(3R)-N-Methyl-1-(6,7,8,9-tetrahydro[1]benzofuro[3,2-d]pyrimidin-4-yl)pyrrolidin-3-amine<br>MS: 273.1<br>¹H NMR (400 MHz, CD₃OD) δ ppm 8.21 (s, 1H), 4.18-3.61 (m, 4H), 3.48-3.35 (m, 1H), 2.85-2.71 (m, 2H), 2.68-2.59 (m, 2H), 2.43 (s, 3H), 2.32-2.20 (m, 1H), 2.07-1.91 (m, 3H), 1.90-1.81 (m, 2H) |
| | Example 29<br>N-(6,7,8,9 - Tetrahydro[1]benzothieno[3,2-d]pyrimidin-4-yl)ethane-1,2-diamine<br>MS: 249.1<br>¹H NMR (400 MHz, CD₃OD) δ ppm 8.37 (s, 1H), 3.65 (t, J = 6.3 Hz, 2H), 2.93 (t, J = 6.3 Hz, 2H), 2.90-2.83 (m, 2H), 2.77-2.69 (m, 2H), 2.01-1.80 (m, 4H) |
| | Example 30<br>(3R)-N-Methyl-1-(6,7,8,9-tetrahydro[1]benzothieno[3,2-d]pyrimidin-4-yl)pyrrolidin-3-amine<br>MS: 289.0<br>¹H NMR (400 MHz, CD₃OD) δ ppm 8.29 (s, 1H), 4.13-3.94 (m, 2H), 3.94-3.79 (m, 1H), 3.74-3.61 (m, 1H), 3.43-3.34 (m, 1H), 2.86 (t, J = 5.9 Hz, 2H), 2.72 (t, J = 5.9 Hz, 2H), 2.43 (s, 3H), 2.32-2.20 (m, 1H), 2.01-1.83 (m, 5H) |
| | Example 31<br>4-[(3R)-3-(Methylamino)pyrrolidin-1-yl]-6,7,8,9-tetrahydro[1]benzothieno[3,2-d]pyrimidin-2-amine<br>MS: 304.1<br>¹H NMR (400 MHz, CD₃OD) δ ppm 4.02-3.91 (m, 2H), 3.87-3.77 (m, 1H), 3.62 (dd, J = 10.9, 5.0 Hz, 1H), 3.37-3.33 (m, 1H), 2.80 (t, J = 5.9 Hz, 2H), 2.62 (t, J = 6.0 Hz, 2H), 2.42 (s, 3H), 2.28-2.17 (m, 1H), 1.96-1.81 (m, 5H) |

| Structure | Chemical Name, MS Data, NMR Data |
|---|---|
| | Example 32<br>4-[(4aR,7aR)-Octahydro-6H-pyrrolo[3,4-b]pyridin-6-yl]-6,7,8,9-tetrahydro[1]benzothieno[3,2-,d]pyrimidin-2-amine<br>MS: 330.1<br>$^1$H NMR (400 MHz, CD$_3$OD) δ ppm 3.93-3.69 (m, 4H), 3.40-3.35 (m, 1H), 2.95-2.88 (m, 1H), 2.78 (t, J = 5.8 Hz, 1H), 2.66-2.57 (m, 3H), 2.45-2.31 (m, 1H), 1.96-1.82 (m, 4H), 1.82-1.75 (m, 2H), 1.71-1.57 (m, 1H), 1.54-1.45 (m, 1H) |
| | Example 33<br>4-Hexahydropyrrolo[3 4-c]pyrrol-2(1H)-yl]6,7,8,9-tetrahydro[1]benzothieno[3,2-d]pyrimidin-2-amine<br>MS: 316.1<br>$^1$H NMR (400 MHz, CD$_3$OD) δ ppm 4.05-3.96 (m, 2H), 3.71 (dd, J = 11.1, 3.4 Hz, 2H), 3.12 (dd, J = 11.4, 7.2 Hz, 1H), 3.02-2.93 (m, 2H), 2.85-2.74 (m, 4H), 2.62 (t, J = 5.5 Hz, 2H), 1.95-1.82 (m, 4H) |
| | Example 34<br>4-[(3S)-3-Aminopiperidin-1-yl]-6,7,8,9-tetrahydro[1]benzothieno[3,2-d]pyrimidin-2-amine<br>MS: 304.1<br>$^1$H NMR (400 MHz, CD$_3$OD) δ ppm 4.64-4.57 (m, 1H), 4.50-4.42 (m, 1H), 3.19-3.10 (m, 1H), 2.94-2.86 (m, 1H), 2.84-2.76 (m, 3H), 2.65-2.60 (m, 2H), 2.07-1.99 (m, 1H), 1.96-1.77 (m, 5H), 1.65-1.52 (m, 1H), 1.48-1.35 (m, 1H) |
| | Example 35<br>4-[(1S,4S)-2,5-Diazabicyclo[2.2.1-2-yl]hept-2-yl]-6,7,8,9-tetrahydro[1]benzothieno[3,2-d]pyrimidin-2-amine<br>MS: 302.1<br>$^1$H NMR (400 MHz, CD$_3$OD) δ ppm 5.07-4.99 (m, 1H), 4.15 (dd, J = 21.0, 8.8 Hz, 1H), 3.94-3.60 (m, 2H), 3.36-3.33 (m, 2H), 3.12-2.97 (m, 1H), 2.86-2.72 (m, 2H), 2.65-2.57 (m, 2H), 2.05-1.96 (m, 1H), 1.96-1.77 (m, 4H) |
| | Example 36<br>4-[(1R,4R)-2,5-Diazabicyclo[2.2.1]hept-2-yl]-6,7,8,9-tetrahydro[1]benzothieno[3,2-d]pyrimidin-2-amine<br>MS: 302.1<br>$^1$H NMR (400 MHz, CD$_3$OD) δ ppm 5.07-4.99 (m, 1H), 4.15 (dd, J = 20.7, 8.8 Hz, 1H), 3.93-3.63 (m, 2H), 3.37-3.33 (m, 2H), 3.14-2.99 (m, 1H), 2.84-2.73 (m, 2H), 2.61 (t, J = 5.9 Hz, 2H), 2.05-1.97 (m, 1H), 1.96-1.79 (m, 4H) |
| | Example 37<br>4-(1,4-Diazepan-1-yl)-6,7,8,9-tetrahydro[1]benzothieno[3,2-d]pyrimidin-2-amine hydrochloric acid salt<br>MS: 304.1<br>$^1$H NMR (400 MHz, (CD3)2OS) δ ppm 4.19-4.09 (m, 1H), 4.08-4.02 (m, 1H), 4.00-3.90 (m, 1H), 3.21-3.14 (m, 3H), 2.82-2.72 (m, 3H), 2.60-2.53 (m, 2H), 2.17-2.06 (m, 2H), 1.91-1.71 (m, 5H) |
| | Example 38<br>(3S,4S)-1-(2-Amino-6,7,8,9-tetrahydro[1]benzothieno[3,2-d]pyrimidin-4-yl)-4-(methylamino)pyrrolidin-3-of trifluoroacetic acid salt<br>MS: 320.2<br>1H NMR (400 MHz, CD$_3$OD) δ ppm 4.77-4.56 (m, 1H), 4.48-4.18 (m, 2H), 4.16-4.00 (m, 1H), 3.99-3.84 (m, 1H), 3.82-3.70 (m, 1H), 2.92 (t, J = 5.0 Hz, 2H), 2.86 (s, 3H), 2.66 (t, J = 5.2 Hz, 2H), 2.00-1.88 (m, 4H) |
| | Example 39<br>4-[(3R)-3-(Dimethylamino)pyrrolidin-1-yl]-6,7,8,9-tetrahydro[1]benzothieno[3,2-d]pyrimidin-2-amine trifluoroacetic acid salt<br>MS: 318.2<br>$^1$H NMR (400 MHz, CD$_3$OD) δ ppm 4.48-4.17 (m, 2H), 4.15-3.92 (m, 3H), 2.99 (s, 6H), 2.95-2.89 (m, 2H), 2.76-2.54 (m, 3H), 2.53-2.29 (m, 1H), 2.03-1.86 (m, 4H) |
| | Example 40<br>4-[(3R)-3-(Ethylamino)pyrrolidin-1-yl]-6,7,8,9-tetrahydro[1]benzothieno[3,2-d]pyrimidin-2-amine trifluoroacetic acid salt<br>MS: 318.2<br>$^1$H NMR (400 MHz, CD$_3$OD) δ ppm 4.29-4.13 (m, 2H), 4.12-4.00 (m, 3H), 3.26-3.11 (m, 2H), 2.92 (t, J = 5.0 Hz, 2H), 2.66 (t, J = 5.1 Hz, 2H), 2.63-2.53 (m, 1H), 2.46-2.27 (m, 1H), 2.01-1.87 (m, 4H), 1.36 (t, J = 7.3 Hz, 3H) |

| Structure | Chemical Name, MS Data, NMR Data |
|---|---|
| | Example 41<br>4-[(3R)-3-(Amino-methyl)pyrrolidin-1-yl]-6,7,8,9-tetrahydro[1]benzo-thieno[3,2-d]pyrimidin-2-amine trifluoroacetic acid salt<br>MS: 304.2<br>1H NMR (400 MHz, CD$_3$OD) δ ppm 4.36-3.95 (m, 2H), 3.87-3.63 (m, 1H), 3.63-3.45 (m, 1H), 3.24-3.00 (m, 2H), 2.91 (t, J = 5.0 Hz, 2H), 2.84-2.70 (m, 1H), 2.65 (t, J = 5.0 Hz, 2H), 2.50-2.20 (m, 1H), 2.06-1.88 (m, 4H), 1.88-1.75 (m, 1H) |
| | Example 42<br>4-(3-Aminoazetidin-1-yl)-6,7,8,9-tetrahydro[1]benzo-thieno[3,2-d]pyrimidin-2-amine trifluoroacetic acid salt<br>MS: 276.1<br>$^1$H NMR (400 MHz, CD$_3$OD) δ ppm 4.86-4.64 (m, 2H), 4.63-4.38 (m, 2H), 4.38-4.29 (m, 1H), 2.96-2.88 (m, 2H), 2.71-2.62 (m, 2H), 2.01-1.87 (m, 4H) |
| | Example 43<br>8-Methyl-4-(4-methyl-piperazin-1-yl)-6,7,8,9-tetrahydro[1]benzo-thieno[3,2-d]pyrimidin-2-amine trifluoroacetic acid salt<br>MS: 318.2<br>$^1$H NMR (400 MHz, CD$_3$OD) δ ppm 4.64-3.99 (m, 3H), 3.67-3.35 (m, 4H), 3.05-2.89 (m, 5H), 2.84 (dd, J = 16.4, 5.1 Hz, 2H), 2.25-2.13 (m, 1H), 2.11-1.88 (m, 2H), 1.65-1.47 (m, 1H), 1.16 (d, J = 6.6 Hz, 3H) |
| | Example 44<br>8-Methyl-4-[(3R)-3-(methyl-amino)pyrrolidin-1-yl]-6,7,8,9-tetrahydro[1]benzo-thieno[3,2-d]pyrimidin-2-amine trifluoroacetic acid salt<br>MS: 318.1<br>1H NMR (400 MHz, CD$_3$OD) δ ppm 4.48-4.04 (m, 4H), 4.02-3.86 (m, 1H), 3.06-2.87 (m, 2H), 2.86-2.76 (m, 4H), 2.71-2.56 (m, 1H), 2.55-2.37 (m, 1H), 2.24-2.13 (m, 1H), 2.11-2.01 (m, 1H), 2.01-1.90 (m, 1H), 1.64-1.48 (m, 1H), 1.16 (d, J = 6.5 Hz, 3H) |
| | Example 45<br>8-Methyl-4-[(4aR,7aR)-octa-hydro-6H-pyrrolo-[3,4-b]pyridin-6-yl]-6,7,8,9-tetra-hydro[1]benzothieno[3,2-d]pyrimidin-2-amine trifluoroacetic acid salt<br>MS: 344.1<br>$^1$H NMR (400 MHz, CD$_3$OD) δ ppm 4.40-4.17 (m, 2H), 4.15-3.88 (m, 3H), 3.45-3.36 (m, 1H), 3.17-2.88 (m, 4H), 2.82 (dd, J = 16.0, 5.0 Hz, 1H), 2.26-2.13 (m, 1H), 2.13-1.78 (m, 6H), 1.65-1.49 (m, 1H), 1.16 (d, J = 6.6 Hz, 3H) |
| | Example 46<br>4-(4-Methylpiperazin-1-yl)-7,8,9,10-tetrahydro-6H-cyclohepta[4,5]thieno[3,2-d]pyrimidin-2-amine tri-fluoroacetic acid salt<br>MS: 318.1<br>$^1$H NMR (400 MHz, CD$_3$OD) δ ppm 4.78-3.83 (m, 3H), 3.72-3.38 (m, 4H), 3.37-3.33 (m, 1H), 3.05-2.99 (m, 2H), 2.98 (s, 3H), 2.89-2.83 (m, 2H), 2.05-1.93 (m, 2H), 1.83-1.75 (m, 2H), 1.75-1.66 (m, 2H) |
| | Example 47<br>4-[(3R)-3-(Methyl-amino)pyrrolidin-1-yl]-7,8,9,10-tetrahydro-6H-cyclohepta[4,5-d]pyrimi-din-2-amine trifluoroacetic acid salt<br>MS: 318.1<br>$^1$H NMR (400 MHz, CD$_3$OD) δ ppm 4.51-4.05 (m, 4H), 4.03-3.85 (m, 1H), 3.06-2.92 (m, 2H), 2.87-2.83 (m, 1H), 2.81 (s, 3H), 2.72-2.54 (m, 1H), 2.53-2.21 (m, 1H), 2.06-1.89 (m, 2H), 1.82-1.74 (m, 2H), 1.74-1.66 (m, 2H) |
| | Example 48<br>4-[(4aR,7aR)-Octahydro-6H-pyrrolo[3,4-b]pyridin-6-yl]-7,8,9,10-tetrahydro-6H-cyclohepta[4,5-d]pyrimidin-2-amine trifluoroacetic acid salt<br>MS: 344.1<br>$^1$H NMR (400 MHz, CD$_3$OD) δ ppm 4.40-4.17 (m, 2H), 4.14-3.91 (m, 3H), 3.43-3.33 (m, 1H), 3.16-2.94 (m, 4H), 2.90-2.77 (m, 1H), 2.04-1.93 (m, 4H), 1.93-1.81 (m, 2H), 1.82-1.74 (m, 2H), 1.73-1.66 (m, 2H) |

| Structure | Chemical Name, MS Data, NMR Data |
|---|---|
| | Example 49<br>4-[4-(2-Aminoethyl)piperazin-1-yl]-6,7,8,9-tetrahydro[1]benzothieno[3,2-d]pyrimidin-2-amine trifluoroacetic acid salt<br>MS: 333.2<br>¹H NMR (400 MHz, CD₃OD) δ ppm 4.22-4.10 (m, 4H), 3.19-3.11 (m, 2H), 3.09-2.87 (m, 3H), 2.83-2.71 (m, 5H), 2.70-2.63 (m, 2H), 2.03-1.88 (m, 4H) |
| | Example 50<br>4-[4-(1-Methylethyl)piperazin-1-yl]-6,7,8,9-tetrahydro[1]benzothieno[3,2-d]pyrimidin-2-amine trifluoroacetic acid salt<br>MS: 332.2<br>¹H NMR (400 MHz, CD₃OD) δ ppm 4.10-3.36 (m, 9H), 2.92 (t, J = 4.8 Hz, 2H), 2.71-2.65 (m, 2H), 2.02-1.88 (m, 4H), 1.42 (s, 3H), 1.40 (s, 3H) |
| | Example 51<br>4-(4-Ethylpiperazin-1-yl)-6,7,8,9-tetrahydro[1]benzothieno[3,2-d]pyrimidin-2-amine trifluoroacetic acid salt<br>MS: 318.2<br>¹H NMR (400 MHz, CD₃OD) δ ppm 3.65-3.36 (m, 8H), 3.26 (q, J = 7.3 Hz, 2H), 2.92 (t, J = 5.1 Hz, 2H), 2.68 (t, J = 5.2 Hz, 2H), 2.01-1.89 (m, 4H), 1.39 (t, J = 7.3 Hz, 3H) |
| | Example 52<br>4-(Hexahydropyrrolo[1,2-a]pyrazin-2(1H)-yl-6,7,8,9-tetrahydro[1]benzothieno[3,2-d]pyrimidin-2-amine trifluoroacetic acid salt<br>MS: 330.2<br>¹H NMR (400 MHz, CD₃OD) δ ppm 4.83-4.62 (m, 1H), 4.53-4.13 (m, 2H), 4.12-3.79 (m, 2H), 3.79-3.37 (m, 4H), 2.92 (t, J = 5.0 Hz, 2H), 2.68 (t, J = 5.1 Hz, 2H), 2.41-2.28 (m, 1H), 2.28-2.16 (m, 1H), 2.16-2.04 (m, 1H), 2.02-1.86 (m, 5H) |
| | Example 53<br>4-(Octahydro-2H-pyrido[1,2-a]pyrazin-2-yl)-6,7,8,9-tetrahydro[1]benzothieno[3,2-d]pyrimidin-2-amine trifluoroacetic acid salt<br>MS: 344.2<br>¹H NMR (400 MHz, CD₃OD) δ ppm 5.11-4.93 (m, 3H), 3.80-3.64 (m, 1H), 3.64-3.56 (m, 1H), 3.55-3.47 (m, 1H), 3.47-3.37 (m, 1H), 3.36-3.32 (m, 1H), 3.29-3.19 (m, 1H), 3.07-2.95 (m, 1H), 2.92 (t, J = 5.3 Hz, 1H), 2.68 (t, J = 5.1 Hz, 2H), 2.12-1.77 (m, 8H), 1.76-1.55 (m, 2H) |
| | Example 54<br>4-(5,6-Dihydro[1,2,4-a]pyrazin-7(8H)-yl)-6,7,8,9-tetrahydro[1]benzothieno[3,2-d]pyrimidin-2-amine trifluoroacetic acid salt<br>MS: 328.2<br>¹H NMR (400 MHz, CD₃OD) δ ppm 8.65-8.59 (m, 1H), 5.46 (s, 2H), 4.51 (t, J = 5.3 Hz, 2H), 4.43-4.38 (m, 2H), 2.95 (t, J = 5.0 Hz, 2H), 2.68 (t, J = 5.1 Hz, 2H), 2.03-1.89 (m, 4H) |
| | Example 55<br>4-[(3S)-3-(Methylamino)pyrrolidin-1-yl]-6,7,8,9-tetrahydro[1]benzothieno[3,2-d]pyrimidin-2-amine trifluoroacetic acid salt<br>MS: 304.2<br>¹H NMR (400 MHz, CD₃OD) δ ppm 4.26-4.07 (m, 4H), 4.07-3.92 (m, 1H), 2.92 (t, J = 4.9 Hz, 2H), 2.81 (s, 3H), 2.66 (t, J = 5.0 Hz, 2H), 2.63-2.51 (m, 1H), 2.48-2.30 (m, 1H), 2.01-1.87 (m, 4H) |
| | Example 56<br>4-[(3R)-3-Aminopyrrolidin-1-yl]-6,7,8,9-tetrahydro[1]benzothieno[3,2-d]pyrimidin-2-amine trifluoroacetic acid salt<br>MS: 290.2<br>¹H NMR (400 MHz, CD₃OD) δ ppm 4.23-4.01 (m, 5H), 2.92 (t, J = 5.0 Hz, 2H), 2.66 (t, J = 5.1 Hz, 2H), 2.62-2.46 (m, 1H), 2.41-2.21 (m, 1H), 1.99-1.87 (m, 4H) |

41
-continued

| Structure | Chemical Name, MS Data, NMR Data |
|---|---|
| (structure with difluoro cyclohexyl benzothienopyrimidine and N-methylpiperazine) | Example 57<br>8,8-Difluoro-4-(4-methyl-piperazin-1-yl)-6,7,8,9-tetrahydro[1]benzothieno[3,2-d]pyrimidin-2-amine trifluoroacetic acid salt<br>MS: 340.2<br>$^1$H NMR (400 MHz, CD$_3$OD) δ ppm 4.67-3.99 (m, 4H), 3.61-3.41 (m, 4H), 3.25 (t, J = 13.9 Hz, 2H), 3.18 (t, J = 6.4 Hz, 2H), 2.98 (s, 3H), 2.49-2.34 (m, 2H) |
| (structure with difluoro cyclohexyl benzothienopyrimidine and piperazine) | Example 58<br>8,8-Difluoro-4-piperazin-1-yl-6,7,8,9-tetrahydro[1]benzothieno[3,2-d]pyrimidin-2-amine trifluoroacetic acid salt<br>MS: 326.1<br>$^1$H NMR (400 MHz, CD$_3$OD) δ ppm 4.34-4.29 (m, 4H), 3.47-3.42 (m, 4H), 3.25 (t, J = 13.9 Hz, 2H), 3.18 (t, J = 6.6 Hz, 2H), 2.49-2.34 (m, 2H) |

Example 59

8,8-Difluoro-4-[(3R)-3-(methylamino)pyrrolidin-1-yl]-6,7,8,9-tetrahydro[1]benzothieno[3,2-d]pyrimidin-2-amine trifluoroacetic acid salt

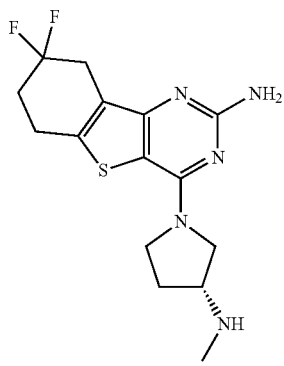 [SMILES: CN[C@@H]1CCN(c2nc(N)nc3c4c(sc23)CCC(F)(F)C4)C1]

MS: 340.2. $^1$H NMR (400 MHz, CD$_3$OD) δ ppm 4.28-3.90 (m, 5H), 3.28-3.14 (m, 4H), 2.82 (s, 3H), 2.72-2.54 (m, 1H), 2.53-2.32 (m, 3H).

42

Example 60

4-(3,8-Diaza-bicyclo[3.2.1]oct-3-yl)-8-methoxy-6,7,8,9-tetrahydro-benzo[4,5]thieno[3,2-d]pyrimidin-2-ylamine hydrochloride

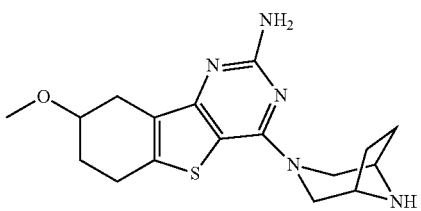 [SMILES: COC1CCc2sc3c(N4CC5CCC(C4)N5)nc(N)nc3c2C1]

MS: 346.2. $^1$H NMR (300 MHz, DMSO-d6): δ 13.70 (br s, 1H), 10.20 (br s, 1H), 9.80 (br s, 1H), 4.70-4.40 (m, 2H), 4.30 (br s, 2H), 4.00-3.70 (m, 3H), 3.70-3.50 (m, 2H), 3.00-2.80 (m, 3H), 3.80-2.60 (m, 1H), 2.10-1.90 (m, 4H), 2.85-2.70 (m, 2H).

Example 61

8-tert-Butyl-4-(4-methyl-piperazin-1-yl)-6,7,8,9-tetrahydro-benzo[4,5]thieno[3,2-d]pyrimidin-2-ylamine (free amine)

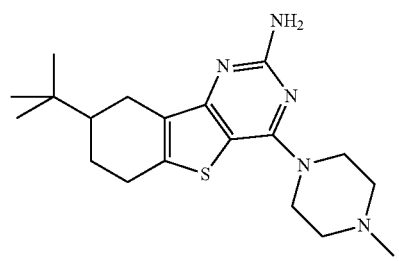 [SMILES: CN1CCN(c2nc(N)nc3c4c(sc23)CCC(C(C)(C)C)C4)CC1]

MS: 360.2. $^1$H NMR (300 MHz, CDCl$_3$): δ 4.86 (br s, 2H), 4.00-3.85 (m, 4H), 3.00-2.70 (m, 3H), 2.60-2.50 (m, 4H), 2.50-2.30 (m, 4H), 2.10-2.05 (m, 1H), 1.60-1.40 (m, 2H), 1.03 (s, 9H).

Example 62

4-[1,4]Diazepan-1-yl-8-trifluoromethyl-6,7,8,9-tetrahydro-benzo[4,5]thieno[3,2-d]pyrimidin-2-ylamine hydrochloride

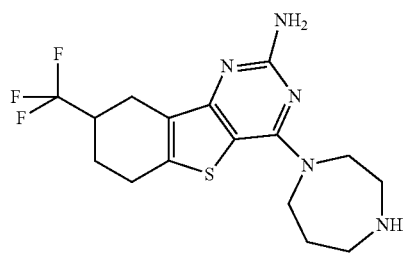 [SMILES: Nc1nc(N2CCCNCC2)c2sc3c(c2n1)CC(C(F)(F)F)CC3]

MS: 372.1. $^1$H NMR (300 MHz, DMSO-d6): δ 13.53 (br s, 1H), 9.56 (br s, 1H), 4.20-4.00 (m, 2H), 3.73-3.65 (m, 6H), 3.45-3.36 (m, 3H), 3.20-3.95 (m, 2H), 2.66-2.62 (m, 1H), 2.55-2.50 (m, 2H), 1.84-1.73 (m, 1H).

Example 63

4-(3(S)-Amino-pyrrolidin-1-yl)-8-tert-butyl-6,7,8,9-tetrahydro-benzo[4,5]thieno[3,2-d]pyrimidin-2-ylamine hydrochloride

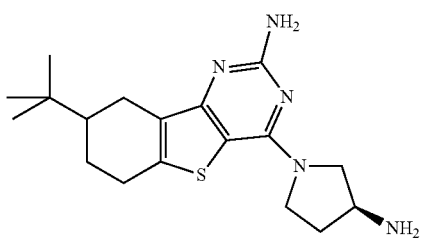 [SMILES: CC(C)(C)C1CCc2sc3c(N4CC[C@H](N)C4)nc(N)nc3c2C1]

MS: 346.2. $^1$H NMR (300 MHz, DMSO-d6): δ 13.52-13.47 (m, 1H), 8.71 (br s, 3H), 6.65-6.25 (m, 2H), 4.25-3.91 (m, 5H), 3.20-3.07 (m, 1H), 3.02-2.75 (m, 2H), 2.47-2.15 (m, 4H), 2.55-2.50 (m, 2H), 1.51-1.36 (m, 1H), 0.98 (s, 9H).

Example 64

4-(3,8-Diazabicyclo[3.2.1]oct-3-yl)-8-methyl-6,7,8,9-tetrahydro[1]benzofuro[3,2-d]pyrimidin-2-amine hydrochloride

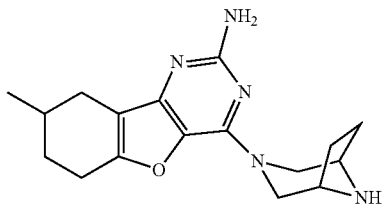 [SMILES: CC1CCc2oc3c(N4CC5CCC(C4)N5)nc(N)nc3c2C1]

MS: 314.2. $^1$H NMR (500 MHz, CD$_3$OD): δ 4.98-4.84 (m, 2H), 4.31-4.26 (m, 2H), 3.99-3.51 (m, 2H), 2.94-2.65 (m, 3H), 2.25-2.15 (m, 3H), 2.10-1.94 (m, 4H), 1.70-1.58 (m, 1H), 1.17 (d, J=6.7, 3H).

Example 65

8-tert-Butyl-4-(3,8-diazabicyclo[3.2.1]oct-3-yl)-6,7,8,9-tetrahydro[1]benzothieno[3,2-d]pyrimidin-2-amine hydrochloride

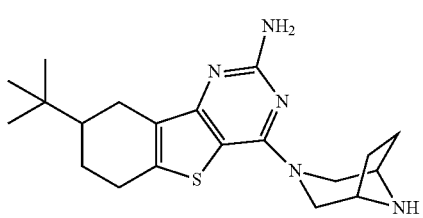 [SMILES: CC(C)(C)C1CCc2sc3c(N4CC5CCC(C4)N5)nc(N)nc3c2C1]

MS: 372.5. $^1$H NMR (500 MHz, CD$_3$OD): δ 4.86-4.79 (m, 2H), 4.31 (s, 2H), 3.78-3.66 (m, 2H), 3.12-3.03 (m, 1H), 2.95-2.82 (m, 2H), 2.43-2.34 (m, 1H), 2.29-2.15 (m, 3H), 2.09-2.00 (m, 2H), 1.67-1.59 (m, 1H), 1.57-1.48 (m, 1H), 1.05 (s, 9H).

Example 66

8-Methoxy-4-(4-methylpiperazin-1-yl)-6,7,8,9-tetrahydro[1]benzothieno[3,2-d]pyrimidin-2-amine

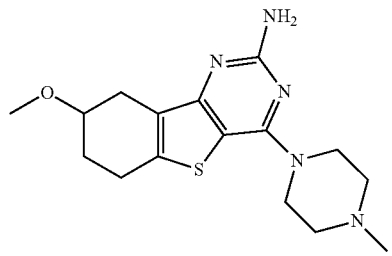

MS: 334.2. $^1$H NMR (500 MHz, CD$_3$OD): δ 4.00-3.86 (m, 4H), 3.86-3.76 (m, 1H), 3.44 (s, 3H), 3.05-2.89 (m, 2H), 2.88-2.76 (m, 1H), 2.67 (dd, J=16.7, 5.8, 1H), 2.60-2.50 (m, 4H), 2.35 (s, 3H), 2.20-1.98 (m, 2H).

Example 67

4-[3-(Aminomethyl)azetidin-1-yl]-8-tert-butyl-6,7,8,9-tetrahydro[1]benzothieno[3,2-d]pyrimidin-2-amine hydrochloride

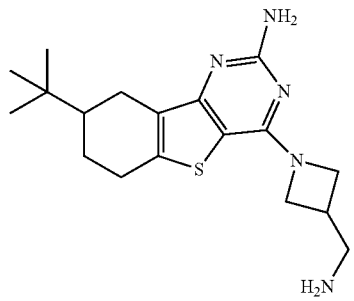 [SMILES: CC(C)(C)C1CCc2sc3c(N4CC(CN)C4)nc(N)nc3c2C1]

MS: 346.2. $^1$H NMR (500 MHz, CD$_3$OD): δ 4.82-4.68 (m, 1H), 4.62-4.49 (m, 1H), 4.47-4.39 (m, 1H), 4.17 (s, 1H), 3.29-3.14 (m, 2H), 3.13-2.97 (m, 1H), 2.94-2.77 (m, 2H), 2.44-2.28 (m, 1H), 2.28-2.15 (m, 1H), 1.71-1.40 (m, 2H), 1.39-1.22 (m, 1H), 1.04 (s, 9H).

Example 68

4-(3,8-Diazabicyclo[3.2.1]oct-3-yl)-8-methyl-6,7,8,9-tetrahydro[1]benzothieno[3,2-d]pyrimidin-2-amine hydrochloride

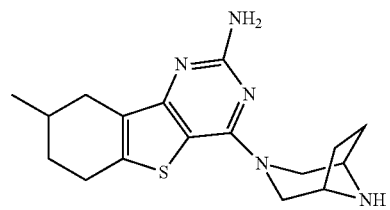

MS: 330.2. $^1$H NMR (500 MHz, CD$_3$OD): δ 4.85-4.74 (m, 2H), 4.31 (s, 2H), 3.79-3.61 (m, 2H), 3.09-2.89 (m, 2H), 2.88-2.77 (m, 1H), 2.35-2.12 (m, 3H), 2.13-1.92 (m, 4H), 1.66-1.50 (m, 1H), 1.19 (d, J=6.6, 3H).

Example 69

4-[(3R)-3-Aminopyrrolidin-1-yl]-8-methoxy-6,7,8,9-tetrahydro[1]benzothieno[3,2-d]pyrimidin-2-amine hydrochloride

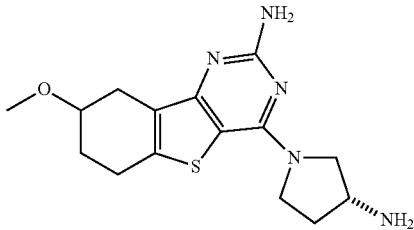 [SMILES: COC1CCc2sc3c(N4CC[C@@H](N)C4)nc(N)nc3c2C1]

MS: 320.2. ¹H NMR (500 MHz, CD₃OD): δ 4.25-3.99 (m, 4H), 3.97-3.85 (m, 1H), 3.45 (s, 3H), 3.41-3.36 (m, 1H), 3.12-3.00 (m, 1H), 2.99-2.88 (m, 2H), 2.81-2.69 (m, 1H), 2.67-2.49 (m, 1H), 2.41-2.24 (m, 1H), 2.22-2.03 (m, 2H).

Example 70

4-piperazin-1-yl-8-(trifluoromethyl)-6,7,8,9-tetrahydro[1]benzofuro[3,2-d]pyrimidin-2-amine hydrochloride

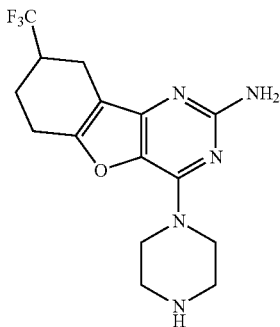

MS: 342.1. ¹H NMR (300 MHz, DMSO-d6): δ 13.8 (br s, 1H), 9.84 (s, 2H), 7.67 (br s, 2H), 4.22 (br s, 4H), 3.50 (br s, 2H), 3.16 (br s, 2H), 2.96-2.90 (br m, 4H), 2.58 (m, 1H), 2.25 (m, 1H), 1.87-1.80 (m, 1H).

Example 71

4-(4-Methylpiperazin-1-yl)-8-(trifluoromethyl)-6,7,8,9-tetrahydro[1]benzofuro[3,2-d]pyrimidin-2-amine

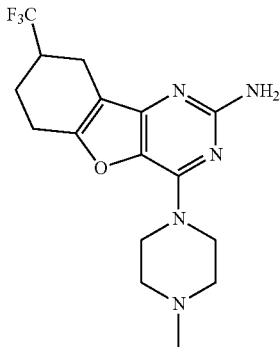 [SMILES: CN1CCN(c2nc(N)nc3c4c(oc23)CCC(C(F)(F)F)C4)CC1]

MS: 356.1. ¹H NMR (300 MHz, CDCl₃): δ 4.57 (s, 2H), 3.93 (m, 4H), 2.98-2.91 (m, 2H), 2.85-2.74 (m, 2H), 2.61-2.56 (m, 2H), 2.50-2.47 (m, 4H), 2.33 (s, 3H), 1.94-1.82 (m, 1H).

Example 72

8-tert-Butyl-4-(4-methylpiperazin-1-yl)-6,7,8,9-tetrahydro[1]benzofuro[3,2-d]pyrimidin-2-amine

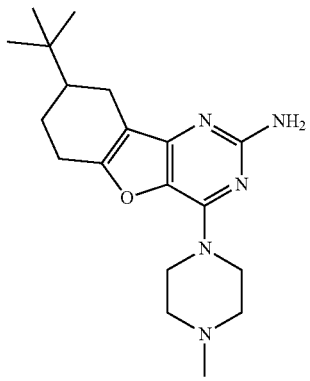 [SMILES: CN1CCN(c2nc(N)nc3c4c(oc23)CCC(C(C)(C)C)C4)CC1]

MS: 344.1. ¹H NMR (300 MHz, CDCl₃): δ 4.80 (br s, 2H), 3.97 (br s, 4H), 2.77-2.66 (m, 2H), 2.57-2.52 (m, 4H), 2.36 (s, 3H), 2.36-2.30 (m, 2H), 2.25-2.15 (m, 1H), 1.52-1.47 (m, 2H), 0.97 (s, 9H).

Example 73

8-Methyl-4-piperazin-1-yl-6,7,8,9-tetrahydro[1]benzofuro[3,2-d]pyrimidin-2-amine hydrochloride

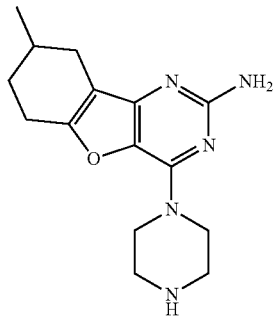

MS: 288.1. ¹H NMR (300 MHz, DMSO-d6): δ 13.63 (br s, 1H), 9.72 (br s, 2H), 7.63 (br s, 2H), 4.20 (br s, 4H), 3.27 (br s, 4H), 2.68-2.62 (m, 2H), 2.49-2.43 (m, 1H), 2.13-2.10 (m, 1H), 1.95-1.90 (m, 2H), 1.52-1.48 (m, 1H), 1.05 (d, J=6.0, 3H).

Example 74

8-Methyl-4-(4-methylpiperazin-1-yl)-6,7,8,9-tetrahydro[1]benzofuro[3,2-d]pyrimidin-2-amine

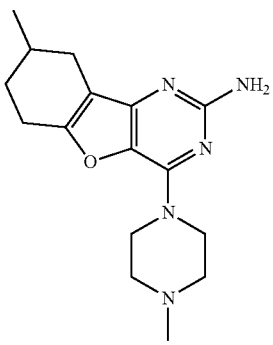 [SMILES: CC1CCc2oc3c(N4CCN(C)CC4)nc(N)nc3c2C1]

MS: 302.1 [M+H]⁺. ¹H NMR (300 MHz, CDCl₃): δ 4.55 (s, 2H), 3.94-3.91 (m, 4H), 2.74-2.67 (m, 3H), 2.50-2.47 (m, 4H), 2.17-2.11 (m, 1H), 2.11-1.93 (m, 2H), 1.59-1.52 (m, 1H), 1.08 (d, J=6.2, 3H).

Example 75

6,6-Dimethyl-4-(4-methylpiperazin-1-yl)-6,7,8,9-tetrahydro[1]benzothieno[3,2-d]pyrimidin-2-amine

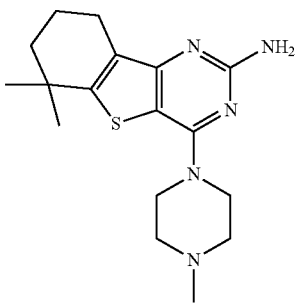

MS: 332.1 [M+H]⁺. ¹H NMR (300 MHz, CDCl₃): δ 4.68 (br s, 2H), 3.92-3.88 (m, 4H), 2.67-2.63 (m, 2H), 2.52-2.48 (m, 4H), 1.89-1.85 (m, 2H), 1.76-1.72 (m, 2H), 1.34 (s, 6H).

Example 76

4-(1,4-Diazepan-1-yl)-8-methoxy-6,7,8,9-tetrahydro[1]benzothieno[3,2-d]pyrimidin-2-amine hydrochloride

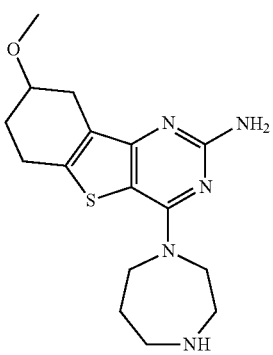 [SMILES: COC1CCc2sc3c(N4CCCNCC4)nc(N)nc3c2C1]

MS: 334.1 [M+H]⁺. ¹H NMR (300 MHz, DMSO-d6): δ 13.41 (br s, 1H), 9.34 (br s, 2H), 8.0-7.9 (br s, 2H), 4.16 (br s, 2H), 4.03 (br s, 2H), 3.82 (br s, 1H), 3.31 (s, 3H), 3.24 (br s, 3H), 2.92-2.88 (m, 3H), 2.74-2.69 (m, 1H), 2.17 (br s, 2H), 2.00 (br s, 2H).

Example 77

8-tert-Butyl-4-[(3R)-3-(methylamino)pyrrolidin-1-yl]-6,7,8,9-tetrahydro[1]benzofuro[3,2-d]pyrimidin-2-amine hydrochloride

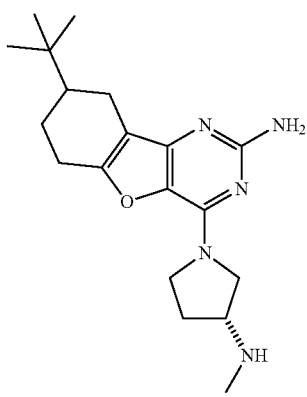 [SMILES: CN[C@@H]1CCN(c2nc(N)nc3c4c(oc23)CCC(C(C)(C)C)C4)C1]

MS: 344.1 [M+H]⁺. ¹H NMR (300 MHz, CDCl₃): δ 5.20 (br s, 2H), 3.93 (br s, 3H), 3.84 (br s, 1H), 3.69-3.63 (m, 1H), 3.44-3.37 (m, 1H), 2.77-2.62 (m, 3H), 2.51 (s, 3H), 2.33-2.11 (m, 3H), 1.96-1.89 (m, 1H), 1.51-1.44 (m, 2H), 0.97 (s, 9H).

Example 78

4-[(3R)-3-(Methylamino)pyrrolidin-1-yl]-8-(trifluoromethyl)-6,7,8,9-tetrahydro[1]benzofuro[3,2-d]pyrimidin-2-amine hydrochloride

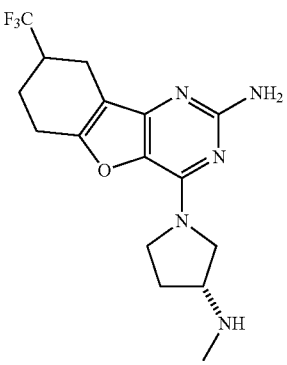 [SMILES: CN[C@@H]1CCN(c2nc(N)nc3c4c(oc23)CCC(C(F)(F)F)C4)C1]

MS: 355.2 [M+H]⁺. ¹H NMR (300 MHz, CD₃OD): δ 3.96 (br s, 2H), 3.83 (br s, 1H), 3.64 (br s, 1H), 3.39-3.33 (m, 1H), 2.97-2.86 (m, 3H), 2.69-2.55 (m, 2H), 2.47 (s, 3H), 2.37-2.23 (m, 2H), 1.95-1.89 (m, 2H).

Example 79

4-[(3S)-3-Aminopyrrolidin-1-yl]-8-methoxy-6,7,8,9-tetrahydro[1]benzothieno[3,2-d]pyrimidin-2-amine hydrochloride

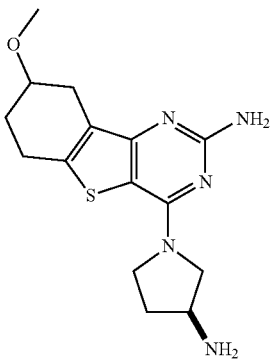 [SMILES: COC1CCc2sc3c(N4CC[C@H](N)C4)nc(N)nc3c2C1]

MS: 320.3 [M+H]⁺. ¹H NMR (300 MHz, DMSO-d6): δ 13.45 (br s, 1H), 8.66 (s, 3H), 7.82 (br s, 2H), 4.21-3.81 (m, 6H), 3.49 (s, 3H), 2.92-2.88 (m, 3H), 2.73-2.68 (m, 1H), 2.50-2.43 (m, 2H), 2.01-1.91 (m, 2H).

Example 80

8-Methoxy-4-[(3R)-3-(methylamino)pyrrolidin-1-yl]-6,7,8,9-tetrahydro[1]benzothieno[3,2-d]pyrimidin-2-amine hydrochloride

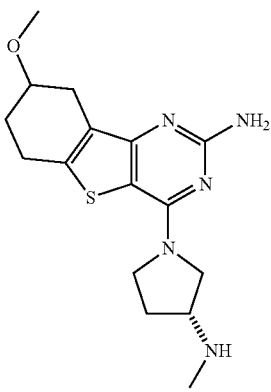 [SMILES: CN[C@@H]1CCN(c2nc(N)nc3c4c(sc23)CCC(OC)C4)C1]

MS: 334.1 [M+H]⁺. ¹H NMR (300 MHz, CDCl₃): δ 5.21 (br s, 2H), 3.92-3.85 (m, 2H), 3.82-3.74 (m, 2H), 3.66-3.61 (m, 1H), 3.42-3.37 (m, 1H), 3.41 (s, 3H), 3.05-2.97 (m, 1H), 2.93-2.89 (m, 1H), 2.83-2.72 (m, 2H), 2.48 (s, 3H), 2.21-2.15 (m, 1H), 2.05-2.01 (m, 2H), 1.94-1.88 (m, 1H).

Example 81

4-[(3R)-3-Aminopyrrolidin-1-yl]-8-(trifluoromethyl)-6,7,8,9-tetrahydro[1]benzothieno[3,2-d]pyrimidin-2-amine hydrochloride

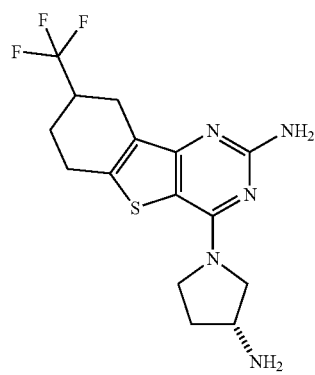 [SMILES: Nc1nc(N2CC[C@@H](N)C2)c2sc3c(c2n1)CC(C(F)(F)F)CC3]

MS: 358.1 [M+H]⁺. ¹H NMR (300 MHz, DMSO-d6): δ 13.40 (br s, 1H), 8.68 (s, 3H), 8.2-7.8 (br s, 2H), 4.22-4.18 (m, 1H), 4.05-3.80 (m, 4H), 3.06-2.93 (m, 3H), 2.63-2.50 (m, 2H), 2.32-2.20 (m, 3H), 1.80-1.74 (m, 1H).

Example 82

4-[(3R)-3-Aminopyrrolidin-1-yl]-8-(trifluoromethyl)-6,7,8,9-tetrahydro[1]benzofuro[3,2-d]pyrimidin-2-amine hydrochloride

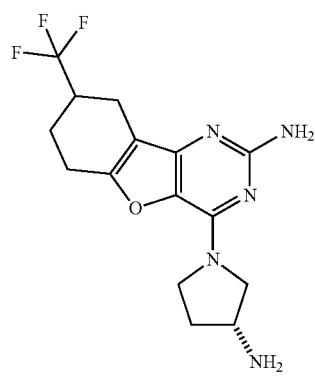 [SMILES: Nc1nc(N2CC[C@@H](N)C2)c2oc3c(c2n1)CC(C(F)(F)F)CC3]

MS: 342.1 [M+H]⁺. ¹H NMR (300 MHz, CD₃OD): δ 4.41-4.00 (br m, 5H), 3.30-2.95 (m, 3H), 2.88-2.65 (m, 3H), 2.53-2.25 (m, 2H), 2.02-1.97 (m, 1H).

Example 83

4-[(3S)-3-Aminopyrrolidin-1-yl]-8-(trifluoromethyl)-6,7,8,9-tetrahydro[1]benzofuro[3,2-d]pyrimidin-2-amine hydrochloride

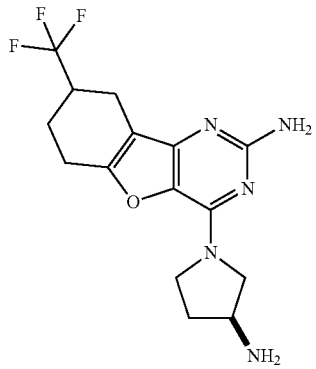 [SMILES: Nc1nc(N2CC[C@H](N)C2)c2oc3c(c2n1)CC(C(F)(F)F)CC3]

MS: 342.1 [M+H]$^+$. $^1$H NMR (300 MHz, CD$_3$OD): δ 4.41-4.00 (br m, 5H), 3.30-2.95 (m, 3H), 2.88-2.65 (m, 3H), 2.53-2.25 (m, 2H), 2.02-1.97 (m, 1H).

Example 84

4-[(3R)-3-Aminopyrrolidin-1-yl]-8-methyl-6,7,8,9-tetrahydro[1]benzothieno[3,2-d]pyrimidin-2-amine hydrochloride

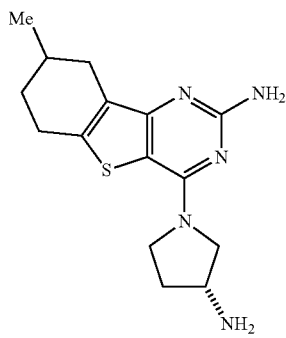 [SMILES: CC1CCc2sc3c(N4CC[C@@H](N)C4)nc(N)nc3c2C1]

MS: 304.2 [M+H]$^+$. $^1$H NMR (300 MHz, DMSO-d6): δ 12.99 (br s, 1H), 8.45 (s, 3H), 4.10-3.90 (m, 4H), 2.94-2.80 (m, 3H), 2.27-2.12 (m, 3H), 1.96-1.90 (m, 2H), 1.60-1.50 (m, 1H), 1.08 (d, J=6.3, 3H).

Example 85

4-[(3S)-3-Aminopyrrolidin-1-yl]-8-methyl-6,7,8,9-tetrahydro[1]benzothieno[3,2-d]pyrimidin-2-amine hydrochloride

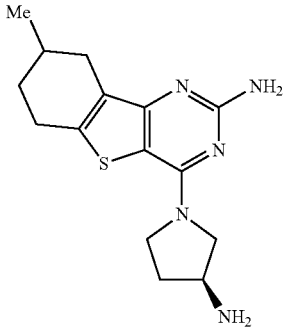 [SMILES: CC1CCc2sc3c(N4CC[C@H](N)C4)nc(N)nc3c2C1]

MS: 304.2 [M+H]$^+$. $^1$H NMR (300 MHz, DMSO-d6): δ 13.05 (br s, 1H), 8.54 (s, 3H), 4.05-3.90 (m, 4H), 2.94-2.80 (m, 3H), 2.27-2.12 (m, 3H), 1.96-1.90 (m, 2H), 1.60-1.50 (m, 1H), 1.08 (d, J=6.3, 3H).

Example 86

4-[3-(Aminomethyl)azetidin-1-yl]-8-methoxy-6,7,8,9-tetrahydro[1]benzothieno[3,2-d]pyrimidin-2-amine hydrochloride

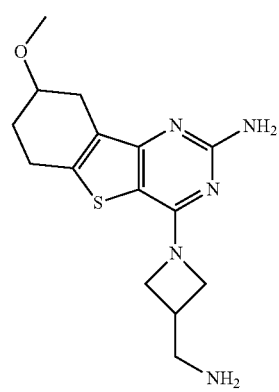 [SMILES: COC1CCc2sc3c(N4CC(CN)C4)nc(N)nc3c2C1]

MS: 320.1 [M+H]$^+$. $^1$H NMR (300 MHz, DMSO-d6): δ 13.26 (br s, 1H), 8.25 (s, 3H), 7.90 (br s, 2H), 4.77 (br s, 2H), 4.62-4.57 (m, 1H), 4.39-4.30 (m, 2H), 4.13-4.10 (m, 1H), 3.80 (s, 1H), 3.20-3.15 (m, 1H), 3.17 (s, 3H), 2.90-2.85 (m, 2H), 2.72-2.65 (m, 1H), 2.01-1.98 (m, 2H).

Example 87

4-[(3S)-3-Aminopyrrolidin-1-yl]-6,6-dimethyl-6,7,8,9-tetrahydro[1]benzofuro[3,2-d]pyrimidin-2-amine hydrochloride

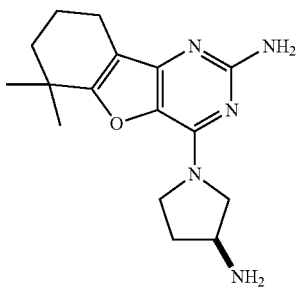 [SMILES: CC1(C)CCCc2c1oc1c(N3CC[C@H](N)C3)nc(N)nc21]

MS: 302.1 [M+H]⁺. ¹H NMR (300 MHz, DMSO-d6): δ 13.09 (br s, 1H), 8.41 (br s, 3H), 7.52 (br s, 2H), 4.10-3.95 (m, 6H), 2.15-2.05 (m, 2H), 1.82-1.75 (m, 4H), 1.31 (s, 6H).

Example 88

4-[(3R)-3-Aminopyrrolidin-1-yl]-6,6-dimethyl-6,7,8,9-tetrahydro[1]benzofuro[3,2-d]pyrimidin-2-amine hydrochloride

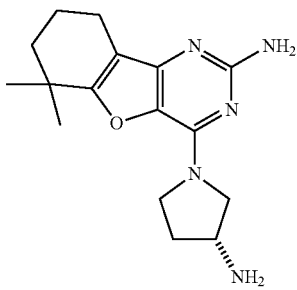 [SMILES: CC1(C)CCCc2c1oc1c(N3CC[C@@H](N)C3)nc(N)nc21]

MS: 302.1 [M+H]⁺. ¹H NMR (300 MHz, DMSO-d6): δ 13.09 (br s, 1H), 8.41 (br s, 3H), 7.52 (br s, 2H), 4.10-3.95 (m, 6H), 2.15-2.05 (m, 2H), 1.82-1.75 (m, 4H), 1.31 (s, 6H).

Example 89

6,6-Dimethyl-4-[(3R)-3-(methylamino)pyrrolidin-1-yl]-6,7,8,9-tetrahydro[1]benzofuro[3,2-d]pyrimidin-2-amine hydrochloride

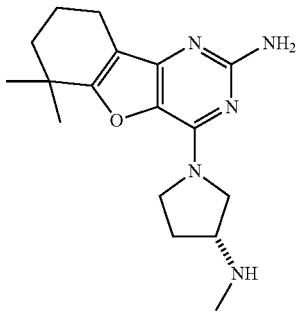 [SMILES: CN[C@@H]1CCN(c2nc(N)nc3c4c(oc23)C(C)(C)CCC4)C1]

MS: 316.2 [M+H]⁺. ¹H NMR (300 MHz, CDCl₃): δ 6.1 (br s, 1H), 4.05-3.90 (m, 4H), 3.50 (br s, 2H), 2.66-2.62 (m, 2H), 2.54 (s, 3H), 2.30-2.10 (m, 3H), 1.82-1.73 (m, 4H), 1.28 (s, 6H).

Example 90

4-[3-(Aminomethyl)azetidin-1-yl]-6,6-dimethyl-6,7,8,9-tetrahydro[1]benzofuro[3,2-d]pyrimidin-2-amine hydrochloride

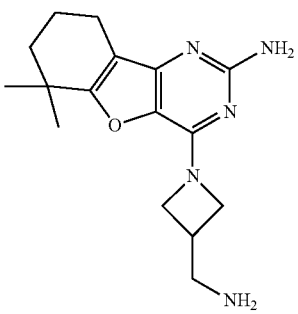 [SMILES: CC1(C)CCCc2c1oc1c(N3CC(CN)C3)nc(N)nc21]

MS: 302.1 [M+H]⁺. ¹H NMR (300 MHz, DMSO-d6): δ 13.05 (br s, 1H), 8.16 (br s, 3H), 7.52 (br s, 2H), 4.64-4.13 (m, 4H), 3.18 (s, 3H), 1.79-1.73 (m, 4H), 1.28 (s, 6H).

Example 91

6,6-Dimethyl-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine

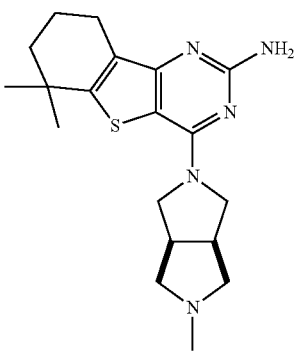

MS: 358.1 [M+H]⁺. ¹H NMR (300 MHz, CD₃OD): δ 4.25-4.17 (br m, 5H), 3.40 (br m, 3H), 3.03 (s, 3H), 2.69 (t, J=6.3, 2H), 2.06-2.02 (m, 3H), 1.89-1.85 (m, 2H), 1.47 (s, 6H).

Example 92

8-tert-Butyl-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine

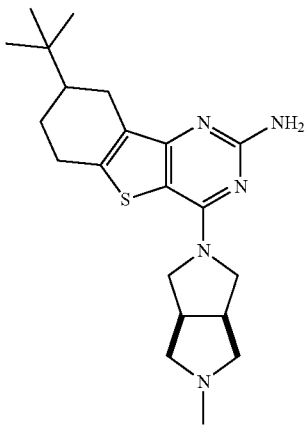

MS: 386.1 [M+H]⁺. ¹H NMR (300 MHz, CD₃OD): δ 4.25-4.00 (br m, 4H), 3.90-3.85 (br m, 1H), 3.54-3.35 (m, 4H), 3.13-3.01 (m, 5H), 2.91-2.85 (m, 2H), 2.44-2.26 (m, 2H), 1.68-1.52 (m, 2H), 1.08 (s, 9H).

Example 93

4-[(3aR,6aS)-5-Methylhexahydropyrrolo[3,4-c]pyrrol-2(1H)-yl]-8-(trifluoromethyl)-6,7,8,9-tetrahydro[1]benzothieno[3,2-d]pyrimidin-2-amine

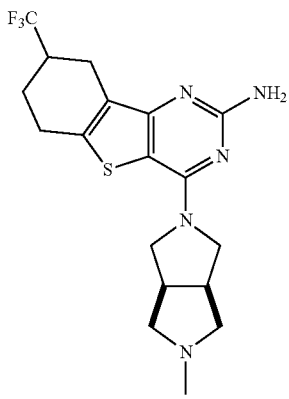

MS: 398.1 [M+H]⁺. ¹H NMR (300 MHz, CD₃OD): δ 4.25-4.00 (br m, 4H), 3.90-3.85 (br m, 1H), 3.54-3.40 (m, 4H), 3.21-3.01 (m, 7H), 2.91-2.68 (m, 2H), 2.43-2.39 (m, 1H), 1.97-1.89 (m, 1H).

Example 94

8-Methyl-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine

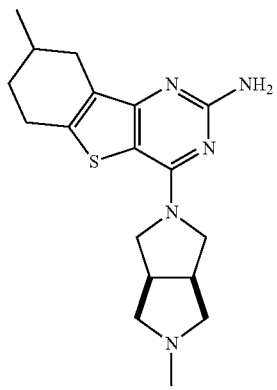

MS: 344.1 [M+H]⁺. ¹H NMR (300 MHz, CD₃OD): δ 4.25-4.00 (br m, 4H), 3.90-3.85 (br m, 1H), 3.51-3.40 (m, 4H), 3.22-3.12 (m, 1H), 3.04-3.01 (m, 3H), 2.89-2.83 (m, 2H), 2.29-2.20 (m, 1H), 2.13-2.03 (m, 2H), 1.66-1.58 (m, 2H), 1.21 (d, J=6.3, 3H).

Example 95

8-tert-Butyl-4-[(3aR,6aS)-5-methylhexahydropyrrolo[3,4-c]pyrrol-2(1H)-yl]-6,7,8,9-tetrahydro[1]benzofuro[3,2-d]pyrimidin-2-amine

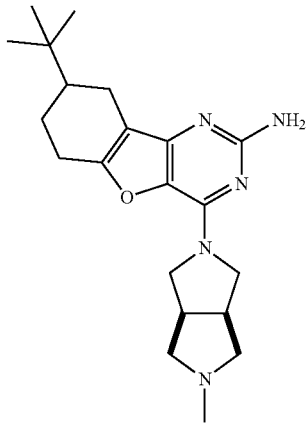

MS: 370.2 [M+H]⁺. ¹H NMR (300 MHz, CDCl₃): δ 4.70 (br s, 2H), 3.92-3.86 (m, 2H), 3.76-3.73 (m, 2H), 2.96 (br s,

2H), 2.79-2.65 (m, 5H), 2.46-2.42 (m, 2H), 2.33 (s, 3H), 2.33-2.30 (m, 1H), 2.10-2.04 (m, 1H), 1.48-1.44 (m, 2H), 0.96 (s, 9H).

Example 96

8-Methoxy-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine

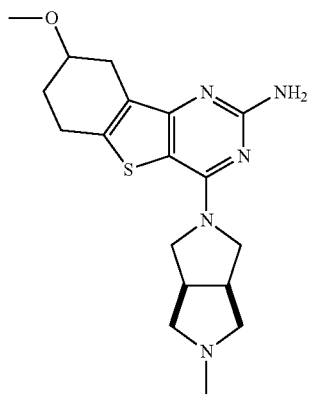

MS: 360.1 [M+H]$^+$. $^1$H NMR (300 MHz, CD$_3$OD): δ 4.22-4.00 (br m, 5H), 3.90-3.85 (br m, 1H), 3.54-3.35 (m, 5H), 3.39 (s, 3H), 3.15-2.90 (m, 6H), 2.75-2.70 (m, 1H), 2.14 (br s, 2H).

Example 97

4-[(3aR,6aS)-5-Methylhexahydropyrrolo[3,4-c]pyrrol-2(1H)-yl]-8-(trifluoromethyl)-6,7,8,9-tetrahydro[1]benzofuro[3,2-d]pyrimidin-2-amine

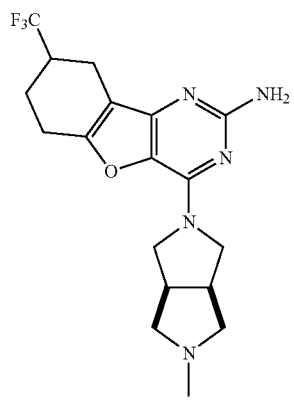

MS: 382.1 [M+H]$^+$. $^1$H NMR (300 MHz, CDCl$_3$): δ 4.66 (br s, 2H), 3.89-3.8 (m, 2H), 3.76-3.72 (m, 2H), 2.98-2.95 (m, 3H), 2.79-2.75 (m, 3H), 2.66-2.58 (m, 1H), 2.47-2.43 (m, 3H), 2.35 (s, 3H), 2.33-2.30 (m, 2H), 1.91-1.88 (m, 1H).

Example 98

8-Methyl-4-[(3aR,6aS)-5-methylhexahydropyrrolo[3,4-c]pyrrol-2(1H)-yl]-6,7,8,9-tetrahydro[1]benzofuro[3,2-d]pyrimidin-2-amine

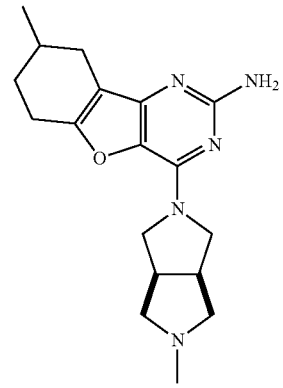

MS: 328.2 [M+H]$^+$. $^1$H NMR (300 MHz, CDCl$_3$): δ 4.66 (br s, 2H), 3.92-3.86 (m, 2H), 3.76-3.72 (m, 2H), 2.94 (br s, 2H), 2.78-2.68 (m, 5H), 2.43-2.40 (m, 2H), 2.33 (s, 3H), 2.18-2.14 (m, 1H), 2.00-1.90 (m, 2H), 1.60-1.50 (m, 1H), 1.09 (d, J=6.3, 3H).

Example 99

4-(1,4-Diazepan-1-yl)-6,6-dimethyl-6,7,8,9-tetrahydro[1]benzofuro[3,2-d]pyrimidin-2-amine hydrochloride

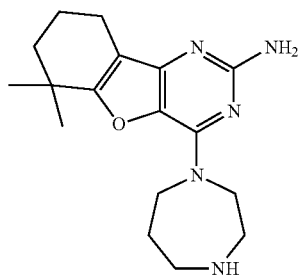 [SMILES: CC1(C)CCCc2c1oc1c(N3CCCNCC3)nc(N)nc21]

MS: 316.3 [M+H]$^+$. $^1$H NMR (300 MHz, CD$_3$OD): δ 4.44-4.40 (br m, 1H), 4.30-4.24 (m, 2H), 4.14-4.10 (m, 1H), 3.65 (s, 2H), 3.60-3.45 (m, 6H), 2.62-2.58 (m, 2H), 2.33-2.26 (m, 3H), 1.95-1.92 (m, 2H), 1.84-1.80 (m, 2H), 1.37 (s, 6H).

Example 100

6,6-Dimethyl-4-piperazin-1-yl-6,7,8,9-tetrahydro[1]benzofuro[3,2-d]pyrimidin-2-amine hydrochloride

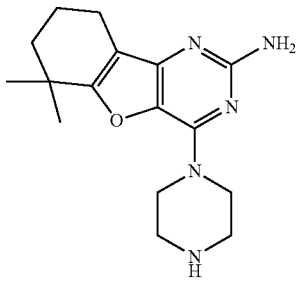 [SMILES: CC1(C)CCCc2c1oc1c(N3CCNCC3)nc(N)nc21]

MS: 302.3 [M+H]$^+$. $^1$H NMR (300 MHz, CD$_3$OD): δ 4.41-4.38 (br m, 3H), 3.60-3.45 (m, 11H), 2.62-2.58 (m, 2H), 1.93-1.91 (m, 2H), 1.84-1.80 (m, 2H), 1.38 (s, 6H).

Example 101

6,6-Dimethyl-4-(4-methylpiperazin-1-yl)-6,7,8,9-tetrahydro[1]benzofuro[3,2-d]pyrimidin-2-amine

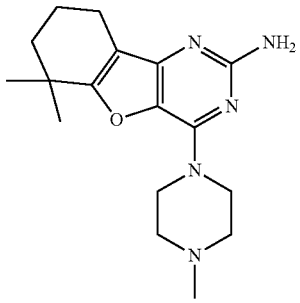 [SMILES: CN1CCN(c2nc(N)nc3c4c(oc23)C(C)(C)CCC4)CC1]

MS: 316.2 [M+H]$^+$. $^1$H NMR (300 MHz, CDCl$_3$): δ 4.80 (br s, 2H), 3.92-3.88 (m, 4H), 2.67-2.52 (m, 6H), 1.82-1.80 (m, 2H), 1.74-1.72 (m, 2H), 1.29 (s, 6H).

Example 102

N$^4$-(2-Aminoethyl)-N$^4$,6,6-trimethyl-6,7,8,9-tetrahydro[1]benzothieno[3,2-d]pyrimidine-2,4-diamine hydrochloride

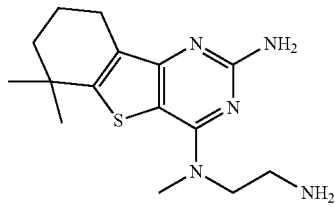 [SMILES: CN(CCN)c1nc(N)nc2c3c(sc12)C(C)(C)CCC3]

MS: 306.2 [M+H]$^+$. $^1$H NMR (300 MHz, DMSO-d6): δ 13.10-13.00 (br s, 1H), 8.02 (br s, 3H), 7.70-7.65 (br s, 2H), 3.96 (br s, 2H), 3.50 (br s, 3H), 3.18-3.14 (m, 2H), 1.79-1.72 (m, 4H), 1.29 (s, 6H).

Example 103

N$^4$-(2-Aminoethyl)-N$^4$,6,6-trimethyl-6,7,8,9-tetrahydro[1]benzofuro[3,2-d]pyrimidine-2,4-diamine hydrochloride

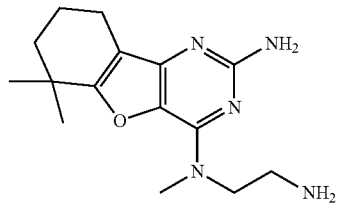

MS: 290.2 [M+H]$^+$. $^1$H NMR (300 MHz, DMSO-d6): δ 13.10-13.00 (br s, 1H), 8.02 (br s, 3H), 7.70-7.65 (br s, 2H), 3.96 (br s, 2H), 3.50 (br s, 3H), 3.18-3.14 (m, 2H), 1.79-1.72 (m, 4H), 1.29 (s, 6H).

Example 104

N$^4$-(2-Aminoethyl)-8-methoxy-N$^4$-methyl-6,7,8,9-tetrahydro[1]benzothieno[3,2-d]pyrimidine-2,4-diamine hydrochloride

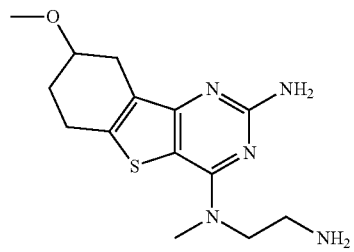 [SMILES: COC1CCc2sc3c(N(C)CCN)nc(N)nc3c2C1]

MS: 308.2 [M+H]$^+$. $^1$H NMR (300 MHz, DMSO-d6): δ 13.10-13.00 (br s, 1H), 8.04 (br s, 3H), 7.90-7.70 (br s, 2H), 3.97-3.81 (m, 4H), 3.48-3.30 (m, 7H), 2.92-2.88 (m, 3H), 2.73-2.64 (m, 1H), 2.00-1.98 (m, 2H).

Example 105

N$^4$-(2-Aminoethyl)-8-methoxy-N$^4$-methyl-6,7,8,9-tetrahydro[1]benzofuro[3,2-d]pyrimidine-2,4-diamine hydrochloride

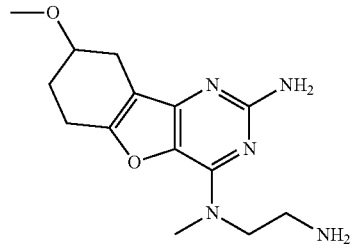 [SMILES: COC1CCc2oc3c(N(C)CCN)nc(N)nc3c2C1]

MS: 292.2 [M+H]$^+$. $^1$H NMR (300 MHz, DMSO-d6): δ 13.10-13.00 (br s, 1H), 8.07 (br s, 3H), 7.55-7.45 (br s, 2H), 3.97-3.81 (m, 4H), 3.30 (s, 3H), 3.30-3.10 (m, 4H), 2.77-2.63 (m, 3H), 2.05-1.98 (m, 2H).

Example 106

N⁴-(2-Aminoethyl)-8-tert-butyl-N⁴-methyl-6,7,8,9-tetrahydro[1]benzothieno[3,2-d]pyrimidine-2,4-diamine hydrochloride

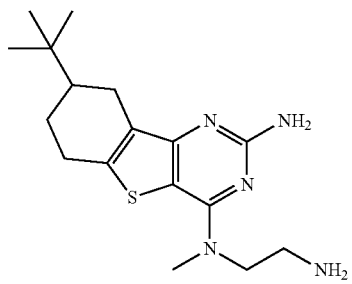 [SMILES: CN(CCN)c1nc(N)nc2c3c(sc12)CCC(C(C)(C)C)C3]

MS: 334.2 [M+H]⁺. ¹H NMR (300 MHz, DMSO-d6): δ 13.10-13.00 (br s, 1H), 8.08 (br s, 3H), 7.70-7.55 (br s, 2H), 3.96 (s, 2H), 3.48 (s, 3H), 3.18-2.86 (m, 5H), 2.26-2.09 (m, 2H), 1.60-1.50 (m, 2H), 0.97 (s, 9H).

Example 107

N⁴-(2-Aminoethyl)-8-tert-butyl-N⁴-methyl-6,7,8,9-tetrahydro[1]benzofuro[3,2-d]pyrimidine-2,4-diamine hydrochloride

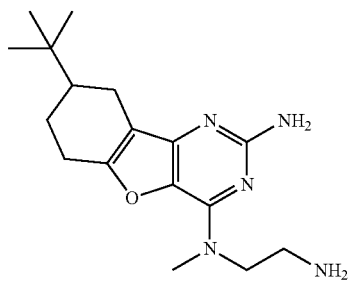 [SMILES: CN(CCN)c1nc(N)nc2c3c(oc12)CCC(C(C)(C)C)C3]

MS: 318.1 [M+H]⁺. ¹H NMR (300 MHz, DMSO-d6): δ 13.10-13.00 (br s, 1H), 8.10 (br s, 3H), 7.50-7.45 (br s, 2H), 3.96 (br m, 2H), 3.48 (s, 3H), 2.83-2.63 (m, 5H), 2.25-2.10 (m, 2H), 1.46-1.43 (m, 2H), 0.95 (s, 9H).

Example 108

N⁴-(2-Aminoethyl)-N⁴-methyl-8-(trifluoromethyl)-6,7,8,9-tetrahydro[1]benzothieno[3,2-d]pyrimidine-2,4-diamine hydrochloride

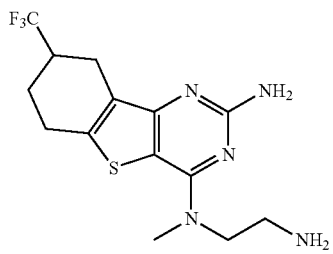 [SMILES: CN(CCN)c1nc(N)nc2c3c(sc12)CCC(C(F)(F)F)C3]

MS: 346.2 [M+H]⁺. ¹H NMR (300 MHz, DMSO-d6): δ 13.10-13.00 (br s, 1H), 8.15 (br s, 3H), 7.90-7.70 (br s, 2H), 3.98 (s, 2H), 3.49 (s, 3H), 3.18-2.91 (m, 6H), 2.64-2.55 (m, 1H), 2.25-2.09 (m, 1H), 1.80-1.76 (m, 1H).

Example 109

N⁴-(2-Aminoethyl)-N⁴-methyl-8-(trifluoromethyl)-6,7,8,9-tetrahydro[1]benzofuro[3,2-d]pyrimidine-2,4-diamine hydrochloride

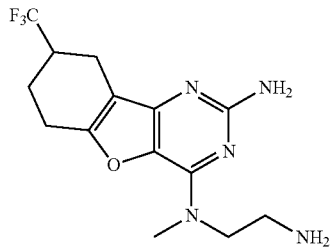 [SMILES: CN(CCN)c1nc(N)nc2c3c(oc12)CCC(C(F)(F)F)C3]

MS: 330.2 [M+H]⁺. ¹H NMR (300 MHz, DMSO-d6): δ 13.43 (s, 1H), 8.19 (br s, 3H), 7.59 (br s, 2H), 3.92 (br s, 2H), 3.46 (s, 3H), 3.15-3.13 (m, 2H), 2.92-2.88 (m, 4H), 2.58-2.55 (m, 1H), 2.25-2.20 (m, 1H), 1.81-1.77 (m, 1H).

Example 110

N⁴-(2-Aminoethyl)-N⁴,8-dimethyl-6,7,8,9-tetrahydro[1]benzothieno[3,2-d]pyrimidine-2,4-diamine hydrochloride

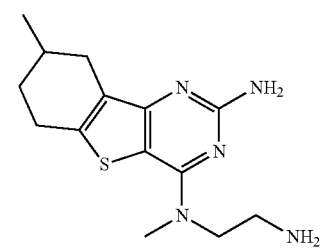 [SMILES: CC1CCc2sc3c(N(C)CCN)nc(N)nc3c2C1]

MS: 292.2 [M+H]⁺. ¹H NMR (300 MHz, DMSO-d6): δ 13.10-13.00 (br s, 1H), 8.08 (br s, 3H), 7.90-7.70 (br s, 2H), 3.96 (s, 2H), 3.48 (s, 3H), 3.17-2.80 (m, 5H), 2.27-2.17 (m, 1H), 1.95-1.90 (m, 2H), 1.48-1.45 (m, 1H), 1.09 (d, J=6.3, 3H).

Example 111

N⁴-(2-Aminoethyl)-N⁴,8-dimethyl-6,7,8,9-tetrahydro[1]benzofuro[3,2-d]pyrimidine-2,4-diamine hydrochloride

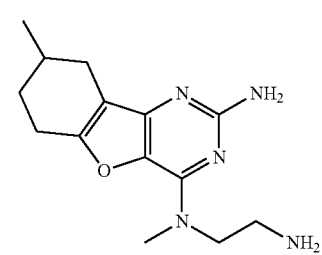 [SMILES: CC1CCc2oc3c(N(C)CCN)nc(N)nc3c2C1]

MS: 276.1 [M+H]⁺. ¹H NMR (300 MHz, DMSO-d6): δ 13.20 (s, 1H), 8.05 (br s, 3H), 7.50-7.48 (br s, 2H), 3.89 (m,

2H), 3.48 (s, 3H), 3.17-2.80 (m, 5H), 2.27-2.17 (m, 1H), 1.95-1.90 (m, 2H), 1.48-1.45 (m, 1H), 1.07 (d, J=6.3, 3H).

Example 112

8,8-Difluoro-4-[(3S)-3-(methylamino)pyrrolidin-1-yl]-6,7,8,9-tetrahydro[1]benzothieno[3,2-d]pyrimidin-2-amine trifluoroacetate

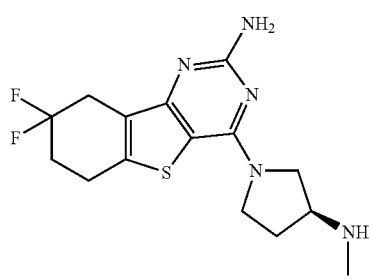 [SMILES: CN[C@H]1CCN(c2nc(N)nc3c4c(sc23)CCC(F)(F)C4)C1]

MS: 340.1 [M+H]+. 1H NMR (400 MHz, CD3OD): δ 4.14 (br m, 4H), 4.01 (br m, 1H), 3.20 (m, 4H), 2.82 (s, 3H), 2.63 (m, 1H), 2.41 (m, 3H).

Example 113

4-[(3R)-3-Aminopyrrolidin-1-yl]-8,8-difluoro-6,7,8,9-tetrahydro[1]benzothieno[3,2-d]pyrimidin-2-amine hydrochloride

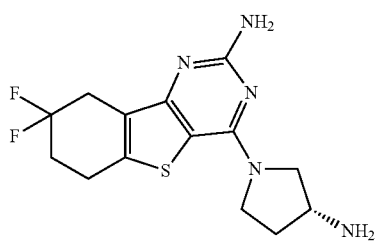

MS: 326.2 [M+H]+. 1H NMR (400 MHz, CD3OD): δ 4.15 (m, 5H), 3.20 (m, 4H), 2.57 (m, 1H), 2.41 (m, 2H), 2.32 (m, 1H).

Example 114

4-(1,4-Diazepan-1-yl)-8,8-difluoro-6,7,8,9-tetrahydro[1]benzothieno[3,2-d]pyrimidin-2-amine trifluoroacetate

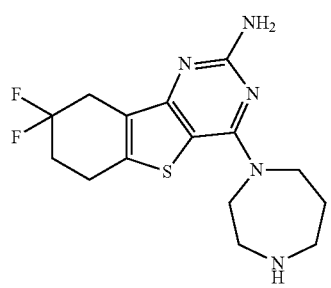 [SMILES: Nc1nc(N2CCCNCC2)c2sc3c(c2n1)CC(F)(F)CC3]

MS: 340.2 [M+H]+. 1H NMR (400 MHz, CD3OD): δ 4.31 (m, 2H), 4.18 (m, 2H), 3.62 (m, 2H), 3.40 (m, 2H), 3.25 (m, 2H), 3.18 (m, 2H), 2.39 (m, 2H), 2.28 (m, 2H).

Example 115

N4-(2-Aminoethyl)-8,8-difluoro-N4-methyl-6,7,8,9-tetrahydro[1]benzothieno[3,2-d]pyrimidine-2,4-diamine trifluoroacetate

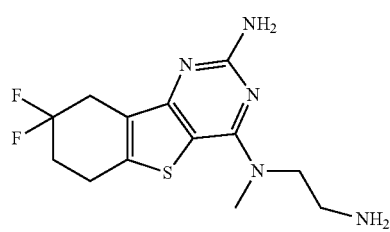 [SMILES: CN(CCN)c1nc(N)nc2c3c(sc12)CCC(F)(F)C3]

MS: 314.2 [M+H]+. 1H NMR (400 MHz, CD3OD): δ 4.12 (m, 2H), 3.61 (s, 3H), 3.34 (m, 2H), 3.26 (m, 2H), 3.18 (m, 2H), 2.41 (m, 2H).

Example 116

8,8-Difluoro-4-[(3R)-3-(methylamino)pyrrolidin-1-yl]-6,7,8,9-tetrahydro[1]benzofuro[3,2-d]pyrimidin-2-amine hydrochloride

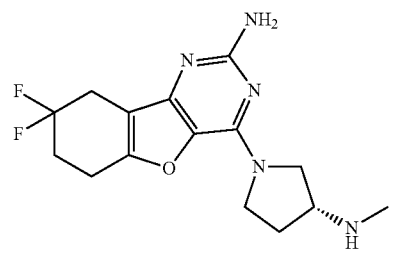 [SMILES: CN[C@@H]1CCN(c2nc(N)nc3c4c(oc23)CCC(F)(F)C4)C1]

MS: 324.2 [M+H]+. 1H NMR (400 MHz, CD3OD): δ 4.48-3.87 (m, 5H), 3.17 (m, 2H), 3.40 (m, 2H), 2.82 (s, 3H), 2.65-2.22 (m, 4H).

Example 117

4-[(3R)-3-Aminopyrrolidin-1-yl]-8,8-difluoro-6,7,8,9-tetrahydro[1]benzofuro[3,2-d]pyrimidin-2-amine hydrochloride

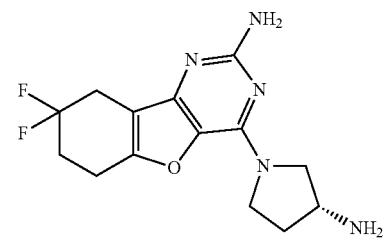 [SMILES: Nc1nc(N2CC[C@@H](N)C2)c2oc3c(c2n1)CC(F)(F)CC3]

MS: 310.2 [M+H]+. 1H NMR (400 MHz, CD3OD): δ 4.41-3.93 (m, 5H), 3.18 (m, 2H), 3.14 (m, 2H), 2.59 (m, 1H), 2.45 (m, 2H), 2.28 (m, 1H).

Example 118

8,8-Difluoro-4-piperazin-1-yl-6,7,8,9-tetrahydro[1]benzofuro[3,2-d]pyrimidin-2-amine hydrochloride

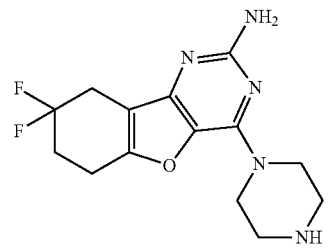 [SMILES: Nc1nc(N2CCNCC2)c2oc3c(c2n1)CC(F)(F)CC3]

MS: 310.2 [M+H]⁺. ¹H NMR (400 MHz, CD₃OD): δ 4.38 (m br, 4H), 3.44 (m, 4H), 3.19 (m, 2H), 3.05 (m, 2H), 2.44 (m, 2H).

Example 119

4-[(3S)-3-Aminopyrrolidin-1-yl]-8,8-difluoro-6,7,8,9-tetrahydro[1]benzothieno[3,2-d]pyrimidin-2-amine hydrochloride

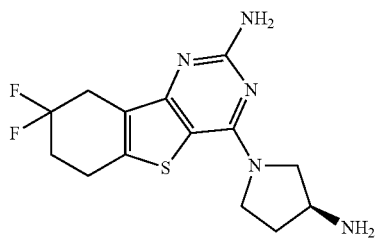 [SMILES: Nc1nc(N2CC[C@H](N)C2)c2sc3c(c2n1)CC(F)(F)CC3]

MS: 326.1 [M+H]⁺. ¹H NMR (400 MHz, CD₃OD): δ 4.13 (m, 5H), 3.18 (m, 2H), 3.14 (m, 2H), 2.56 (m, 1H), 2.39 (m, 2H), 2.28 (m, 1H).

Example 120

4-(3-Aminoazetidin-1-yl)-8,8-difluoro-6,7,8,9-tetrahydro[1]benzothieno[3,2-d]pyrimidin-2-amine (free amine)

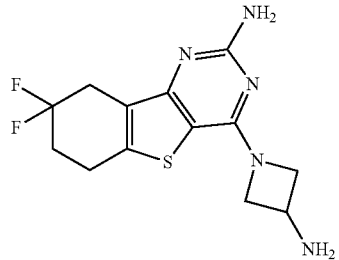 [SMILES: Nc1nc(N2CC(N)C2)c2sc3c(c2n1)CC(F)(F)CC3]

MS: 312.1 [M+H]⁺. ¹H NMR (400 MHz, CD₃OD): δ 4.53 (m, 2H), 4.02 (m, 3H), 3.09 (m, 2H), 3.03 (m, 2H), 2.35 (m, 2H).

Example 121

8,8-Difluoro-4-[(3aR,6aS)-5-methylhexahydropyrrolo[3,4-c]pyrrol-2(1H)-yl]-6,7,8,9-tetrahydro[1]benzothieno[3,2-d]pyrimidin-2-amine (free amine)

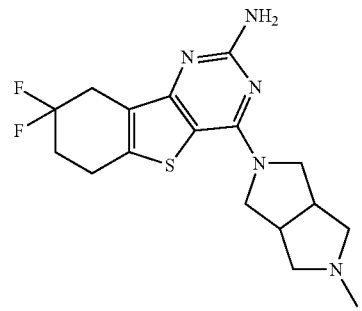 [SMILES: CN1CC2CN(c3nc(N)nc4c5c(sc34)CCC(F)(F)C5)CC2C1]

MS: 366.2 [M+H]⁺. ¹H NMR (400 MHz, CD₃OD): δ 3.97 (m, 2H), 3.77 (m, 2H), 3.08 (m, 6H), 2.80 (m, 2H), 2.53 (m, 2H), 2.35 (m, 5H).

Example 122

8,8-Difluoro-4-[(3S)-3-(methylamino)pyrrolidin-1-yl]-6,7,8,9-tetrahydro[1]benzofuro[3,2-d]pyrimidin-2-amine trifluoroacetate

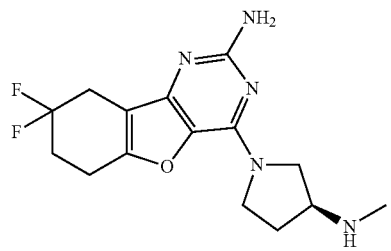 [SMILES: CN[C@H]1CCN(c2nc(N)nc3c4c(oc23)CCC(F)(F)C4)C1]

MS: 324.2 [M+H]⁺. ¹H NMR (400 MHz, CD₃OD): δ 4.37 (m, 0.5H), 4.25 (m, 1H), 4.19 (m, 0.5H), 4.08 (m, 1.5H), 3.99 (m, 1H), 3.85 (m, 0.5H), 3.16 (m, 2H), 3.02 (m, 2H), 2.81 (m, 3H), 2.62 (m, 0.5H), 2.43 (m, 3H), 2.29 (m, 0.5H).

Example 123

8,8-Difluoro-4-(4-methylpiperazin-1-yl)-6,7,8,9-tetrahydro[1]benzofuro[3,2-d]pyrimidin-2-amine trifluoroacetate

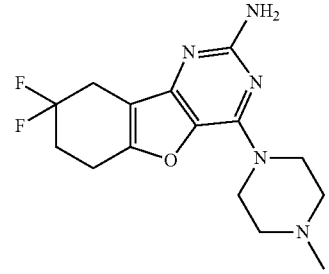 [SMILES: CN1CCN(c2nc(N)nc3c4c(oc23)CCC(F)(F)C4)CC1]

MS: 324.2 [M+H]⁺. ¹H NMR (400 MHz, CD₃OD): δ 4.95 (m br, 4H), 3.50 (m br, 4H), 3.17 (m, 2H), 3.04 (m, 2H), 2.98 (s, 3H), 2.43 (m, 2H).

Example 124

4-((R,R)-octahydropyrrolo[3,4-b]pyridin-6-yl)-8,8-difluoro-6,7,8,9-tetrahydro[1]benzofuro[3,2-d]pyrimidin-2-amine trifluoroacetate

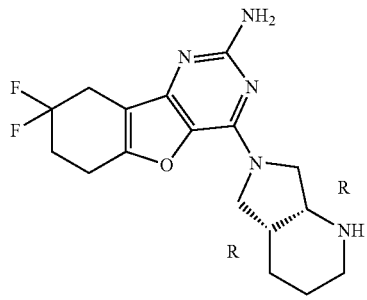

MS: 350.2 [M+H]+. 1H NMR (400 MHz, CD3OD): δ 4.40 (m, 0.4H), 4.29 (m, 1H), 4.21 (m, 0.6H), 4.03 (m, 2.6H), 3.73 (m, 0.4H), 3.41 (m, 1H), 3.16 (m, 2H), 3.02 (m, 3.6H), 2.81 (m, 0.4H), 2.43 (m, 2H), 1.90 (m, 4H).

Example 125

N4-(2-Aminoethyl)-8,8-difluoro-N4-methyl-6,7,8,9-tetrahydro[1]benzofuro[3,2-d]pyrimidine-2,4-diamine (free amine)

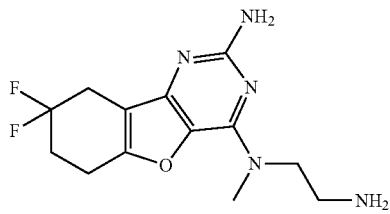 [SMILES: CN(CCN)c1nc(N)nc2c3c(oc12)CCC(F)(F)C3]

MS: 298.2 [M+H]+. 1H NMR (400 MHz, CD3OD): δ 4.21 (br m, 0.4H), 4.07 (m, 1.6H), 3.60 (s, 3H), 3.35 (m, 2H), 3.18 (m, 2H), 3.05 (m, 2H), 2.45 (m, 2H).

Example 126

4-[(3S)-3-Aminopyrrolidin-1-yl]-8,8-difluoro-6,7,8,9-tetrahydro[1]benzofuro[3,2-d]pyrimidin-2-amine hydrochloride

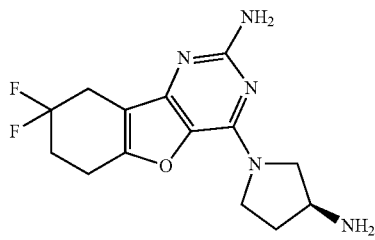 [SMILES: Nc1nc(N2CC[C@H](N)C2)c2oc3c(c2n1)CC(F)(F)CC3]

MS: 310.2 [M+H]+. 1H NMR (400 MHz, CD3OD): δ 4.41-3.93 (m, 5H), 3.11 (m, 2H), 3.08 (m, 2H), 2.57 (m, 0.6H), 2.42 (m, 2.4H), 2.33 (m, 0.6H), 2.20 (m, 0.4H).

Example 127

4-(3-Aminoazetidin-1-yl)-8,8-difluoro-6,7,8,9-tetrahydro[1]benzofuro[3,2-d]pyrimidin-2-amine hydrochloride

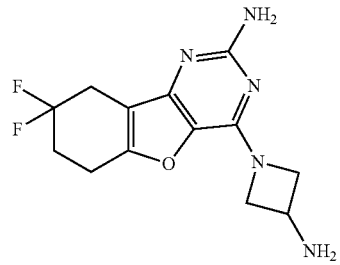

MS: 296.2 [M+H]+. 1H NMR (400 MHz, CD3OD): δ 4.98 (m, 1H), 4.68 (m, 2H), 4.37 (m, 2H), 3.18 (m, 2H), 3.02 (m, 2H), 2.47 (m, 2H).

Example 128

N4-(2-Aminoethyl)-8,8-difluoro-6,7,8,9-tetrahydro[1]benzothieno[3,2-d]pyrimidine-2,4-diamine hydrochloride

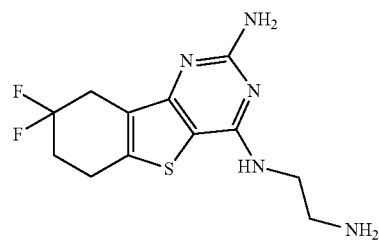 [SMILES: NCCNc1nc(N)nc2c3c(sc12)CCC(F)(F)C3]

MS: 300.1 [M+H]+. 1H NMR (400 MHz, CD3OD): δ 3.63 (m, 2H), 3.12 (m, 2H), 3.03 (m, 2H), 2.94 (m, 2H), 2.34 (m, 2H).

Example 129

8,8-Difluoro-4-[(3aR,6aS)-hexahydropyrrolo[3,4-c]pyrrol-2(1H)-yl]-6,7,8,9-tetrahydro[1]benzothieno[3,2-d]pyrimidin-2-amine (free amine)

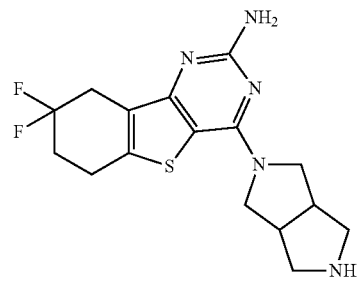 [SMILES: Nc1nc(N2CC3CNCC3C2)c2sc3c(c2n1)CC(F)(F)CC3]

MS: 352.2 [M+H]+. 1H NMR (400 MHz, CD3OD): δ 4.00 (m, 2H), 3.72 (m, 2H), 3.18-2.97 (m, 8H), 2.80 (m, 2H), 2.33 (m, 2H).

Example 130

4-(1,4-Diazepan-1-yl)-8,8-difluoro-6,7,8,9-tetrahydro[1]benzofuro[3,2-d]pyrimidin-2-amine (free amine)

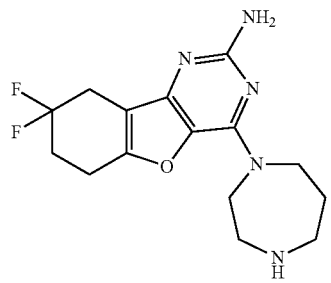 [SMILES: Nc1nc(N2CCCNCC2)c2oc3c(c2n1)CC(F)(F)CC3]

MS: 324.2 [M+H]+. 1H NMR (400 MHz, CD3OD): δ 3.96 (m, 4H), 3.05 (m, 4H), 2.88 (m, 4H), 2.38 (m, 2H), 1.96 (m, 2H).

Example 131

8,8-Dimethyl-4-(4-methylpiperazin-1-yl)-6,7,8,9-tetrahydro[1]benzothieno[3,2-d]pyrimidin-2-amine trifluoroacetate

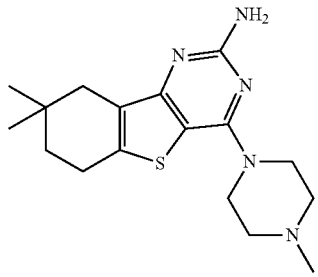

MS: 332.3 [M+H]+. 1H NMR (400 MHz, CD3OD): δ 4.60-4.21 (br m, 4H), 3.49 (m, 4H), 2.96 (m, 5H), 2.46 (s, 2H), 1.75 (m, 2H), 1.08 (s, 6H).

Example 132

4-(1,4-Diazepan-1-yl)-8,8-dimethyl-6,7,8,9-tetrahydro[1]benzothieno[3,2-d]pyrimidin-2-amine trifluoroacetate

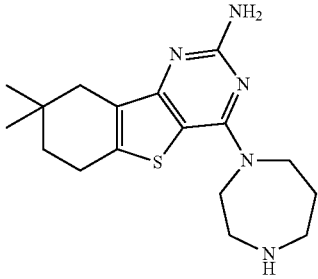 [SMILES: CC1(C)CCc2sc3c(N4CCCNCC4)nc(N)nc3c2C1]

MS: 332.3 [M+H]+. 1H NMR (400 MHz, CD3OD): δ 4.29 (m, 2H), 4.16 (m, 2H), 3.51 (m, 2H), 3.40 (m, 2H), 2.94 (m, 2H), 2.45 (s, 2H), 2.32 (m, 2H), 1.74 (m, 2H), 1.07 (s, 6H).

Example 133

N4-(2-Aminoethyl)-N4,8,8-trimethyl-6,7,8,9-tetrahydro[1]benzothieno[3,2-d]pyrimidine-2,4-diamine trifluoroacetate

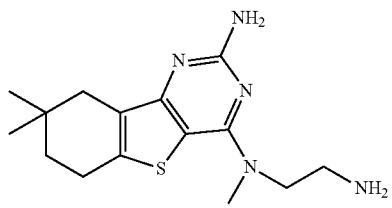 [SMILES: CN(CCN)c1nc(N)nc2c3c(sc12)CCC(C)(C)C3]

MS: 306.3 [M+H]+. 1H NMR (400 MHz, CD3OD): δ 3.92 (m, 2H), 3.33 (m, 2H), 2.97 (m, 2H), 2.77 (s, 3H), 2.45 (s, 2H), 1.74 (m, 2H), 1.07 (s, 6H).

Example 134

8,8-Dimethyl-4-[(3R)-3-(methylamino)pyrrolidin-1-yl]-6,7,8,9-tetrahydro[1]benzothieno[3,2-d]pyrimidin-2-amine hydrochloride

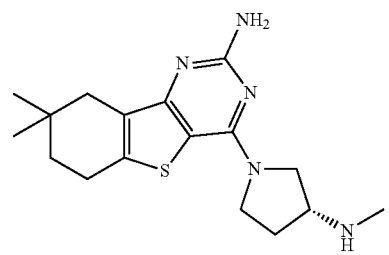

MS: 332.2 [M+H]+. 1H NMR (400 MHz, CD3OD): δ 4.62-3.93 (br m, 5H), 2.95 (m, 2H), 2.82 (s, 3H), 2.75-2.47 (br m, 2H), 2.45 (s, 2H), 1.73 (m, 2H), 1.07 (s, 6H).

Example 135

8,8-Dimethyl-4-[(3S)-3-(methylamino)pyrrolidin-1-yl]-6,7,8,9-tetrahydro[1]benzothieno[3,2-d]pyrimidin-2-amine hydrochloride

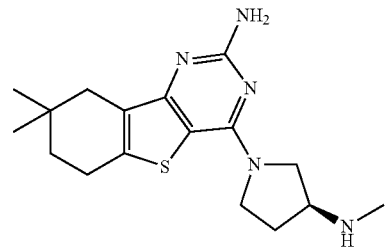

MS: 332.2 [M+H]+. 1H NMR (400 MHz, CD3OD): δ 4.09 (m, 2H), 3.97 (m, 2H), 3.82 (m, 1H), 2.88 (m, 2H), 2.70 (s, 3H), 2.47 (m, 1H), 2.43 (s, 2H), 2.26 (m, 1H), 1.71 (m, 2H), 1.05 (s, 6H).

Example 136

4-[(3R)-3-Aminopyrrolidin-1-yl]-8,8-dimethyl-6,7,8,9-tetrahydro[1]benzothieno[3,2-d]pyrimidin-2-amine hydrochloride

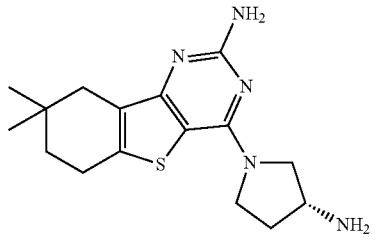 [SMILES: CC1(C)CCc2sc3c(N4CC[C@@H](N)C4)nc(N)nc3c2C1]

MS: 318.2 [M+H]$^+$. $^1$H NMR (400 MHz, CD$_3$OD): δ 4.47-3.98 (br m, 5H), 2.95 (m, 2H), 2.63 (m, 1H), 2.46 (s, 2H), 2.44-2.18 (m, 1H), 1.74 (m, 2H), 1.07 (s, 6H).

Example 137

8,8-Dimethyl-4-[(3R)-3-(methylamino)pyrrolidin-1-yl]-6,7,8,9-tetrahydro[1]benzofuro[3,2-d]pyrimidin-2-amine hydrochloride

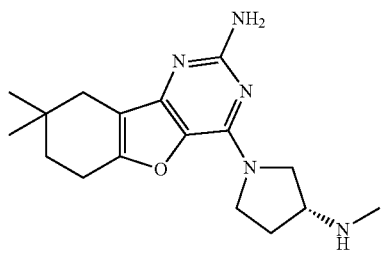

MS: 316.3 [M+H]$^+$. $^1$H NMR (400 MHz, CD$_3$OD): δ 4.48-3.85 (br m, 5H), 2.80 (m, 5H), 2.63-2.20 (br m, 2H), 2.39 (s, 2H), 1.75 (m, 2H), 1.07 (s, 6H).

Example 138

4-(4-Methylpiperazin-1-yl)-8-(trifluoromethyl)-6,7,8,9-tetrahydro[1]benzothieno[3,2-d]pyrimidin-2-amine hydrochloride

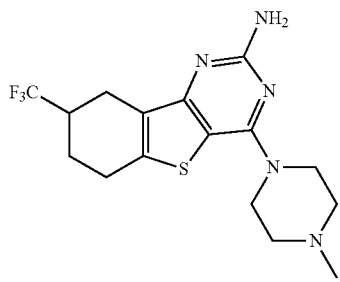 [SMILES: CN1CCN(c2nc(N)nc3c4c(sc23)CCC(C(F)(F)F)C4)CC1]

MS: 372.1 [M+H]$^+$. $^1$H NMR (400 MHz, CD$_3$OD): δ 3.93 (m, 4H), 3.00 (m, 3H), 2.64 (m, 2H), 2.56 (m, 4H), 2.35 (s, 3H), 2.30 (m, 1H), 1.83 (m, 1H).

Example 139

4-[(3R)-3-Aminopyrrolidin-1-yl]-8-tert-butyl-6,7,8,9-tetrahydro[1]benzothieno[3,2-d]pyrimidin-2-amine hydrochloride

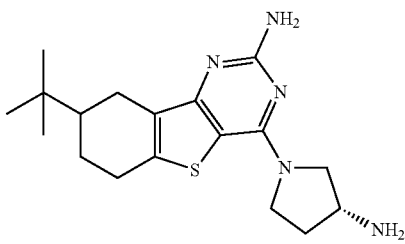 [SMILES: CC(C)(C)C1CCc2sc3c(N4CC[C@@H](N)C4)nc(N)nc3c2C1]

MS: 346.2 [M+H]$^+$. $^1$H NMR (400 MHz, CD$_3$OD): δ 4.12 (m, 5H), 3.06 (m, 1H), 3.87 (m, 2H), 2.60 (br m, 1H), 2.40-2.19 (m, 3H), 1.52 (m, 2H), 1.05 (s, 9H).

Example 140

8-Methyl-4-[(3R)-3-(methylamino)pyrrolidin-1-yl]-6,7,8,9-tetrahydro[1]benzofuro[3,2-d]pyrimidin-2-amine hydrochloride

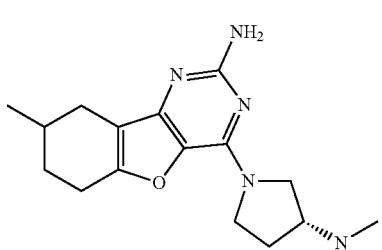

MS: 302.2 [M+H]$^+$. $^1$H NMR (400 MHz, CD$_3$OD): δ 4.91 (m, 2H), 3.77 (m, 1H), 3.66 (m, 1H), 3.46 (m, 1H), 2.65 (m, 3H), 2.47 (s, 3H), 2.23 (m, 1H), 2.04 (m, 1H), 1.93 (m, 2H), 1.83 (m, 1H), 1.51 (m, 1H), 1.08 (m, 3H).

Example 141

4-[(3R)-3-(Methylamino)pyrrolidin-1-yl]-8-(trifluoromethyl)-6,7,8,9-tetrahydro[1]benzothieno[3,2-d]pyrimidin-2-amine hydrochloride

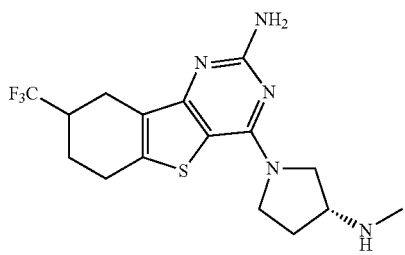 [SMILES: CN[C@@H]1CCN(c2nc(N)nc3c4c(sc23)CCC(C(F)(F)F)C4)C1]

MS: 372.1 [M+H]$^+$. $^1$H NMR (400 MHz, CD$_3$OD): δ 4.00 (m, 2H), 3.87 (m, 1H), 3.72 (m, 1H), 3.53 (m, 1H), 2.98 (m, 3H), 2.61 (m, 2H), 2.53 (s, 3H), 2.32 (m, 2H), 2.04 (m, 1H), 1.84 (m, 1H).

Example 142

8-tert-Butyl-4-[(3R)-3-(methylamino)pyrrolidin-1-yl]-6,7,8,9-tetrahydro[1]benzothieno[3,2-d]pyrimidin-2-amine hydrochloride

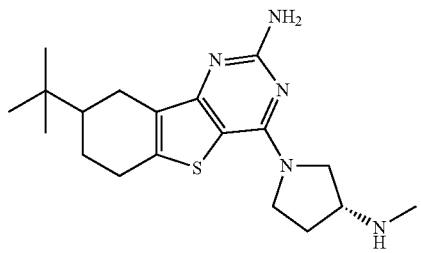 [SMILES: CN[C@@H]1CCN(c2nc(N)nc3c4c(sc23)CCC(C(C)(C)C)C4)C1]

MS: 360.2 [M+H]⁺. ¹H NMR (400 MHz, CD₃OD): δ 4.15 (m, 5H), 3.08 (m, 1H), 2.89 (m, 2H), 2.82 (s, 3H), 2.60 (m, 1H), 2.39 (m, 2H), 2.23 (m, 1H), 1.55 (m, 2H), 1.03 (m, 9H).

Example 143

4-[3-(Aminomethyl)azetidin-1-yl]-8-methyl-6,7,8,9-tetrahydro[1]benzothieno[3,2-d]pyrimidin-2-amine hydrochloride

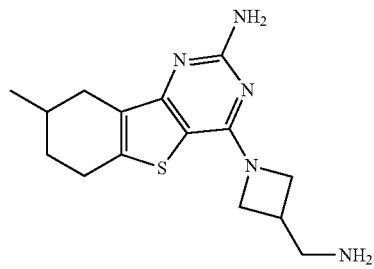 [SMILES: CC1CCc2sc3c(N4CC(CN)C4)nc(N)nc3c2C1]

MS: 304.1 [M+H]⁺. ¹H NMR (400 MHz, CD₃OD): δ 4.50 (m, 2H), 4.16 (m, 2H), 3.37 (m, 2H), 3.23 (m, 1H), 2.95 (m, 2H), 2.82 (m, 1H), 2.20 (m, 1H), 2.03 (m, 2H), 1.55 (m, 1H), 1.14 (m, 3H).

Example 144

4-[(3R)-3-Aminopyrrolidin-1-yl]-8-methyl-6,7,8,9-tetrahydro[1]benzofuro[3,2-d]pyrimidin-2-amine hydrochloride

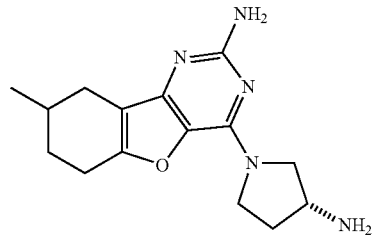 [SMILES: CC1CCc2oc3c(N4CC[C@@H](N)C4)nc(N)nc3c2C1]

MS: 288.1 [M+H]⁺. ¹H NMR (300 MHz, DMSO-d6) δ 13.22 (br s, 1H), 8.45 (s, 3H), 7.60 (br s, 1H), 4.15-3.90 (m, 4H), 2.94-2.80 (m, 3H), 2.27-2.12 (m, 3H), 1.96-1.90 (m, 2H), 1.57-1.50 (m, 1H), 1.07 (d, J=6.3, 3H).

Example 145

4-(1,4-Diazepan-1-yl)-8-methyl-6,7,8,9-tetrahydro[1]benzofuro[3,2-d]pyrimidin-2-amine hydrochloride

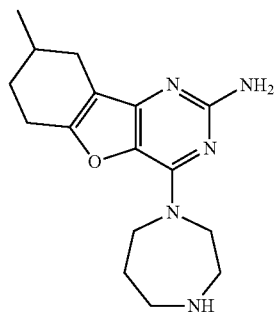 [SMILES: CC1CCc2oc3c(N4CCCNCC4)nc(N)nc3c2C1]

MS: 302.1 [M+H]⁺. ¹H NMR (300 MHz, DMSO-d6) δ 13.20 (br s, 1H), 9.18 (br s, 2H), 7.60 (br s, 2H), 4.16-3.95 (m, 3H), 3.75-3.20 (m, 7H), 2.95-2.80 (m, 3H), 2.20-2.00 (m, 3H), 1.99-1.82 (m, 2H), 1.53 (m, 1H), 1.07 (d, J=6.3, 3H).

Example 146

8-Methyl-4-piperazin-1-yl-6,7,8,9-tetrahydro[1]benzothieno[3,2-d]pyrimidin-2-amine hydrochloride

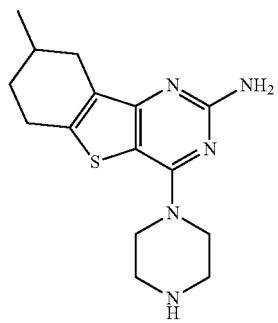 [SMILES: CC1CCc2sc3c(N4CCNCC4)nc(N)nc3c2C1]

MS: 304.1 [M+H]⁺. ¹H NMR (300 MHz, DMSO-d6) δ 13.51 (br s, 1H), 9.34 (s, 2H), 8.10-7.80 (br s, 1H), 4.22 (br s, 4H), 3.42-3.32 (m, 4H), 2.94-2.90 (m, 3H), 2.20 (m, 1H), 1.95 (m, 2H), 1.59-1.49 (m, 2H), 1.10 (d, J=6.3, 3H).

Example 147

4-(3,8-Diazabicyclo[3.2.1]oct-3-yl)-8-(trifluoromethyl)-6,7,8,9-tetrahydro[1]benzothieno[3,2-d]pyrimidin-2-amine hydrochloride

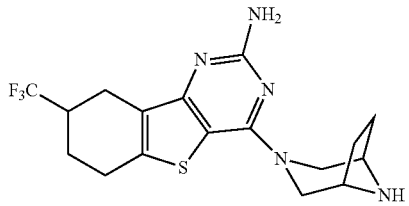 [SMILES: Nc1nc(N2CC3CCC(C2)N3)c2sc3c(c2n1)CC(C(F)(F)F)CC3]

MS: 384.1 [M+H]⁺. ¹H NMR (300 MHz, DMSO-d6) δ 13.62 (br s, 1H), 10.14 (br s, 1H), 9.87 (br s, 1H), 8.1-7.8 (br,

1H), 4.51 (br s, 2H), 4.25 (m, 2H), 3.98-3.50 (m, 2H), 3.10-2.91 (m, 4H), 2.64-2.59 (m, 1H), 2.25-2.20 (m, 1H), 2.00-1.85 (m, 5H).

Example 148

4-piperazin-1-yl-8-(trifluoromethyl)-6,7,8,9-tetrahydro[1]benzothieno[3,2-d]pyrimidin-2-amine hydrochloride

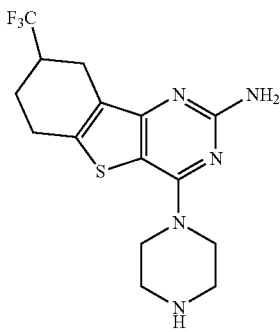 [SMILES: Nc1nc(N2CCNCC2)c2sc3c(c2n1)CC(C(F)(F)F)CC3]

MS: 358.1 [M+H]$^+$. $^1$H NMR (300 MHz, DMSO-d6) δ 13.64 (br s, 1H), 9.81 (s, 2H), 7.67 (br s, 2H), 4.22 (br s, 4H), 3.50 (br s, 2H), 3.16 (br s, 2H), 2.96-2.90 (br m, 4H), 2.58 (m, 1H), 2.25 (m, 1H), 1.81-1.75 (m, 1H).

Example 149

4-(1,4-Diazepan-1-yl)-8-methyl-6,7,8,9-tetrahydro[1]benzothieno[3,2-d]pyrimidin-2-amine hydrochloride

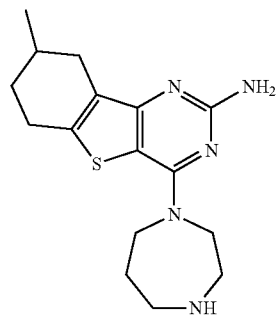 [SMILES: CC1CCc2sc3c(N4CCCNCC4)nc(N)nc3c2C1]

MS: 318.1 [M+H]$^+$. $^1$H NMR (300 MHz, DMSO-d6) δ 13.08 (br s, 1H), 9.21 (br s, 2H), 7.60 (br s, 2H), 4.18-3.99 (m, 3H), 3.75-3.20 (m, 6H), 3.01-2.80 (m, 3H), 2.20-2.05 (m, 3H), 1.99-1.82 (m, 2H), 1.53 (m, 1H), 1.12 (d, J=6.3, 3H).

Example 150

8-Methoxy-4-piperazin-1-yl-6,7,8,9-tetrahydro[1]benzothieno[3,2-d]pyrimidin-2-amine hydrochloride

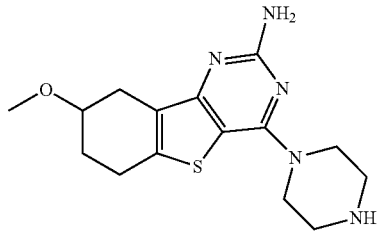 [SMILES: COC1CCc2sc3c(N4CCNCC4)nc(N)nc3c2C1]

MS: 320.1 [M+H]$^+$. $^1$H NMR (300 MHz, DMSO-d6) δ 13.74 (s, 1H), 9.88 (s, 2H), 4.22 (s, 2H), 3.73 (m, 1H), 3.33 (s, 3H), 2.92-2.72 (m, 2H), 2.04 (m, 2H).

Example 151

4-(3,8-Diazabicyclo[3.2.1]oct-3-yl)-6,6-dimethyl-6,7,8,9-tetrahydro[1]benzofuro[3,2-d]pyrimidin-2-amine hydrochloride

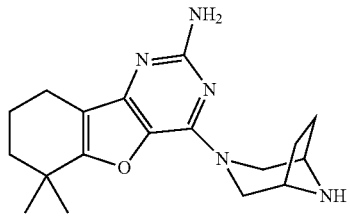 [SMILES: CC1(C)CCCc2c1oc1c(N3CC4CCC(C3)N4)nc(N)nc21]

MS: 328.1 [M+H]$^+$. $^1$H NMR (300 MHz, DMSO-d6) δ 13.8 (br s, 1H), 9.98 (br s, 1H), 9.59 (br s, 1H), 7.50 (br s, 1H), 4.62-4.57 (m, 2H), 3.73 (s, 2H), 3.50-3.40 (br m, 2H), 2.03-2.00 (m, 2H), 1.79-1.70 (m, 6H), 1.50 (s, 6H).

Biological Methods: Binding Assay on Recombinant Human Histamine H$_4$ Receptor.

SK-N-MC cells or COS7 cells were transiently transfected with pH4R and grown in 150 cm$^2$ tissue culture dishes. Cells were washed with saline solution, scraped with a cell scraper and collected by centrifugation (1000 rpm, 5 min). Cell membranes were prepared by homogenization of the cell pellet in 20 mM Tris-HCl with a polytron tissue homogenizer for 10 sec at high speed. Homogenate was centrifuged at 1000 rpm for 5 min at 4° C. The supernatant was then collected and centrifuged at 20,000×g for 25 min at 4° C. The final pellet was resuspended in 50 mM Tris-HCl. Cell membranes were incubated with $^3$H-histamine (5-70 nM) in the presence or absence of excess histamine (10,000 nM). Incubation occurred at room temperature for 45 min. Membranes were harvested by rapid filtration over Whatman GF/C filters and washed 4 times with ice-cold 50 mM Tris HCl. Filters were then dried, mixed with scintillant and counted for radioactivity. SK-N-MC or COS7 cells expressing human histamine H$_4$ receptor were used to measure the affinity of binding of other compounds and their ability to displace $^3$H-ligand binding by incubating the above-described reaction in the presence of various concentrations of inhibitor or compound to be tested. For competition binding studies using $^3$H-histamine, K values were calculated, based on an experimentally determined K$_D$ value of 5 nM and a ligand concentration of 5 nM, according to Y.-C. Cheng and W. H. Prusoff (*Biochem. Pharmacol.* 1973, 22(23):3099-3108): $K_i=(IC_{50})/(1+([L]/(K_D))$. Results for the compounds tested in this assay are presented in Table 1 as an average of results obtained.

TABLE 1

| Ex. | K$_i$ (μM) |
|---|---|
| 1 | 0.503 |
| 2 | 0.013 |
| 3 | 0.023 |
| 4 | 0.021 |
| 5 | 0.008 |
| 6 | 0.005 |
| 7 | 0.003 |
| 8 | 0.053 |
| 9 | 0.110 |
| 10 | 0.132 |

TABLE 1-continued

| Ex. | $K_i$ (μM) |
|---|---|
| 11 | 0.454 |
| 12 | 0.182 |
| 13 | 0.574 |
| 14 | 1.050 |
| 15 | 0.286 |
| 16 | 0.071 |
| 17 | 0.142 |
| 18 | 0.221 |
| 19 | 0.244 |
| 20 | 0.005 |
| 21 | 0.003 |
| 22 | 0.003 |
| 23 | 0.083 |
| 24 | 0.002 |
| 25 | 0.507 |
| 26 | 0.032 |
| 27 | >10 |
| 28 | 0.066 |
| 30 | 0.145 |
| 31 | 0.005 |
| 32 | 0.002 |
| 33 | 0.390 |
| 34 | 0.123 |
| 35 | 0.417 |
| 36 | >10 |
| 37 | 0.015 |
| 38 | 0.300 |
| 39 | 0.062 |
| 40 | 0.503 |
| 41 | 1.007 |
| 42 | 0.467 |
| 43 | 0.007 |
| 44 | 0.011 |
| 45 | 0.004 |
| 46 | 0.021 |
| 47 | 0.005 |
| 48 | 0.003 |
| 49 | 2.260 |
| 50 | 0.647 |
| 51 | 0.205 |
| 52 | 0.067 |
| 53 | 0.387 |
| 54 | 1.613 |
| 55 | 0.033 |
| 56 | 0.010 |
| 57 | 0.023 |
| 58 | 0.014 |
| 59 | 0.009 |
| 112 | 0.006 |
| 113 | 0.0011 |
| 114 | 0.0021 |
| 115 | 0.021 |
| 116 | 0.00048 |
| 117 | 0.0068 |
| 118 | 0.029 |
| 119 | 0.021 |
| 120 | 0.17 |
| 121 | 0.15 |
| 122 | 0.0070 |
| 123 | 0.015 |
| 124 | 0.033 |
| 125 | 0.15 |
| 126 | 0.0061 |
| 127 | 0.064 |
| 128 | 0.15 |
| 129 | 0.68 |
| 130 | 0.0082 |
| 132 | 0.035 |
| 133 | 0.054 |
| 134 | 0.0076 |
| 135 | 0.035 |
| 136 | 0.0077 |
| 137 | 0.018 |

While the invention has been illustrated by reference to examples, it is understood that the invention is intended not to be limited to the foregoing detailed description.

What is claimed is:

1. A chemical entity selected from the group consisting of compounds of Formula (I) and pharmaceutically acceptable salts of compounds of Formula (I):

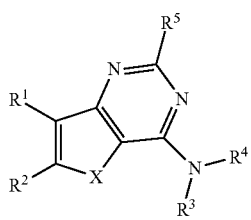

(I)

wherein

X is O;

$R^1$ is H, methyl, or bromo;

$R^2$ is H or $C_{1-4}$alkyl;

—$N(R^3)R^4$ is one of the following moieties, wherein $R^3$ and $R^4$ are taken together or separately as defined by each one of said moieties:

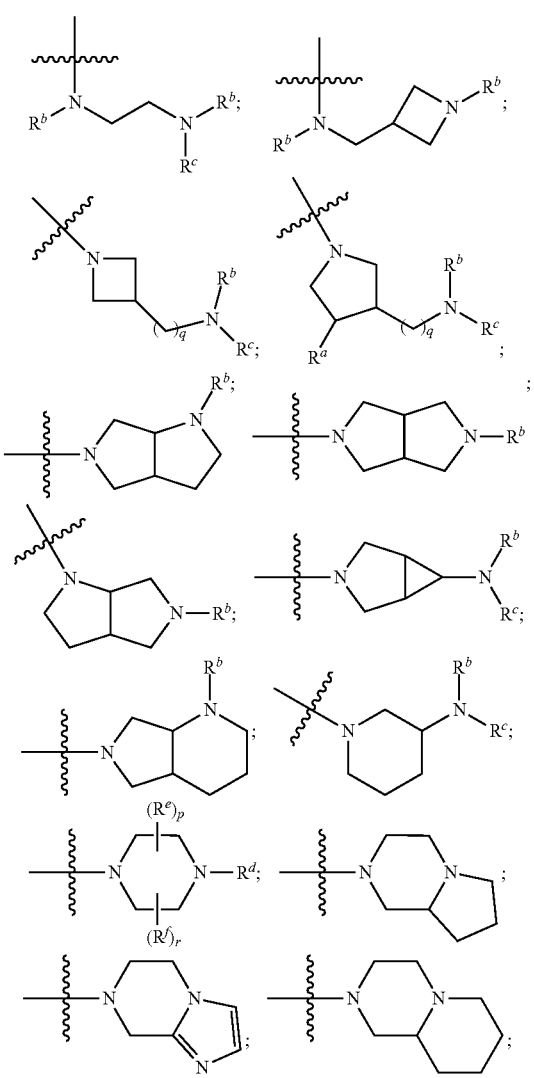

-continued

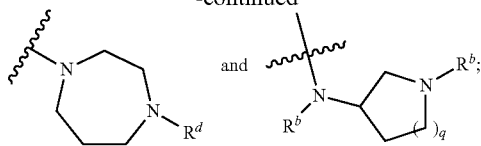

where q is 0 or 1;
p is 0 or 1;
r is 0 or 1;
$R^a$ is H or OH;
$R^b$ and $R^c$ are each independently H or $C_{1-3}$alkyl;
$R^d$ is H or a $C_{1-3}$alkyl group unsubstituted or substituted with OH or $NH_2$;
$R^e$ and $R^f$ are each methyl, or $R^e$ and $R^f$ taken together form a methylene or ethylene bridge; and
$R^5$ is H or $NH_2$;
provided that when $R^1$ is H and $R^2$ is H, methyl, or tert-butyl, then —$N(R^3)R^4$ is not 3-aminopyrrolidine, 3-aminopiperidine, piperazine, or N-methylpiperazine.

2. A chemical entity as in claim 1, wherein $R^1$ is H.
3. A chemical entity as in claim 1, wherein $R^2$ is H or tert-butyl.
4. A chemical entity as in claim 1, wherein —$N(R^3)R^4$ is one of the following moieties:

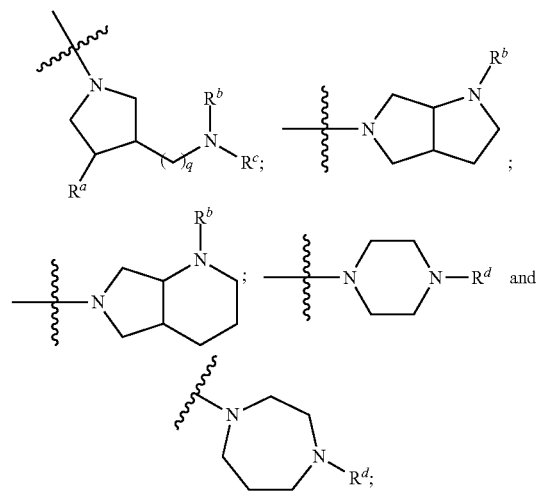

where q is 0;
$R^a$ is H;
$R^b$ and $R^c$ are each independently H or methyl; and
$R^d$ is H or methyl.

5. A chemical entity as in claim 1, wherein —$N(R^3)R^4$ is one of the following moieties:

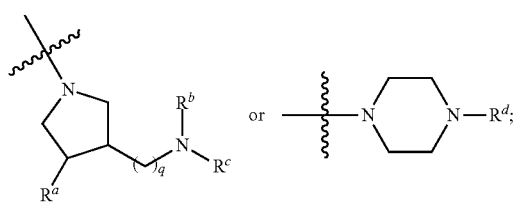

where q is 0;
$R^a$ is H;

$R^b$ and $R^c$ are each independently H or methyl; and
$R^d$ is H or methyl.

6. A chemical entity as in claim 1, wherein $R^5$ is $NH_2$.
7. A pharmaceutical composition comprising an effective amount of at least one chemical entity selected from compounds of Formula (I) and pharmaceutically acceptable salts of compounds of Formula (I):

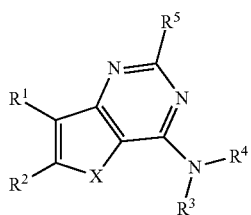

wherein
X is O;
$R^1$ is H, methyl, or bromo;
$R^2$ is H or $C_{1-4}$alkyl;
—$N(R^3)R^4$ is one of the following moieties, wherein $R^3$ and $R^4$ are taken together or separately as defined by each one of said moieties:

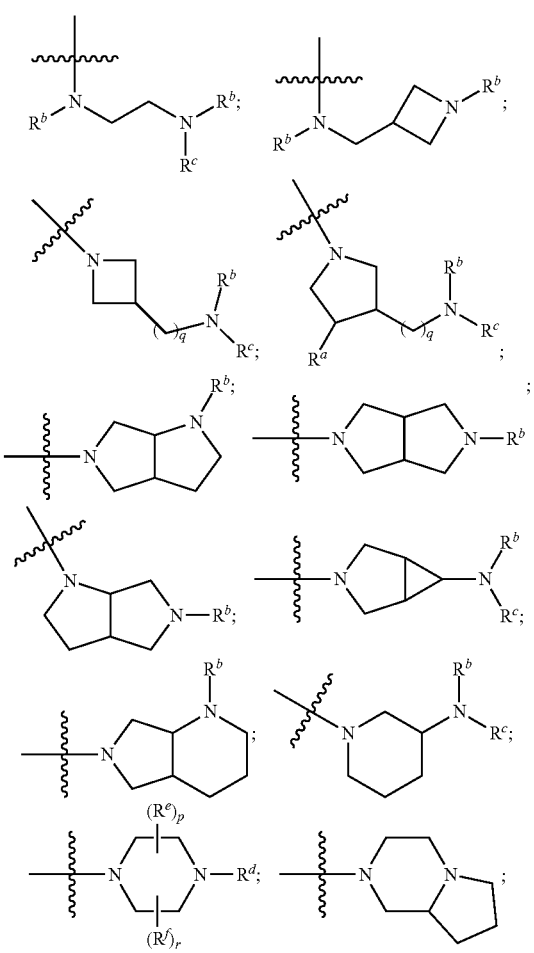

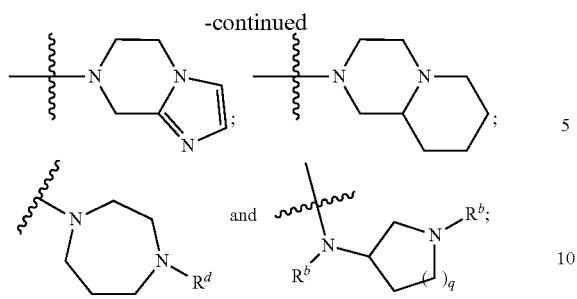

where q is 0 or 1;
p is 0 or 1;
r is 0 or 1;
$R^a$ is H or OH;
$R^b$ and $R^c$ are each independently H or $C_{1-3}$alkyl;
$R^d$ is H or a $C_{1-3}$alkyl group unsubstituted or substituted with OH or $NH_2$;
$R^e$ and $R^f$ are each methyl, or $R^e$ and $R^f$ taken together form a methylene or ethylene bridge; and
$R^5$ is H or $NH_2$;
provided that when $R^1$ is H and $R^2$ is H, methyl, or tert-butyl, then —$N(R^3)R^4$ is not 3-aminopyrrolidine, 3-aminopiperidine, piperazine, or N-methylpiperazine.

* * * * *